United States Patent
Pinney et al.

(10) Patent No.: US 7,787,986 B2
(45) Date of Patent: Aug. 31, 2010

(54) COMMUNICATION NETWORK FOR USE IN AUTOMATICALLY DELIVERING PRESCRIPTIONS

(75) Inventors: Linda J. Pinney, Del Mar, CA (US); John A. Beane, San Diego, CA (US); Angus R. Colson, Jamul, CA (US); David R. Williams, Rainbow, CA (US); Keith Kopitzke, Fallbrook, CA (US); Keith W. Reynolds, Cardiff by the Sea, CA (US); Erik Howard Barnes, Solana Beach, CA (US)

(73) Assignee: Asteres, Inc., San Diego, CA (US)

( * ) Notice: Subject to any disclaimer, the term of this patent is extended or adjusted under 35 U.S.C. 154(b) by 0 days.

(21) Appl. No.: 11/688,183

(22) Filed: Mar. 19, 2007

(65) Prior Publication Data
US 2007/0162183 A1   Jul. 12, 2007

Related U.S. Application Data

(63) Continuation of application No. 11/001,110, filed on Nov. 30, 2004, now abandoned, which is a continuation-in-part of application No. 10/880,269, filed on Jun. 29, 2004, now abandoned, which is a continuation of application No. 10/801,321, filed on Mar. 16, 2004, now Pat. No. 7,123,989.

(60) Provisional application No. 60/484,544, filed on Jul. 1, 2003, provisional application No. 60/576,005, filed on Jun. 1, 2004.

(51) Int. Cl.
*G06F 17/00* (2006.01)

(52) U.S. Cl. ............... 700/232; 700/236; 700/237; 700/244; 221/9
(58) Field of Classification Search ......... 700/231–244; 221/9
See application file for complete search history.

(56) References Cited

U.S. PATENT DOCUMENTS 3,786,421 A   1/1974   Wostle et al.

(Continued)

FOREIGN PATENT DOCUMENTS

WO   WO-01/31593   5/2001

(Continued)

OTHER PUBLICATIONS

Express Scripts company literature; published or in public use at least as early as Jun. 30, 2002; 2 pages.

(Continued)

*Primary Examiner*—Gene Crawford
*Assistant Examiner*—Michael K Collins
(74) *Attorney, Agent, or Firm*—Foley & Lardner LLP; Steven A. Moore; Kurt M. Kjelland

(57) ABSTRACT

The present invention provides a random access and random load dispensing unit including a housing, at least one support located in the housing and defining a first axis, a plurality of platforms movable along the support along the first axis, a plurality of bins supported on the platforms, the bins being movable with the platforms, and a shuttle assembly movable along the first axis and further movable along a second axis substantially perpendicular to the first axis between the plurality of platforms to access and retrieve products stored in the bins.

84 Claims, 37 Drawing Sheets

U.S. PATENT DOCUMENTS

| | | |
|---|---|---|
| 3,941,977 A | 3/1976 | Voss et al. |
| 3,943,335 A | 3/1976 | Kinker et al. |
| 4,359,631 A | 11/1982 | Lockwood et al. |
| 4,456,122 A | 6/1984 | Kalal |
| 4,519,522 A | 5/1985 | McElwee |
| 4,546,901 A | 10/1985 | Buttarazzi |
| 4,812,629 A | 3/1989 | O'Neil et al. |
| 4,814,592 A | 3/1989 | Bradt et al. |
| 4,839,505 A | 6/1989 | Bradt et al. |
| 4,858,743 A | 8/1989 | Paraskevakos et al. |
| 4,866,255 A | 9/1989 | Sing |
| 4,896,024 A | 1/1990 | Morello et al. |
| 4,951,308 A | 8/1990 | Bishop et al. |
| 4,995,498 A | 2/1991 | Menke |
| 5,013,897 A | 5/1991 | Harman et al. |
| 5,020,958 A | 6/1991 | Tuttobene |
| 5,036,472 A | 7/1991 | Buckley et al. |
| 5,042,686 A | 8/1991 | Stucki |
| 5,059,772 A | 10/1991 | Younglove |
| 5,088,586 A | 2/1992 | Isobe et al. |
| 5,095,195 A | 3/1992 | Harman et al. |
| 5,105,978 A | 4/1992 | Trouteaud et al. |
| 5,113,351 A | 5/1992 | Bostic |
| 5,139,384 A | 8/1992 | Tuttobene |
| 5,143,193 A * | 9/1992 | Geraci ................. 194/212 |
| 5,159,560 A | 10/1992 | Newell et al. |
| 5,172,829 A | 12/1992 | Dellicker, Jr. |
| 5,205,436 A | 4/1993 | Savage |
| 5,212,649 A | 5/1993 | Pelletier et al. |
| 5,303,844 A | 4/1994 | Muehlberger |
| 5,313,393 A | 5/1994 | Varley et al. |
| 5,337,920 A * | 8/1994 | Clausen ..................... 221/5 |
| 5,385,265 A | 1/1995 | Schlamp |
| 5,408,443 A | 4/1995 | Weinberger |
| 5,445,294 A | 8/1995 | Gardner et al. |
| 5,445,295 A | 8/1995 | Brown |
| 5,468,110 A | 11/1995 | McDonald et al. |
| 5,482,139 A | 1/1996 | Rivalto |
| 5,499,707 A | 3/1996 | Steury |
| 5,502,944 A | 4/1996 | Kraft et al. |
| 5,593,267 A | 1/1997 | McDonald et al. |
| 5,597,995 A * | 1/1997 | Williams et al. ............ 235/375 |
| 5,713,485 A | 2/1998 | Liff et al. |
| 5,713,487 A | 2/1998 | Coughlin |
| 5,713,648 A | 2/1998 | Geib et al. |
| 5,720,154 A | 2/1998 | Lasher et al. |
| 5,748,485 A | 5/1998 | Christiansen et al. |
| 5,790,409 A | 8/1998 | Fedor et al. |
| 5,797,515 A | 8/1998 | Liff et al. |
| 5,812,410 A | 9/1998 | Lion et al. |
| 5,838,575 A | 11/1998 | Lion |
| 5,839,257 A | 11/1998 | Soderstrom et al. |
| 5,880,443 A | 3/1999 | McDonald et al. |
| 5,893,459 A | 4/1999 | Croft |
| 5,893,697 A | 4/1999 | Zini et al. |
| 5,907,493 A | 5/1999 | Boyer et al. |
| 5,930,145 A | 7/1999 | Yuyama et al. |
| 5,945,651 A | 8/1999 | Chorosinski et al. |
| 5,963,453 A | 10/1999 | East |
| 5,971,593 A | 10/1999 | McGrady |
| 6,003,006 A | 12/1999 | Colella et al. |
| 6,021,392 A | 2/2000 | Lester et al. |
| 6,039,251 A | 3/2000 | Holowko et al. |
| 6,068,156 A | 5/2000 | Liff et al. |
| 6,131,399 A | 10/2000 | Hall |
| 6,152,364 A | 11/2000 | Schoonen et al. |
| 6,170,230 B1 | 1/2001 | Chudy et al. |
| 6,199,720 B1 | 3/2001 | Rudick et al. |
| 6,202,923 B1 | 3/2001 | Boyer et al. |
| 6,219,587 B1 | 4/2001 | Ahlin et al. |
| 6,230,927 B1 | 5/2001 | Schoonen et al. |
| 6,230,930 B1 | 5/2001 | Sorenson et al. |
| 6,256,967 B1 | 7/2001 | Hebron et al. |
| 6,263,259 B1 | 7/2001 | Bartur |
| 6,283,322 B1 | 9/2001 | Liff et al. |
| 6,305,377 B1 | 10/2001 | Portwood et al. |
| 6,324,520 B1 | 11/2001 | Walker et al. |
| 6,330,491 B1 | 12/2001 | Lion |
| 6,352,200 B1 | 3/2002 | Schoonen et al. |
| 6,354,498 B1 | 3/2002 | Lutz |
| 6,370,841 B1 | 4/2002 | Chudy et al. |
| 6,393,339 B1 | 5/2002 | Yeadon |
| 6,397,126 B1 | 5/2002 | Nelson |
| 6,397,193 B1 | 5/2002 | Walker et al. |
| 6,416,270 B1 | 7/2002 | Steury et al. |
| 6,421,579 B1 * | 7/2002 | Dimitri et al. ............... 700/214 |
| 6,438,451 B1 | 8/2002 | Lion |
| 6,443,359 B1 | 9/2002 | Green et al. |
| 6,449,627 B1 | 9/2002 | Baer et al. |
| 6,449,927 B2 | 9/2002 | Hebron et al. |
| 6,464,142 B1 | 10/2002 | Denenberg et al. |
| 6,471,089 B2 | 10/2002 | Liff et al. |
| 6,499,627 B2 | 12/2002 | Arai |
| 6,505,754 B1 | 1/2003 | Kenny et al. |
| 6,522,772 B1 | 2/2003 | Morrison et al. |
| 6,529,801 B1 * | 3/2003 | Rosenblum ................. 700/237 |
| 6,533,170 B1 | 3/2003 | Kit |
| 6,539,282 B2 | 3/2003 | Metcalf et al. |
| 6,556,889 B2 | 4/2003 | Rudick et al. |
| 6,564,121 B1 | 5/2003 | Wallace et al. |
| 6,581,798 B2 | 6/2003 | Liff et al. |
| 6,584,309 B1 | 6/2003 | Whigham |
| 6,588,548 B1 | 7/2003 | Dewitt |
| 6,594,549 B2 | 7/2003 | Siegel |
| 6,597,970 B1 | 7/2003 | Steury et al. |
| 6,611,810 B1 | 8/2003 | Kolls |
| 6,644,455 B2 * | 11/2003 | Ichikawa ................... 194/205 |
| 6,648,153 B2 | 11/2003 | Holmes |
| 6,697,704 B2 | 2/2004 | Rosenblum |
| 6,711,460 B1 | 3/2004 | Reese |
| 6,711,465 B2 | 3/2004 | Tomassi |
| 6,766,218 B2 | 7/2004 | Rosenblum |
| 6,814,255 B2 | 11/2004 | Liff et al. |
| 6,847,861 B2 | 1/2005 | Lunak et al. |
| 6,874,684 B1 * | 4/2005 | Denenberg et al. .......... 235/381 |
| 6,877,655 B1 | 4/2005 | Robertson et al. |
| 6,892,041 B1 | 5/2005 | Shehata et al. |
| 6,892,941 B2 * | 5/2005 | Rosenblum ................. 235/383 |
| 6,973,369 B2 * | 12/2005 | Trimmer et al. ............. 700/214 |
| 7,010,387 B2 * | 3/2006 | Lantry et al. ................ 700/214 |
| 7,086,558 B1 * | 8/2006 | Pixley et al. ................... 221/9 |
| 7,123,989 B2 | 10/2006 | Pinney et al. |
| 7,194,333 B2 * | 3/2007 | Shoenfeld ................... 700/243 |
| 7,228,200 B2 * | 6/2007 | Baker et al. ................. 700/236 |
| 7,264,136 B2 * | 9/2007 | Willoughby et al. ........... 221/3 |
| 7,451,015 B2 | 11/2008 | Mazur et al |
| 7,490,054 B2 | 2/2009 | Reade et al. |
| 2002/0139810 A1 | 10/2002 | Yuyama et al. |
| 2002/0166787 A1 | 11/2002 | Linton |
| 2003/0029882 A1 | 2/2003 | Yuyama et al. |
| 2004/0113786 A1 | 6/2004 | Maloney |
| 2004/0164146 A1 | 8/2004 | Rosenblum |
| 2004/0215369 A1 | 10/2004 | Rosenblum |
| 2005/0049746 A1 | 3/2005 | Rosenblum |
| 2005/0192705 A1 | 9/2005 | Pinney et al. |
| 2006/0265102 A1 * | 11/2006 | Bain ........................ 700/237 |
| 2007/0162183 A1 | 7/2007 | Pinney et al. |

FOREIGN PATENT DOCUMENTS

| | | |
|---|---|---|
| WO | WO 02/21402 | 3/2002 |
| WO | WO 2004/021289 | 3/2004 |

WO  WO-2005/005266  1/2005

OTHER PUBLICATIONS

Pyxis Helpmate® SP product literature; published or in public use at least as early as Jun. 30, 2002; 2 pages.
Pyxis Medstation® 2000 product literature; published or in public use at least as early as Jun. 30, 2002; 1 page.
Pyxis Medstation® 3000 product literature; published or in public use at least as early as Jun. 30, 2002; 1 page.
Pyxis Supplystation® product literature; published or in public use at least as early as Jun. 30, 2002; 4 pages.
Scriptpro® Pharmacy Automation SP 100™ Robotic Prescription Dispensing System product literature; published or in public use at least as early as Jun. 30, 2002; 2 pages.
Scriptpro® Pharmacy Automation SP 200® Robotic Prescription Dispensing System product literature; published or in public use at least as early as Jun. 30, 2002; 2 pages.
Scriptpro® Pharmacy Automation SP Central® Pharmacy Dispensing Management System product literature; published or in public use at least as early as Jun. 30, 2002; 1 page.
Scriptpro® Pharmacy Automation SP Station® product literature; published or in public use at least as early as Jun. 30, 2002; 2 pages.
Scriptpro® Pharmacy Automation SP Automation Center™ (SPace™) product literature; published or in public use at least as early as Jun. 30, 2002; 2 pages.
Scriptpro® Pharmacy Automation SP Unit Dispenser® (SPUD™) Robotic Pharmaceutical Dispensing System product literature; published or in public use at least as early as Jun. 30, 2002; 2 pages.
McKesson ACCU MED™ powered by AUTO LINK™ product literature; published or in public use at least as early as Jun. 30, 2002; 2 pages.
McKesson ACCU SCRIPT™ Pharmacy Robot product literature; published or in public use at least as early as Jun. 30, 2002; 2 pages.
McKesson BAKER CASSETTES™ product literature; published or in public use at least as early as Jun. 30, 2002; 1 page.
McKesson BAKER CELLS™ product literature; published or in public use at least as early as Jun. 30, 2002; 1 page.
McKesson MEDCAROUSEL™ product literature; published or in public use at least as early as Jun. 30, 2002; 2 pages.
McKesson Automated Will Call product literature; published or in public use at least as early as Jun. 30, 2002; 1 page.
NCR INSTYMEDS Prescription Medication Dispenser product literature; published or in public use at least as early as Jun. 30, 2002; 8 pages.
NCR FASTLANE™-The Self-Checkout Solution product literature; published or in public use at least as early as Jun. 30, 2002; 8 pages.
AUTOMED™ Technologies ADDS (Automatic Drug Dispensing System) product literature; published or in public use at least as early as Jun. 30, 2002; 1 page.
AUTOMED™ Technologies ATC™ Profile System product literature; published or in public use at least as early as Jun. 30, 2002; 2 pages.
AUTOMED™ Technologies AUTOMED EFFICIENCY PHARMACY™ product literature; published or in public use at least as early as Jun. 30, 2002; 6 pages.
AUTOMED™ Technologies FASTFILL™ System product literature; published or in public use at least as early as Jun. 30, 2002; 2 pages.
AUTOMED® FASTPAK™ 71 System product literature; published or in public use at least as early as Jun. 30, 2002; 2 pages.
AUTOMED® FASTPAK™ 330 and 520 product literature; published or in public use at least as early as Jun. 30, 2002; 4 pages.
AUTOMED® FASTPAK™ Tabletop System product literature; published or in public use at least as early as Jun. 30, 2002; 2 pages.
AUTOMED™ Technologies Optifill-II System product literature; published or in public use at least as early as Jun. 30, 2002; 4 pages.
AUTOMED™ Technologies Quickfill product literature; published or in public use at least as early as Jun. 30, 2002; 1 page.
AUTOMED™ Technologies Quickfill Plus product literature; published or in public use at least as early as Jun. 30, 2002; 1 page.
AUTOMED EFFICIENCY PHARMACY™ R400 product literature; published or in public use at least as early as Jun. 30, 2002; 2 pages.
AUTOMED EFFICIENCY PHARMACY™ R600 product literature; published or in public use at least as early as Jun. 30, 2002; 2 pages.
AUTOMED EFFICIENCY PHARMACY™ R800 product literature; published or in public use at least as early as Jun. 30, 2002; 2 pages.
AUTOMED EFFICIENCY PHARMACY™ R1000 product literature; published or in public use at least as early as Jun. 30, 2002; 2 pages.
GSL Solutions Will-Call Storage Systems product literature; published or in public use at least as early as Jun. 30, 2002; 4 pages.
Innovation Associates PharmASSIST Robotic Dispensing Systems (RDS-I and RDS-II) product literature; published or in public use at least as early as Jun. 30, 2002; 2 pages.
Innovation Associates SmartCabinet System product literature; published or in public use at least as early as Jun. 30, 2002; 2 pages.
MedVantx Point-of-Care Automated Sample System product literature; published or in public use at least as early as Jun. 30, 2002; 1 page.
Parata Systems Parata RDS product literature; published or in public use at least as early as Jun. 30, 2002; 3 pages.
PICKPOINT™ FLEXRX™ Pharmacy Dispensing product literature; published or in public use at least as early as Jun. 30, 2002; 6 pages.
Foundation Systems Automated Prescription Point-of-Delivery Kiosk System product literature; published or in public use at least as early as Jun. 30, 2002; 1 page.
Mendota Healthcare, Inc. Business Plan; Dec. 1, 2001; 36 pages.
Mendota Healthcare, Inc. Executive Summary; copyright 2001; 7 pages.
Rowland, Christopher; Drug Vending Units Worry Pharmacists; Jul. 3, 2004; 3 pages.
Declaration of Walter Bain including Exhibit A; executed Sep. 2004; 6 pages.
Declaration of Daniel Bain; executed Sep. 2004; 2 pages.
Letter from Daniel T. Jones; dated May 15, 2001; 1 page.
International Search Report and Written Opinion of the International Searching Authority for PCT/US05/43243 dated Feb. 23, 2007.
"Time to switch drugstores?", Consumer Reports, Oct. 2003, 5 pgs.
"Docs try ATM-style prescription machines", CNN.com, Nov. 17, 2001, 2 pgs.
"Vending Pharmacy—Is the long-distance dispensing of drugs the remedy for patients in remote areas?", Drugtopics.com, Mar. 6, 2000, 3 pgs.
"Chains, independents make some gains in technology", Drugtopics.com, Dec. 10, 2001, 3 pgs.
Fleming, Harris, Jr., "Orderly Process—Can central prescription filling help solve pharmacy's time crunch? McKesson thinks it can", Drugtopics.com, Mar. 1, 1999, 3 pgs.
Mendota Healthcare, Inc.'s profile of "InstyMeds" available at www.instymed.com/video.html, 12 pgs.
Jackman, Michael, "Study says chain drug stores ripe for kiosks", KioskMarketPlace.com, Aug. 1, 2001, 2 pgs.
Kieser, Joe, "Medication available at punch of a button", Sun Newspapers, Oct. 31, 2001, 2 pgs.
Mentroy, Jill S., MD, FACS, "Telepharmacy: VA Pharmacy finds Convenience in Vending Machines", Veterans Health System Journal (VHSJ), Oct. 6, 1998, 2 pgs.
Pickpoint Corporation's profile of "FlexCall product" available at http://www.pickpoint.com/prodcuts-flexcall.html, 23 pgs.
Telepharmacy Solutions, Inc. profile of "TSI's ADDS (Automated Drug Distribution System) product" available at http://www.telepharmacysolutions.com/, 44 pgs.
Ukens, Carol, "Remote Control—Automation puts retail R.Ph.'s foot in doctor's door", Drugtopics.com, Jan. 20, 1997, 1997, 3 pgs.
Ukens, Carol, "Another automated dispenser hits community pharmacy", Drugtopics.com, Sep. 15, 1997, 1997. 3 pgs.
Ukens, Carol, "Pharmacist Shortage Boosts Telepharmacy", Telepharmacy Solutions Media Coverage, Jun. 3, 2002, 2 pgs.

Ukens, Carol, "Technology—Rx vending machine targets pharmacy", Drugtopics.com, Dec. 10, 2001, 3 pgs.
K. Barker et al, "White Paper on Automation in Pharmacy", The Consultant Pharmacists, vol. 13, No. 13, Mar. 1998, pp. 21-37.
McKesson APS: Automated Will Call Rotary Cabinet, available at http://www.mckessonaps.com/wt/aps/prodserv_profiles_willcall.
R. Lewis at al, "Developing the Infrastructure for Patient Care", The Patient-Centered Pharmacy, APhA, 2002, pp. 66-94.
CBS NEWS, "Automated Medicine", Nov. 13. 2001, available at http://www.cbsnews.com/storeis/2001/11/13/health/printable317894.shtml.
Supplementary Search Report for corresponding European Application No. 04756405.9 dated June 22, 2006 (3 pgs.).
Express Scripts company literature; published or in public use at least as early as Jun. 30, 2002; 2 pgs.
PYXIS HELPMATE® SP product literature; published or in public use at least as early as Jun. 30, 2002; 2 pgs.
PYXIS MEDSTATION® 2000 product literature; published or in public use at least as early as Jun. 30, 2002; 1 pg.
PYXIS MEDSTATION®3000 product literature; published or in public use at least as early as Jun. 30, 2002; 1 pg.
PYXIS SUPPLYSTATION® product literature; published or in public use at least as early as Jun. 30, 2002; 4 pgs.
SCRIPTPRO®Pharmacy Automation SP 100™ Robotic Prescription Dispensing System product literature; published or in publich use at least as early as Jun. 30, 2002; 2 pgs.
SCRIPTO® Pharmacy Automation SP 200® Robotic Prescription Dispensing System product literature; published or in publich use at least as early as Jun. 30, 2002; 2 pgs.
SCRIPTPRO® Pharmacy Automation SP Central® Pharmacy Dispensing Management System product literature; published or in public use at least as early as Jun. 30, 2002; 1 pg.
SCRIPTPRO® Pharmacy Automation SP Station® product literature; published or in public use as least as early as Jun. 30, 2002; 2 pgs.
SCRIPTPRO® Pharmacy Automation SP Automation Center™ (SPace™) product literature; published or in public use at least as early as Jun. 30, 2002; 2 pgs.
SCRIPTPRO® Pharmacy Automation SP Unit Dispenser® (SPUD®) Robotic Pharmaceutical Dispensing System product literature; published or in public use at least as early s Jun. 30, 2002; 2 pgs.
McKesson ACCU MED™ powered by AUTO LINK™ product literature; published or in public use at least as early as Jun. 30, 2002; 2 pgs.
McKesson ACCU SCRIPT™ Pharmacy Robot product literature; published or in public use at least as early as Jun. 30, 2002; 2 pgs.
McKesson BAKER CASSETTES™ product literature; published or in public use at least as early as Jun. 30,2002; 1 pg.
McKesson BAKER CELLS™ product literature; published or in public use at least as early as Jun. 30, 2002; 1 pg.
McKesson MEDCAROUSEL™ product literature; published or in public us at least as early as Jun. 30, 2002; 2 pgs.
McKesson Automated Will Call product literature; published or in public use at least as early as Jun. 30, 2002; 1 pg.
NCR INSTYMEDS Prescription Medication Dispenser product literature; published or in public use at least as early as Jun. 30, 2002; 8 pgs.
NCR FASTLANE™ The Self-Checkout Solution product literature; published or in public use at least as early as Jun. 30, 2002; 8 pgs.
AUTOMED™ Technologies ADDS (Automatic Drug Dispensing System) product literature; published or in public use at least as early as Jun. 30, 2002; 1 pg.
AUTOMED™ Technologies ATC™ Profile System product literature; published or in public use at least as early as Jun. 30, 2002; 2 pgs.
AUTOMED™ Technologies AUTOMED EFFICIENCY PHARMACY™ product literature; published or in public use at least as early as Jun. 30, 2002; 6 pgs.
AUTOMED™ Technologies FASTFILL™ System product literature; published or in public use at least as early as Jun. 30, 2002; 2 pgs.
AUTOMED® FASTPAK™ 71 System product literature; published or in public use at least as early as Jun. 30, 2002; 2 pgs.
AUTOMED® FASTPAK™ 330 and 520 product literature; published or in public use at least as early as Jun. 30, 2002; 4 pgs.
AUTOMED® FASTPAK™ Tabletop System product literature; published or in public use at least as early as Jun. 30, 2002; 2 pgs.
AUTOMED™ Technologies Optifill-II System product literature; published or in public use at least as early as Jun. 30, 2002; 4 pgs.
AUTOMED™ Technologies Quickfill product literature; published or in public use at least as early as Jun. 30, 2002; 1 pg.
AUTOMED™ Technologies Quickfill Plus product literature; published or in public use at least as early as Jun. 30, 2002; 1 pg.
AUTOMED EFFICIENCY PHARMACY™R400 product literature; published or in public use at least as early as Jun. 30, 2002; 2 pgs.
AUTOMED EFFICIENY PHARMACY™ R600 product literature; published or in public use at least as early as Jun. 30, 2002; 2 pgs.
AUTOMED EFFICIENY PHARMACY™ R800 product literature; published or in public use at least as early as Jun. 30, 2002; 2 pgs.
AUTOMED EFFICIENY PHARMACY™ R1000 product literature; published or in public use at least as early as Jun. 30, 2002; 2 pgs.
GSL Solutions Will-Call Storage Systems product literature; published or in public use at least as early as Jun. 30, 2002; 4 pgs.
Innovation Associates PharmASSIST Robotic Dispensing Systems (RDS-1 and RDS-II) product literature; published or in public use at least as early as Jun. 30, 2002; 2 pgs.
Innovation Associates SmartCabinet System product literature; published or in public use at least as early as Jun. 30, 2002; 2 pgs.
MedVantx Point-of-Care Automated Sample System product literature; published or in public use at least as early as Jun. 30, 2002; 1 pg.
Parata Systems Parata RDS product literature; published or in public use at least as early as Jun. 30, 2002; 3 pgs.
PICKPOINT™ FLEXRX™ Pharmacy Dispensing product literature; published or in public use at least as early as Jun. 30, 2002; 1 pg.
Foundation Systems Automated Prescription Point-of-Delivery Kiosk System product literature; published or in public use at least as early as Jun. 30, 2002; 1 pg.
Mendota Healthcare, Inc. Business Plan; Dec. 1, 2001; 36 pgs.
Mendota Healthcare, Inc. Executive Summary; copyright 2001; 7 pgs.
Rowland, Christopher; Drug Vending Units Worry Pharmacists; 3, 2004; 3 pgs.
Declaration of Walter Bain including Exhibit A; executed Sep. 2004; 6 pgs.
Declaration of Daniel Bain; executed Sep. 2004; 2 pgs.
Letter from Daniel T. Jones; dated May 15, 2001; 1 pg.
Official Action dated May 23, 2007 for U.S. Appl. No. 11/688,189.
Response as filed on Aug. 23, 2007 for U.S. Appl. No. 11/688,189.
Official Action dated Jan. 9, 2007 for U.S. Appl. No. 11/001,110.
International Search Report and Written Opinion of the International Searching Authority for PCT/US05/43243 dated Feb. 23, 2007.
Supplementary Search Report for corresponding European Application No. 04756405.9 dated Jun. 22, 2006 (3 pgs.).
Telepharmacy Solutions, Inc. profile of "TSI's ADDS (Automated Drug Distribution System) product" available at http://www.telepharmacysolutions.com/, 44 pgs.
Ukens, Carol, "Remote Control—Automation puts retail R.Ph.'s foot in doctor's door", Drugtopics.com, Jan. 20, 1997, 3 pgs.
Ukens, Carol, "Another automated dispenser hits community pharmacy", Drugtopics.com, Sep. 15, 1997, 3 pgs.
Ukens, Carol, "Pharmacist Shortage Boosts Telepharmacy", Telepharmacy Solutions Media Coverage, Jun. 3, 2002, 2 pgs.
Ukens, Carol, "Technology—Rx vending machine targets pharmacy", Drugtopics.com, Dec. 10, 2001, 3 pgs.
K. Barker et al, "White Paper on Automation in Pharmacy", The Consultant Pharmacists, vol. 13, No. 13, Mar. 1998, pp. 21-37.
McKesson APS: Automated Will Call Rotary Cabinet, available at http://www.mckessonaps.com/wt/aps/prodserv_profiles_willcall.
R. Lewis et al, "Developing the Infrastructure for Patient Care", The Patient-Centered Pharmacy, APhA, 2002, pp. 66-94.
CBS News, "Automated Medicine", Nov. 13, 2001, available at http://www.cbsnews.com/storeis/2001/11/13/health/printable317894.shtml.
"Time to switch drugstores?", Consumer Reports, Oct. 2003, 5 pgs.
"Docs try ATM-style prescription machines", CNN.com, Nov. 17, 2001, 2 pgs.

"Vending Pharmacy—Is the long-distance dispensing of drugs the remedy for patients in remote areas?", Drugtopics.com, Mar. 6, 2000, 3 pgs.

"Chains, independents make some gains in technology", Drugtopics.com, Dec. 10, 2001, 3 pgs.

Fleming, Harris, Jr., "Orderly Process—Can central prescription filling help solve pharmacy's time crunch? McKesson thinks it can", Drugtopics.com, Mar. 1, 1999, 3 pgs.

Mendota Healthcare, Inc.'s profile of "InstyMeds" available at www.instymed.com/video.html, 12 pgs.

Jackman, Michael, "Study says chain drug stores ripe for kiosks", KioskMarketPlace.com, Aug. 1, 2001, 2 pgs.

Kieser, Joe, "Medication available at punch of a button", Sun Newspapers, Oct. 31, 2001, 2 pgs.

Mentroy, Jill S., MD, FACS, "Telepharmacy: VA Pharmacy finds Convenience in Vending Machines", Veterans Health System Journal (VHSJ), Oct. 6, 1998, 2 pgs.

Pickpoint Corporation's profile of "FlexCall product" available at http://www.pickpoint.com/prodcuts-flexcall.html, 23 pgs.

Non-Final Office Action dated Dec. 22, 2008 for U.S. Appl. No. 11/688,189, filed Mar. 19, 2007 (11 pgs.).

Pending claims for U.S. Appl. No. 11/688,189, filed Mar. 19, 2007 (8 pgs.).

Extended European Search Report for EP Application No. 05825427.7.

* cited by examiner

COMMUNICATION NETWORK FOR USE IN AUTOMATICALLY DELIVERING PRESCRIPTIONS

RELATED APPLICATIONS

This patent application is a continuation of U.S. patent application Ser. No. 11/001,110 filed on Nov. 30, 2004 now abandoned which is a continuation-in-part of U.S. patent application Ser. No. 10/880,269, filed on Jun. 29, 2004, now abandoned which claims the benefit of prior filed U.S. Provisional Patent Application Nos. 60/484,544 filed on Jul. 1, 2003 and 60/576,005 filed on Jun. 1, 2004, which is a continuation application of U.S. patent application Ser. No. 10/801,321, filed on Mar. 16, 2004, now U.S. Pat. No. 7,123,989 which claims the benefit of prior filed U.S. Provisional Patent Application No. 60/484,544 filed on Jul. 1, 2003. The entire disclosures of these applications are considered as being part of the accompanying applications, and are incorporated by reference herein.

FIELD OF THE INVENTION

The present invention relates generally to dispensing units for dispensing items to individuals and, more particularly, to automated or computer-controlled dispensing units.

BACKGROUND OF THE INVENTION

The typical pharmaceutical transaction entails a doctor ordering a prescription for a patient, the prescription being delivered to or filled at a pharmacy, and the patient/customer picking up the finished prescription from the pharmacy.

The typical transaction requires face-to-face interaction between the patient/customer and an available pharmacist, technician, or clerk in order to receive or pick up the finished or filled prescription. In conventional settings, a customer may be required to wait in line to drop off and/or pick up a finished prescription. Further, when the customer can pick up the prescription may be constrained by the hours that a particular pharmacy is open for business. This may result in lost potential sales to a retail establishment in which a pharmacy is located because the customer may cancel a trip to the retail establishment that they otherwise might have made had the pharmacy been open. This may also result in a delay for the customer to pick up time-sensitive prescriptions. A device that allows a customer to pick up a finished prescription without face-to-face contact with pharmacy staff would be welcomed by customers in need of finished prescriptions and the pharmacies serving them.

SUMMARY OF THE INVENTION

The present invention provides, in one aspect, a random access and random load dispensing unit including a housing, at least one support located in the housing and defining a first axis, a plurality of platforms movable along the support along the first axis, a plurality of bins supported on the platforms, the bins being movable with the platforms, and a shuttle assembly movable along the first axis and further movable along a second axis substantially perpendicular to the first axis between the plurality of platforms to access and retrieve products stored in the bins.

The present invention provides, in another aspect, a random access and random load dispensing unit including a housing, a shuttle assembly movable in the housing to access and retrieve products stored in random locations in the housing, an access door pivotably coupled to the housing, and a plurality of customer interface components coupled to the access door. At least one of the customer interface components is configured to determine an identity of a customer. The dispensing unit also includes a computer in communication with the customer interface components. The computer is able to match the customer with at least one of the products stored in the random locations in the housing. The dispensing unit further includes a controller in communication with the computer for operating the shuttle assembly. The shuttle assembly is directed to the location in the housing to retrieve the at least one product for the customer.

The present invention provides, in yet another aspect, a random access and random load dispensing unit including a housing, an access door pivotably coupled to the housing, and a plurality of customer interface components coupled to the access door. At least one of the customer interface components is configured to determine an identity of a customer. The dispensing unit also includes at least one substantially vertically-oriented support defining a first axis and located in the housing, a plurality of platforms movable along the first axis and coupled to the support, and a plurality of bins supported on the platforms. The bins are movable with the platforms to selectively allow only the bins on one of the plurality of platforms to be accessed at a given time. The dispensing unit further includes a shuttle assembly movable along the first axis. The shuttle assembly is further movable along a second axis and a third axis coplanar with the second axis. The second and third axes are substantially perpendicular to the first axis and to each other. The shuttle assembly is movable along the second and third axes between the plurality of platforms to access and retrieve products stored in the bins. The dispensing unit also includes a computer in communication with the customer interface components. The computer is able to match a particular product previously specified for the customer with a random location in the housing in which the particular product is stored. The dispensing unit further includes a controller in communication with the computer for operating the shuttle assembly. The shuttle assembly is directed to the random location in the housing to retrieve the specific product for the customer. The dispensing unit also includes a dispense bin located in the access door. The dispense bin is movable between a first position, in which the dispense bin is deployed into the housing for the shuttle assembly to deposit the product into the dispense bin, and a second position, in which the dispense bin is retracted into the access door and the product is ready to be retrieved by the customer. The dispensing unit further includes a dispense bin lid selectively covering the dispense bin. The dispense bin lid is movable between a first position, in which the product in the dispense bin is inaccessible by the customer, and a second position, in which the product in the dispense bin is accessible by the customer for removal.

The present invention provides, in a further aspect, a container for use with a vending apparatus configured to dispense pharmaceuticals, whereby the vending apparatus utilizes an automated picker assembly to retrieve the container. The container includes a receptacle containing the pharmaceuticals, and a substantially rigid header coupled to the receptacle. The header includes opposite end portions extending beyond an outer periphery of the receptacle, two apertures through the header, and a barcode label coupled to the header.

The present invention provides, in another aspect, a container for use with a vending apparatus configured to dispense pharmaceuticals. The vending apparatus utilizes an automated picker assembly to retrieve the container. The container includes a receptacle having an open end to deposit therein the pharmaceuticals, and two opposing side walls defining in part the open end. The container also includes a header having an insertion portion insertable into the open end of the receptacle between the opposing side walls, opposite end portions extending beyond an outer periphery of the receptacle, and two apertures through the header, the apertures each defining a shape having an apex. The container further includes a label having a barcode printed thereon. A first portion of the label is coupled to one of the side walls of the receptacle and to one side of the header. A second portion of the label extends beyond an outer periphery of the header. The second portion of the label is configured to couple to a second side of the header and the other side wall of the receptacle to at least partially close the open end of the receptacle.

The invention also provides a method of managing an item in a dispensing unit that includes a controller, a picker assembly, and a plurality of trays. Each of the trays has a plurality of slots. The method includes selecting a tray from the plurality of trays at the controller, and loading the item into a first slot of the selected tray. The method also includes moving the item to a second slot of another tray with the picker assembly, and at the controller, automatically updating location information relating to the second slot in which the item has been deposited.

Other features and aspects of the present invention will become apparent to those skilled in the art upon review of the following detailed description, claims and drawings.

BRIEF DESCRIPTION OF THE DRAWINGS

In the drawings, wherein like reference numerals indicate like parts.

Figure 1:
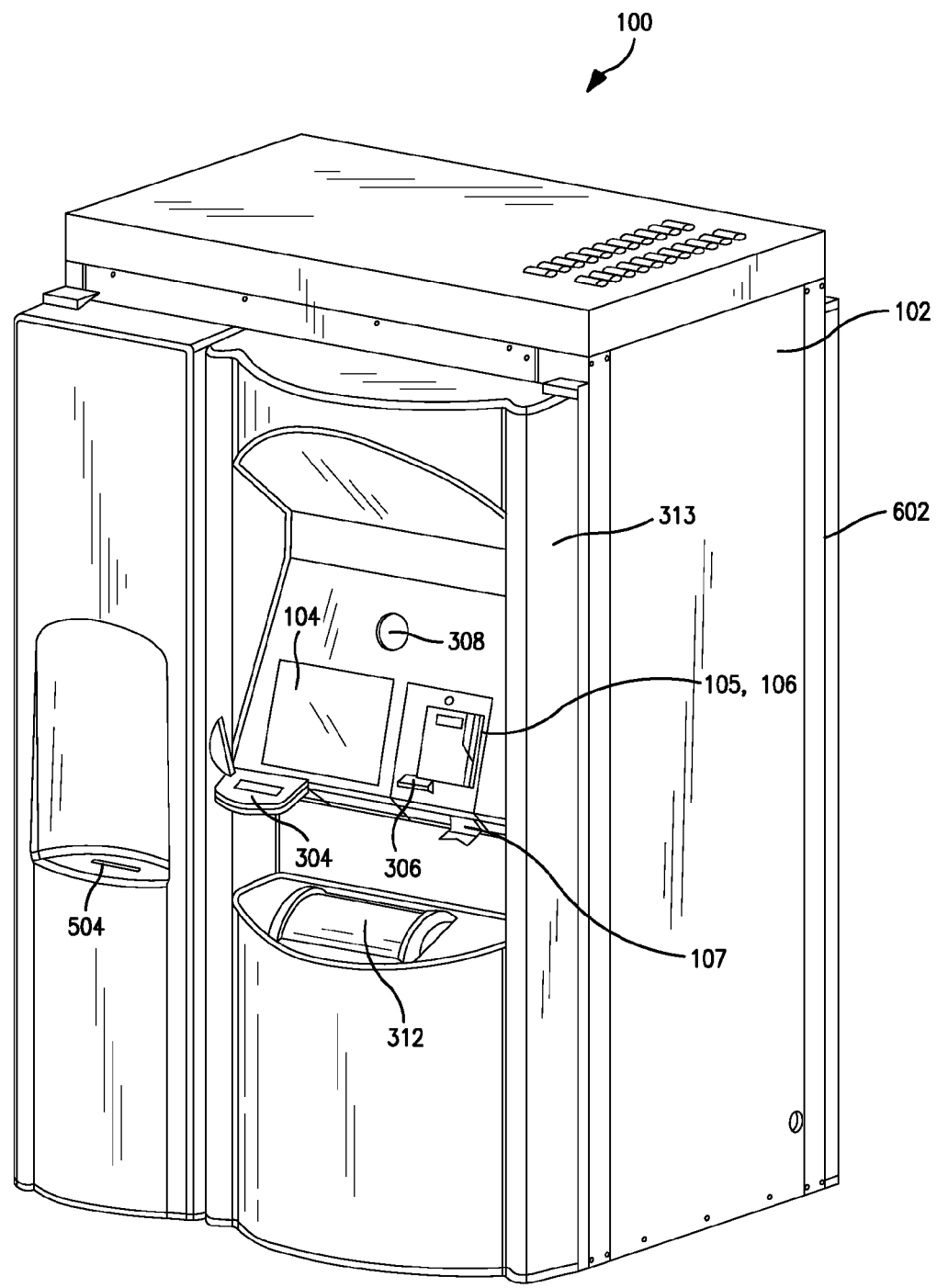
FIG. 1 is a front perspective view of a random access and random load dispensing unit of the present invention.

Before any features of the invention are explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein is for the purpose of description and should not be regarded as limiting. The use of "including", "having", and "comprising" and variations thereof herein is meant to encompass the items listed thereafter and equivalents thereof as well as additional items. The use of letters to identify elements of a method or process is simply for identification and is not meant to indicate that the elements should be performed in a particular order.

DETAILED DESCRIPTION

Figure 2:
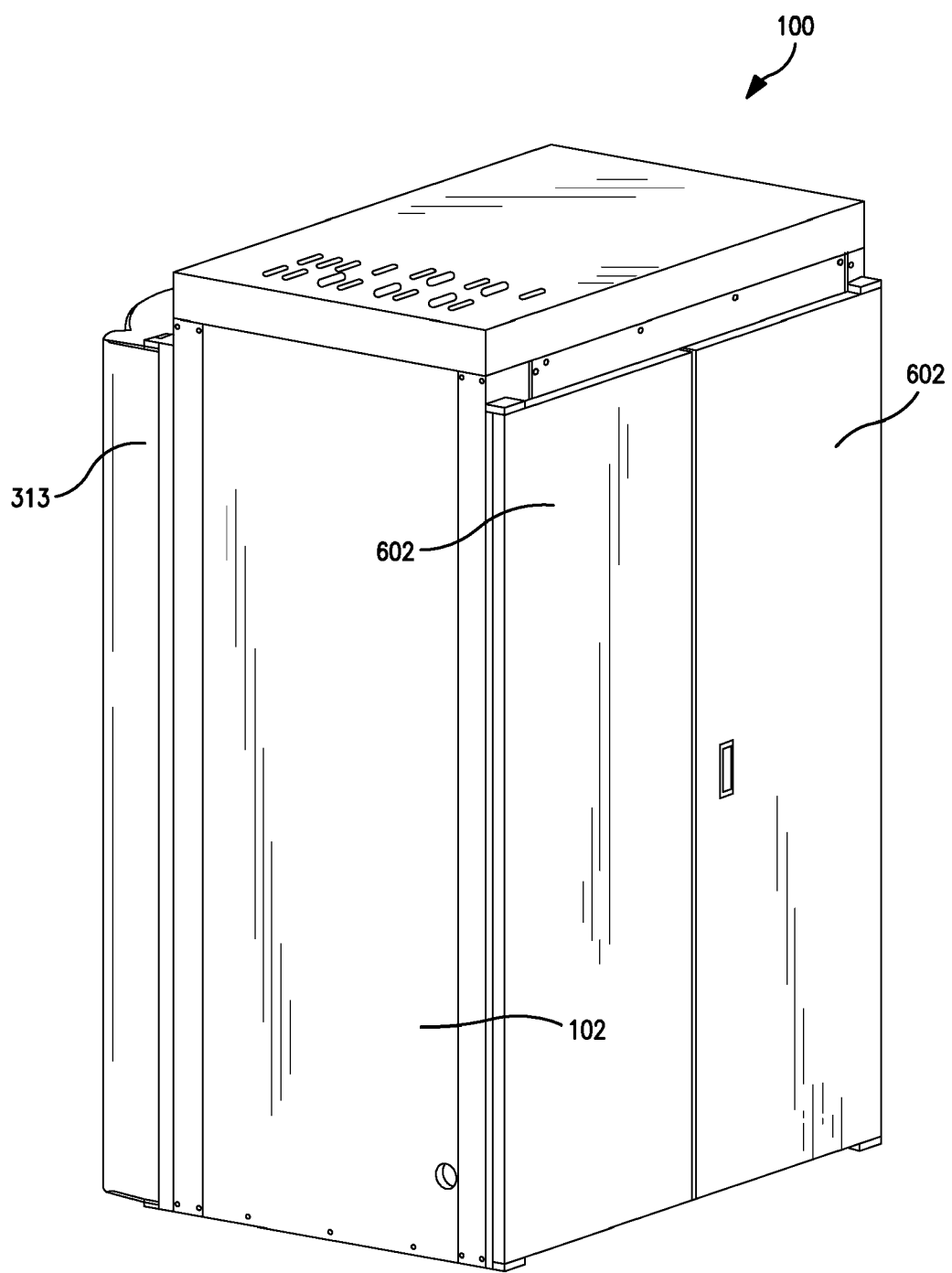
FIG. 2 is a rear perspective view of the dispensing unit of FIG. 1.

FIGS. 1 and 2 illustrate an automated random-access and random-load dispenser or dispensing unit 100 which allows customers to purchase products, particularly prescription medicines. As shown in FIG. 1, the unit 100 includes a housing 102, means to communicate with the customer (e.g., a touch screen 104, or the like), means to identify the customer (e.g., a magnetic stripe card reader 105), and means to accept payment from the customer (e.g., a cash acceptor or a credit card reader 106). The credit card reader 106 can be utilized as the magnetic stripe card reader 105 to identify the customer. The unit 100 may alternatively or additionally include other identification readers, such as a barcode scanner 107 located at the front of the unit 100. The barcode scanner 107 may work in conjunction with customer identification cards (e.g., drivers licenses, etc.) and/or store cards (e.g., prescription drug cards, pharmacy discount cards, customer loyalty cards, etc.), which typically include a barcode to identify the customer. Further, other identification readers may be utilized, such as fingerprint readers and retinal scanners, for example, to identify the customer.

The touch screen 104 can also be utilized by the customer to initiate customer login. For example, the customer can utilize the touch screen 104 to enter a user name or other identifying information, such as a prescription number. The touch screen 104 can further be utilized by the customer to verify their identity by inputting, for example, a password (e.g., a birth date, social security number, etc.) or a personal identification number. In some other embodiments, the touch screen 104 can identify a customer by prompting the customer to verify their identity by inputting, for example, a combination of identifiers such as date of birth and customer last name, date of birth and customer street address, date of birth and customer residential zip code, date of birth and customer phone number, and the like, which the customer has provided during a registration process, detailed hereinafter.

Figure 3:
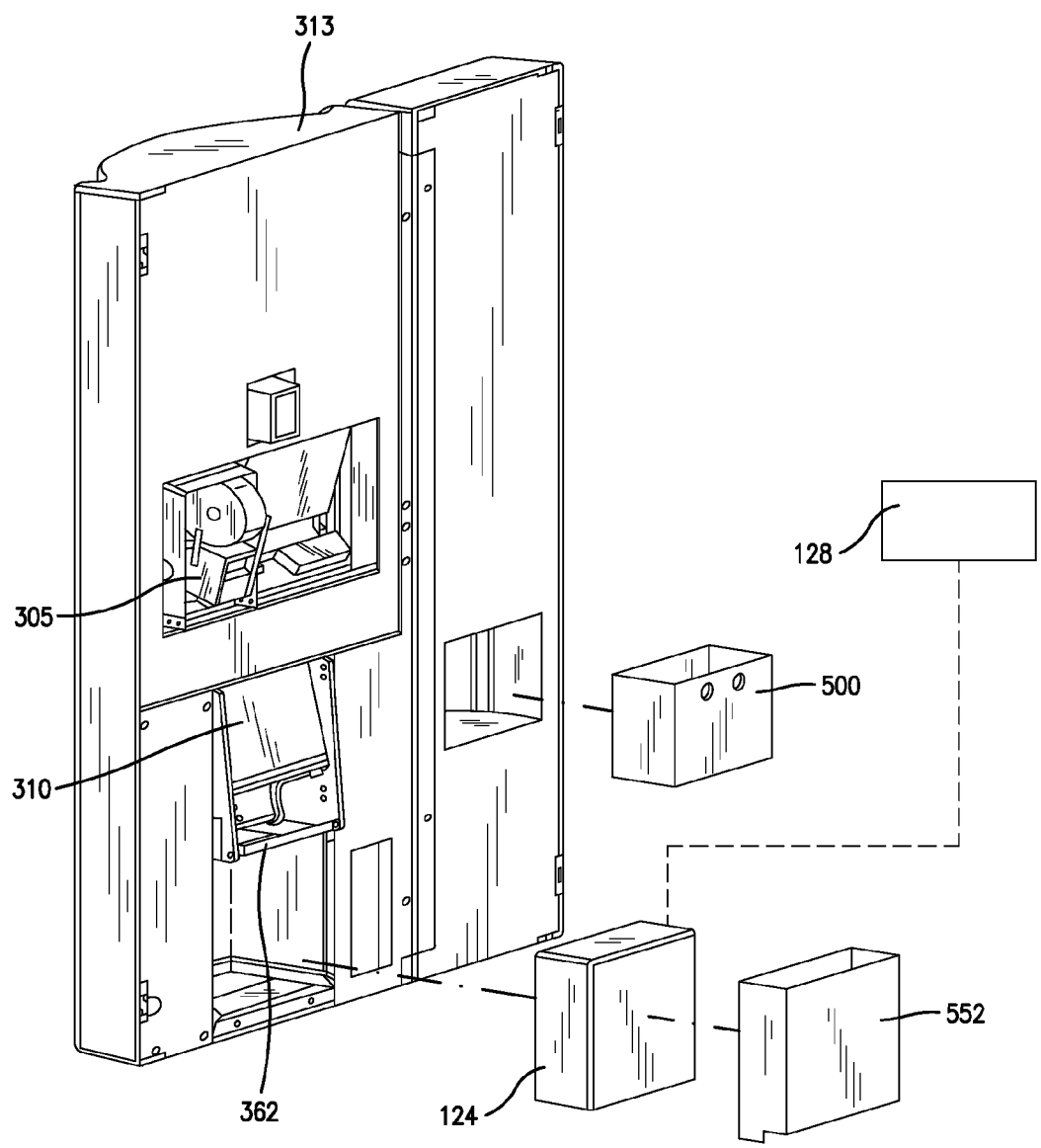
FIG. 3 is a rear perspective view of a portion of the interior of the dispensing unit of FIG. 1, illustrating a portion of the internal components of the dispensing unit.

The unit 100 may also include a signature pad 304 on which the customer may record their signature to complete a purchase. Further, the unit 100 may include a printer 305 (see FIG. 3) to output a receipt (through dispense opening 306) to the customer for a record of the purchase. The unit 100 may also include a camera 308 to monitor and/or record customers' transactions with the unit 100. After a customer completes a transaction with the unit 100, the unit 100 may dispense a finished prescription to a dispense bin 310 (see FIGS. 3-5), which is accessible by the customer through a retractable dispense bin lid 312 (see FIG. 1). The dispense bin 310 and operation thereof will be discussed in greater detail below.

Alternatively, the unit 100 may incorporate more than one touch screen 104, more than one magnetic stripe card reader 105 and/or credit card reader 106, more than one barcode scanner 107, more than one signature pad 304, more than one printer 305, more than one camera 308, and more than one dispense bin 310 to allow more than one customer to utilize the unit 100 at a given time.

Some pharmacies are required to present consumers a variety of papers, such as HIPAA privacy rights statements that also require signatures. In order to track that HIPAA privacy right statements have been signed, the pharmacies often capture the signatures of the consumers and set a flag in the respective files associated with the consumers. The unit 100 can be configured to display information such as the HIPAA privacy rights statements, and to prompt the consumer for signature before dispensing any prescriptions. Once the signature has been captured via the signature pad 304, a flag associated with the consumer is set in the unit 100 electronically.

The customer interface controls or components, including the touch screen 104, magnetic stripe card reader 105 and/or credit card reader 106, barcode scanner 107, signature pad 304, receipt dispense opening 306, camera 308, and dispense bin 310 are located on an access door 313 coupled to the housing 102. The access door 313 may be pivotably coupled to the housing 102, such that an operator may pivot the access door 313 away from the housing 102 to service the working components of the touch screen 104, magnetic stripe card reader 105 and/or credit card reader 106, barcode scanner 107, signature pad 304, receipt dispense opening 306, camera 308, and dispense bin 310.

The unit 100 may incorporate a prescription drop-off bin 500 (see FIG. 3) to allow a customer to drop off their prescription to be filled. Prescriptions may be inserted through a slot 504 in the access door 313 to be collected by the drop-off bin 500. The prescription drop-off bin 500 may be integrally formed with the access door 313. Alternatively, the prescription drop-off bin 500 may be a separate component from the access door 313 and positioned at a different location on the housing 102. A pharmacist or technician may access the drop-off bin 500 by opening the access door 313 to retrieve the prescriptions deposited in the drop-off bin 500.

The unit 100 also includes a computer 124 that is operable to interface with the touch screen 104, the credit card reader 106, the barcode scanner 107, the signature pad 304, and the receipt printer 305. The computer 124 may be physically located almost anywhere in the unit 100, however, in the illustrated construction, the computer 124 is located in the access door 313 of the unit 100. The computer 124 is shown as a component of the unit 100, but it will be understood by those of ordinary skill in the art that the computer 124 could be remote from the unit 100 and operate the unit 100 through an information connection, such as a network. Further, the computer 124 is shown as dedicated to the unit 100, but multiple units 100 could operate off the same computer 124. The unit 100 would not need its own computer 124, but instead could operate off a computer 124 housed in another unit 100 or not housed within a unit 100 at all. The housing 102 may further include a conveniently located countertop (not shown) to facilitate the customer's interaction with the unit 100.

Figure 4:
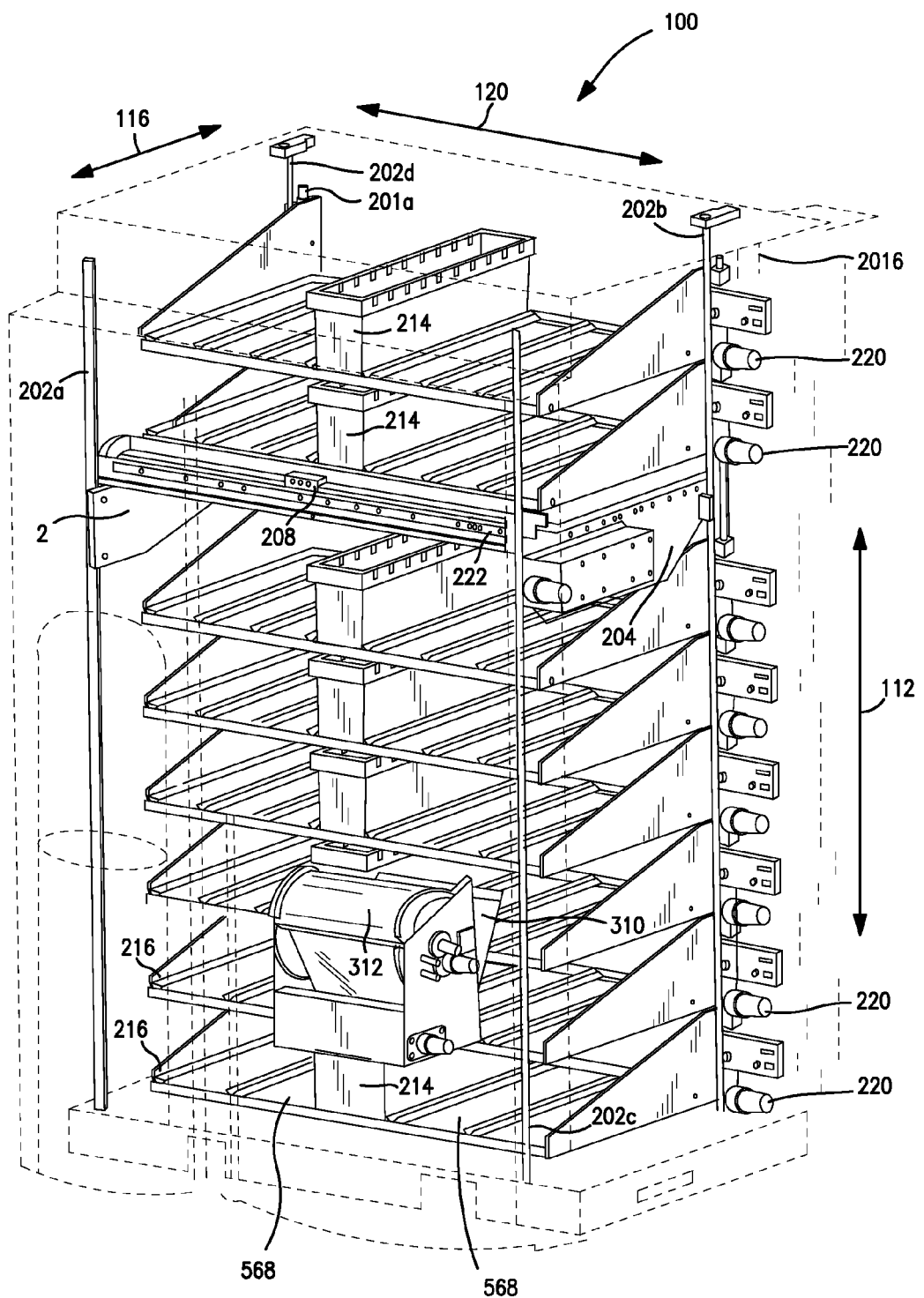
FIG. 4 is a front perspective view of a portion of the internal components of the dispensing unit of FIG. 1.
Figure 5:
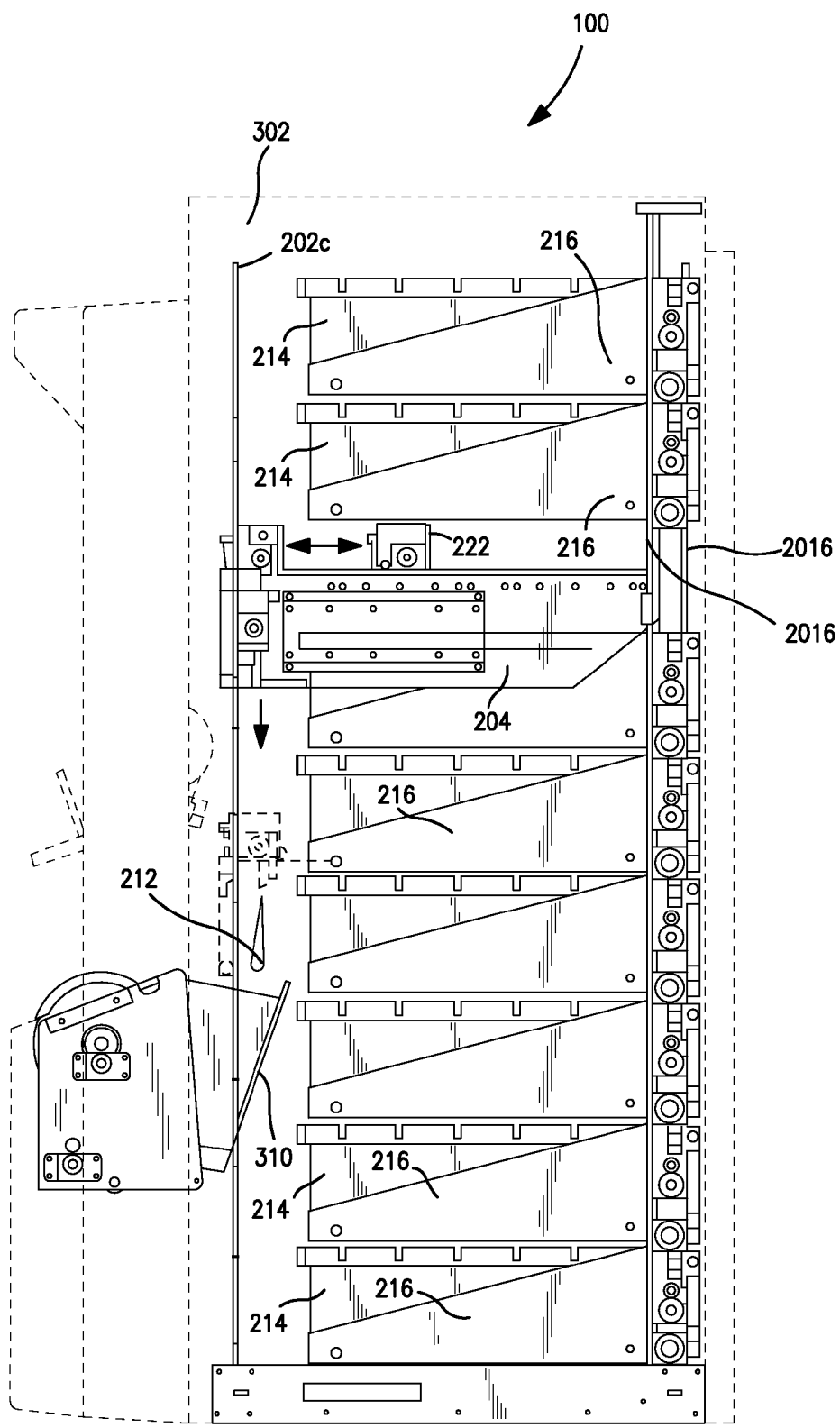
FIG. 5 is a side view of the internal components of the dispensing unit of FIG. 1.

FIGS. 4 and 5 illustrate the internal components of the unit 100. Two vertically-oriented platform support members 201*a*, 201*b* support a plurality of platforms 216, such that the platforms 216 are allowed to travel or maneuver along a vertical axis (i.e., Y-axis 112) inside the housing 102. In the illustrated construction of the unit 100, the platforms 216 are cantilevered off of the support members 201*a*, 201*b*. However, in alternative constructions of the unit 100, additional support members may be utilized to support the front portions of the platforms 216.

A plurality of vertically-oriented, or "Y-axis" support members 202*a*-202*d* support a picker or shuttle assembly 208, such that the shuttle assembly 208 is allowed to travel or maneuver along a vertical axis (i.e., Y-axis 112) inside the housing 102. In addition, an "X-axis" support 222 or a carriage (also see FIGS. 8-10) allows the shuttle assembly 208 to travel or maneuver from side to side in the housing 102 (i.e., along X-axis 120). Further, "Z-axis" supports 204 or carriage supports (see FIGS. 4, 5, and 10) allow the shuttle assembly 208 to travel or maneuver from the front of the housing 102 to the rear of the housing 102 (i.e., along Z-axis 116). The Y-axis supports 202a-202d, the X-axis support 222, and the Z-axis supports 204 combine to provide a support structure allowing the shuttle assembly 208 to travel to any defined location within the housing 102.

Figure 6:
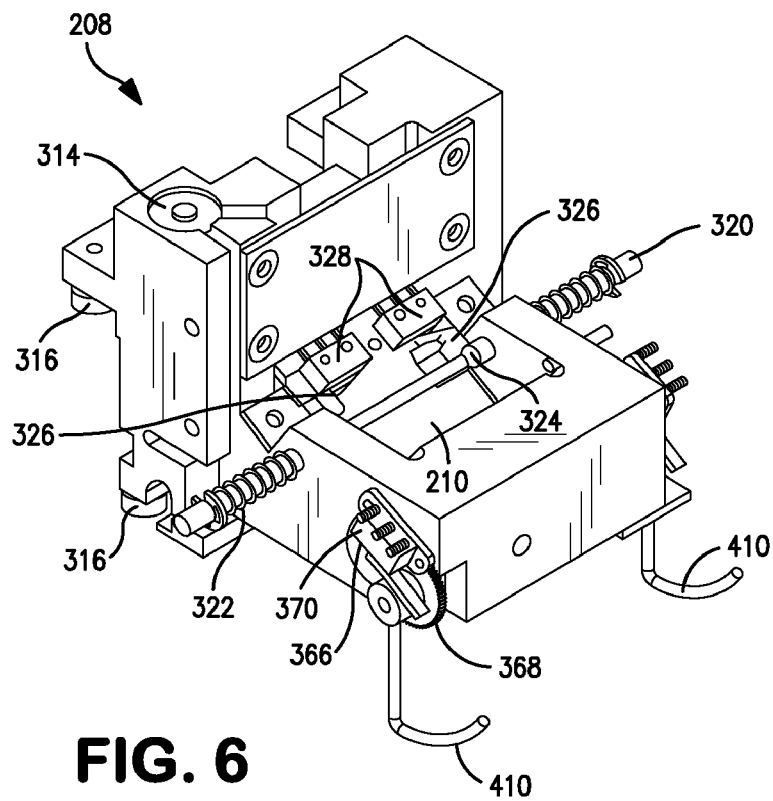
FIG. 6 is a top perspective view of a shuttle assembly of the dispensing unit of FIG. 1.
Figure 7:
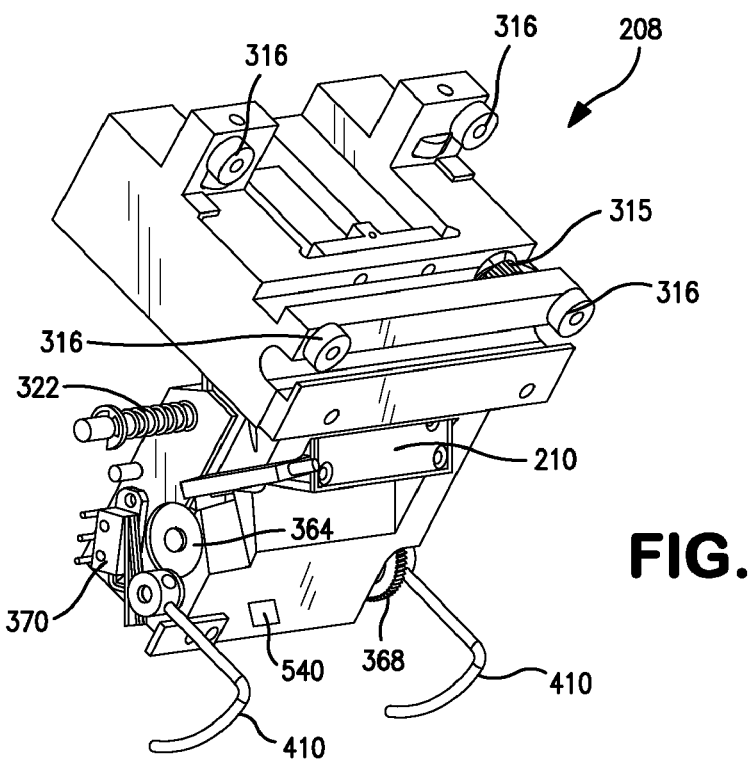
FIG. 7 is a bottom perspective view of the shuttle assembly of FIG. 6.
Figure 8:
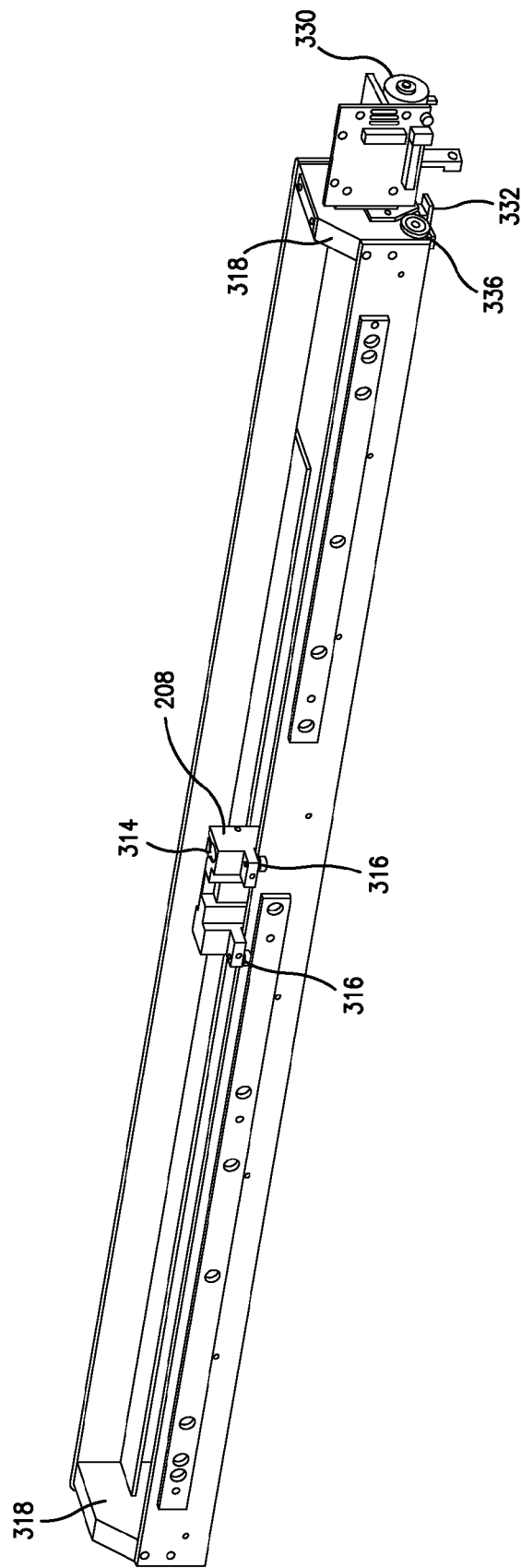
FIG. 8 is a front perspective view of a carriage and the shuttle assembly of the dispensing unit of FIG. 1.
Figure 9:
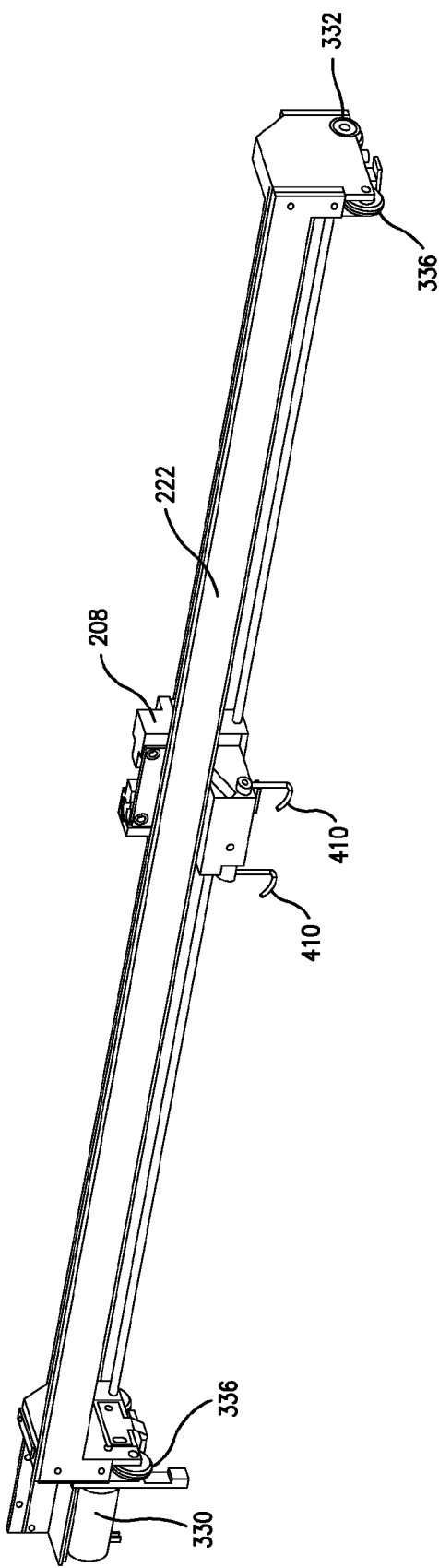
FIG. 9 is a rear perspective view of the carriage and the shuttle assembly of the dispensing unit of FIG. 1.

With reference to FIGS. 8 and 9, the X-axis support 222 is configured to receive the shuttle assembly 208. As shown in FIG. 6, the shuttle assembly 208 includes an X-axis drive motor 314 to provide movement to the shuttle assembly 208 relative to the X-axis support 222. To provide such movement, the shuttle assembly 208 may utilize a pinion 315 coupled to the X-axis drive motor 314 to drivably engage a rack (not shown) fixed to the X-axis support 222. As such, rotation of the pinion 315 may cause the shuttle assembly 208 to move from side to side in the housing 102. The X-axis drive motor 314 may interface with a controller 128, which may selectively activate the X-axis drive motor 314 when prompted by the computer 124. The shuttle assembly 208 may also include a plurality of roller bearings 316 (see also FIG. 7) to engage one or more surfaces of the X-axis support 222 to secure the shuttle assembly 208 in the X-axis support 222. Alternatively, other known drive structure may be utilized to move the shuttle assembly 208 relative to the X-axis support 222.

With reference to FIGS. 6 and 7, the shuttle assembly 208 also includes a positioning system or an "overtravel" system to detect the proximity of the shuttle assembly 208 to opposite end walls 318 of the X-axis support 222 (see FIG. 8). Such an overtravel system may interface with the controller 128 and the computer 124 to substantially prevent the shuttle assembly 208 from impacting the end walls 318 of the X-axis support 222. More particularly, as shown in FIGS. 6 and 7, the overtravel system includes an activation rod 320 slidably supported in the shuttle assembly 208. The activation rod 320 is biased toward a central position by springs 322 on opposite sides of the shuttle assembly 208. The activation rod 320 includes cam surfaces 324 that are engageable by respective followers 326 coupled to respective overtravel switches 328.

During operation, the activation rod 320 may contact one of the end walls 318 of the X-axis support 222 to move the rod 320 from its biased central position. Depending on which end wall 318 is contacted, one of the springs 322 is compressed to gently slow down the shuttle assembly 208. As the rod 320 is moved, one of the followers 326 is engaged by the corresponding cam surface 324 on the rod 320 to trigger the corresponding overtravel switch 328. Furthermore, the overtravel switches 328 interface with the controller 128 and the computer 124 to alert the computer 124 when the shuttle assembly 208 is in close proximity to one of the end walls 318 of the X-axis support 222 to de-activate or stop the X-axis drive motor 314. Alternatively, the overtravel system may be configured with non-contact switches (e.g., light switches, magnetic switches, etc.) During impact, the springs 322 also absorb at least a portion of the impact energy to substantially prevent damage to the shuttle assembly 208.

With reference to FIGS. 8 and 9, the X-axis support 222 includes a Z-axis drive motor 330. Like the X-axis drive motor 314, the Z-axis drive motor 330 may drive one or more pinions 332 via a drivetrain (not shown), such that the pinions 332 engage a rack 334 fixed to one of the Z-axis supports 204 (see FIG. 10). As such, rotation of the pinions 332 may cause the X-axis support 222 to move from the front of the housing 102 to the rear of the housing 102. The Z-axis drive motor 330 may interface with the controller 128, which may selectively activate the Z-axis drive motor 330 when prompted by the computer 124. The X-axis support 222 may also include a plurality of rollers 336 to engage one or more surfaces of the Z-axis supports 204 to facilitate substantially smooth movement of the X-axis support 222 over the Z-axis supports 204. Alternatively, other known drive structure may be utilized to move the X-axis support 222 relative to the Z-axis supports 204.

Figure 10:
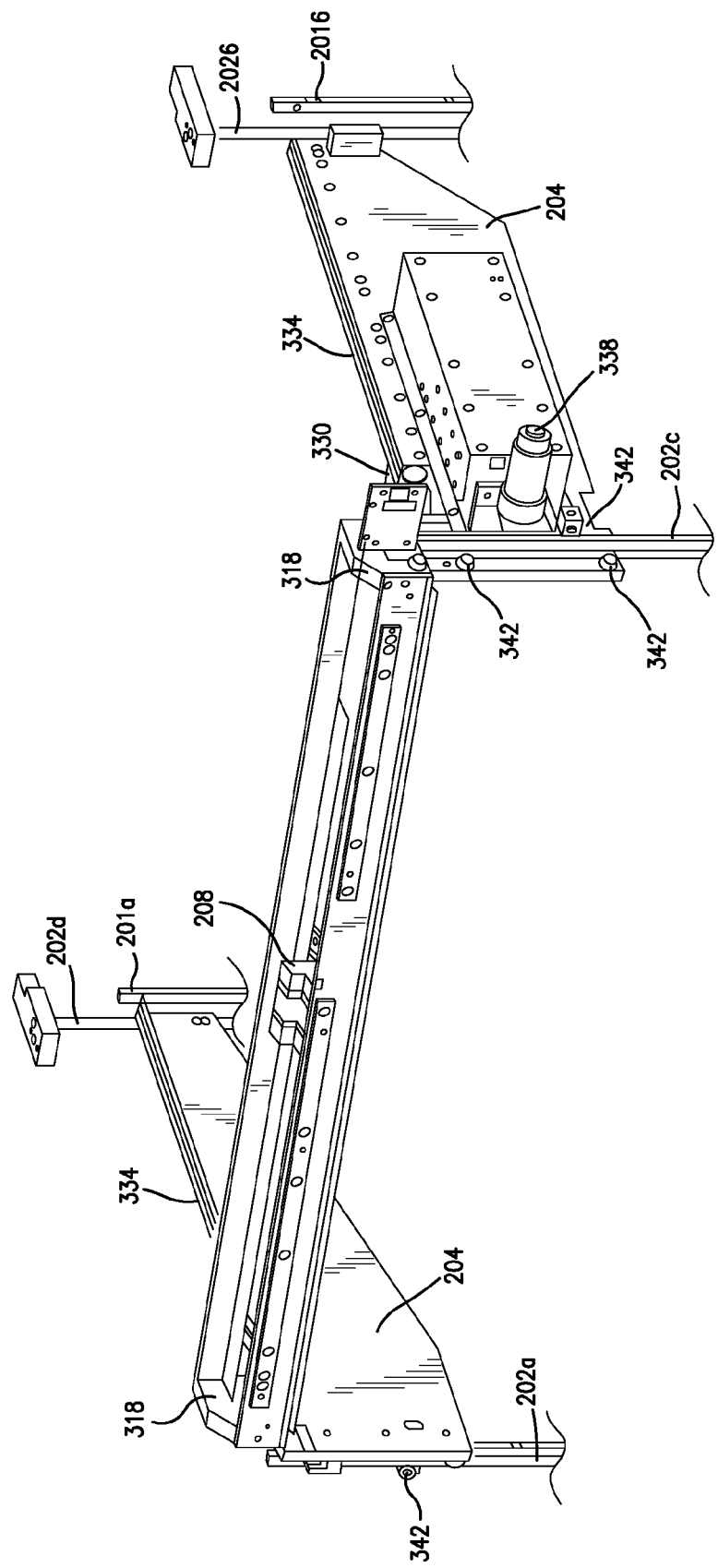
FIG. 10 is a top perspective view of the carriage and shuttle assembly of FIG. 8 supported by a Z-axis support.

With reference to FIG. 10, one of the Z-axis supports 204 includes a Y-axis drive motor 338. The Z-axis supports 204 may also be structurally interconnected by one or more cross-members (not shown) such that only one Y-axis drive motor 338 is sufficient. Alternatively, both Z-axis supports 204 may include respective Y-axis drive motors 338 that are synchronized. Like the X-axis drive motor 314 and the Z-axis drive motor 330, the Y-axis drive motor 338 may include a pinion (not shown) coupled thereto to drivably engage a rack (not shown) fixed to one of the Y-axis supports 202a-202d. Alternatively, a multiple-gear gear train may be utilized between the pinion and the rack. As such, rotation of the pinion may cause the Z-axis supports 204 to move from the top of the housing 102 to the bottom of the housing 102. The Y-axis drive motor 338 may interface with the controller 128, which may selectively activate the Y-axis drive motor 338 when prompted by the computer 124. The Z-axis supports 204 may also include a plurality of roller bearings 342 to engage one or more surfaces of the Y-axis supports 202a-202d to facilitate substantially smooth movement of the Z-axis supports 204 over the Y-axis supports 202a-202d. Alternatively, other known drive structure may be utilized to move the Z-axis supports 204 relative to the Y-axis supports 202a-202d.

Figure 17:
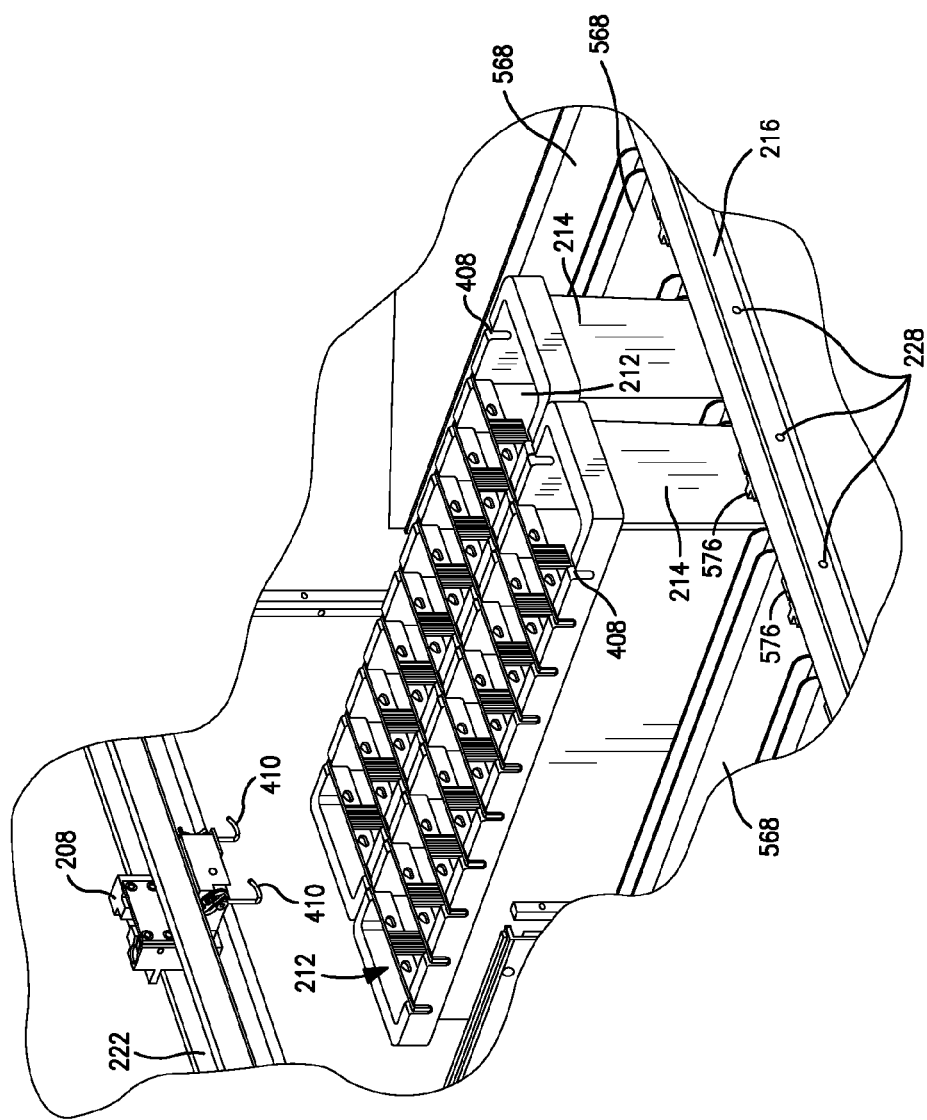
FIG. 17 is a rear perspective view of the dispensing unit of FIG. 1, illustrating a plurality of distribution trays and the shuttle assembly.
Figure 23:
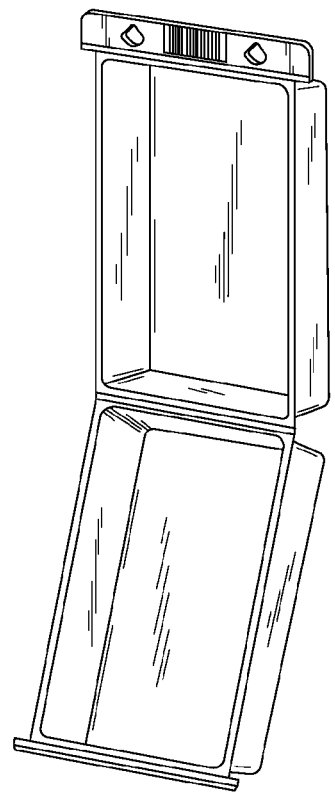
FIG. 23 is a front perspective view of yet another construction of a bag or container for storing the finished prescriptions.

As shown in FIG. 17, a plurality of prescription bags 212 are stored in a plurality of distribution bins or trays 214, which, in turn, are supported by the plurality of platforms 216. The prescription bags 212 may include one or more finished prescriptions or containers 902 (see FIGS. 18 and 20) therein for packaging the prescription drugs. Further, instead of bags 212, other types of containers (e.g., clamshell-type containers, see FIG. 23) may be stored directly in the trays 214. Like reference numerals will be used to describe like components.

Figure 21:
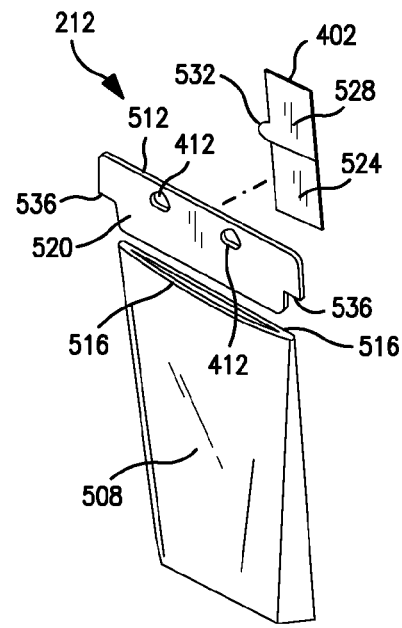
FIG. 21 is an exploded, front perspective view of another construction of a bag or container for storing the finished prescriptions.
Figure 22:
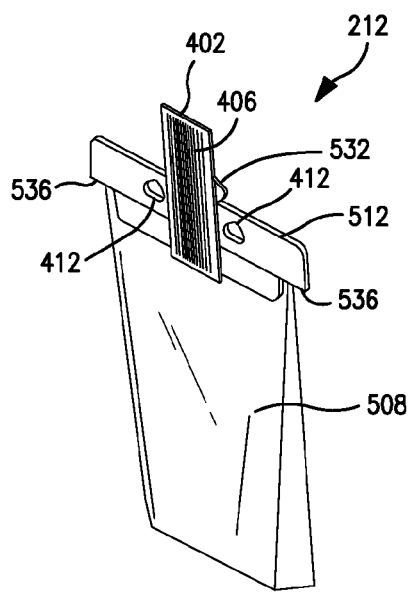
FIG. 22 is an assembled, rear perspective view of the bag or container of FIG. 21.

FIGS. 21-22 illustrate one construction of the prescription bags 212. Generally, each bag 212 includes a receptacle 508, in which the filled prescriptions or other products are positioned, and a header 512, which couples to the receptacle 508 and provides apertures 412 through which hooks 410 (described below in greater detail) of the shuttle assembly 208 are inserted to pick the prescription bag 212. In the illustrated construction, the prescription bag 212 is assembled from separate components. However, in alternate constructions of the bag 212, the receptacle 508 and the header 512 may be integrally formed with one another (e.g., in the clamshell-type container of FIG. 23).

As shown in FIG. 21, the receptacle 512 includes opposite side walls 516 defining an open end of the receptacle 508. During assembly of the bag 212, an insertion portion 520 of the header 512 is inserted into the open end of the receptacle 508. The header 512 and the receptacle 508 may be made from similar plastic materials and heat-staked or heat-sealed to one another. Then, a label 402 having a barcode 406 printed thereon is coupled to one side of the header 512 and to one of the side walls 516 of the receptacle 508 (see FIG. 22). More particularly, the label 402 includes an adhesive substance 524 on one side thereof to couple to the header 512 and the receptacle 508. A removable backing 528 is joined to a portion of the side of the label 402 having the adhesive substance 524. The backing 528 includes a tab 532 to facilitate removal of the backing 528 from the label 402. The portion of the label 402 with the backing 528 extends beyond an outer periphery of the header 512.

The assembled bag 212, as illustrated in FIG. 22, is ready to receive a filled prescription therein. After receiving a filled prescription, the backing 528 may be removed from the label 402, and the label 402 may be folded over the header 512 and secured to the other side of the header 512 and the other side wall of the receptacle 508 to close the open end of the receptacle 508. The apertures 412 are configured with an apex, such that the header 512 is accurately and precisely oriented with respect to the hooks 410 of the shuttle assembly 208 when the prescription bag 212 is picked. Alternatively, the apertures 412 may be configured with other shapes at least partially defining an apex (e.g., a diamond, a pentagon, etc.), or the apertures 412 may be circular-shaped.

The headers 512 of the bags 212 include opposing alignment tabs 536 that engage slots formed in the trays 214 to maintain consistent spacing between adjacent headers 512 of adjacent bags 212. Also, the alignment tabs 536 facilitate reading of the barcodes 406 on the labels 402 by consistently positioning the labels 402 so they are clearly presented to the barcode reader 210.

Figure 20:
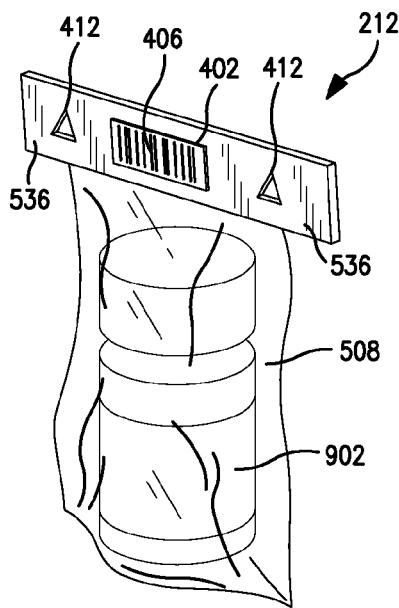
FIG. 20 is a perspective view of a first construction of a bag or container for storing the finished prescriptions.

FIG. 20 illustrates an alternative construction of the bag 212, in which paper or cardboard headers 512 may be used. The labels 402 may be printed to the headers 512, and alternative methods may be used to close the receptacle 508.

As shown in FIGS. 4 and 5, the platforms 216 are movable in relation to each other so that a higher density of platforms 216, distribution trays 214, and prescription bags 212 can be stored in the housing 102. Each platform 216 includes means to raise and lower the platform 216 (e.g., gear motor 220), thereby allowing the shuttle assembly 208 to reach a specific prescription bag 212 stored in a specific distribution tray 214.

With reference to FIG. 5, a staging area 302 toward the front of the housing 102 is shown. The staging area 302 allows a working space for the shuttle assembly 208 to be positioned or stored while the platforms 216 are being moved in anticipation of accessing a particular prescription bag 212. In addition, the staging area 302 provides the working area in which the shuttle assembly 208 delivers the selected prescription bag 212 to the dispense bin 310.

The gear motor 220 may include a pinion (not shown) to drivably engage a rack (also not shown) on the platform support 210b. The rack utilized by the platforms 216 is separate and distinct from the rack utilized by the Z-axis supports 204, such that the platforms 216 and the Z-axis supports 204 may move without affecting one another. Alternatively, a single motor or gear motor may be utilized to raise and lower all of the platforms 216. In addition, hydraulic motors or pneumatic motors may be utilized in place of or in addition to the electric motors 220.

With reference to FIG. 7, the shuttle assembly 208 includes a barcode reader 210 for reading the barcodes 406 (see FIG. 22) on the prescription bags 212. In this way, the shuttle assembly 208 has the capability to associate a specific prescription bag 212 with a random storage location in the housing 102. The shuttle assembly 208 may also include a bag sensor 540 configured to detect the presence of a prescription bag 212 in a specific slot in a tray 214. The bag sensor 540 may be utilized in combination with the barcode reader 210, such that the bag sensor 540 may first detect whether or not a prescription bag 212 is located in a specific slot in a tray 214 before the barcode reader 210 attempts to scan the barcode 406 of the bag 212. If a prescription bag 212 is not detected in a particular slot in the tray 214 by the bag sensor 540, then an attempt to scan the barcode 406 of the missing bag 212 is not made by the barcode reader 210. This may allow for a more expedient process when inventorying the bags 212 in the unit 100, which is discussed in more detail below.

The barcode reader 210 is operable to interface with the computer 124 to output the locations of the individual bags 212 to a database program in the computer 124. The database program thus provides an inventory of the prescription bags 212 stored in the unit 100. When it is desired to access a selected prescription bag 212, the controller 128 interfaces with the computer 124, the gear motors 220 to control movement of the platforms 216, and the drive motors 314, 330, 338 to control movement of the shuttle assembly 208, the X-axis support 222, and the Z-axis supports 204 to position the shuttle assembly 208 in a defined location within the housing 102. In addition, the controller 128 may interface with a hook motor 364 in the shuttle assembly 208 to maneuver hooks 410 to pick a selected prescription bag 212, which is discussed in more detail below. Although the controller 128 is shown as a separate component from the computer 124, it will be understood by those of ordinary skill in the art that the controller 128 and the computer 124 may be incorporated into a single component.

FIG. 5 illustrates the shuttle assembly 208 delivering a selected prescription bag 212 to the dispense bin 310 for delivering the prescription bag 212 to a specific customer. The selected prescription bag 212 originated from a random slot in a random distribution tray 214 located toward the upper portion of the housing 102. Upon identification of the customer, the computer 124 queried the database program to ascertain the location of the selected prescription bag 212. When the location of the prescription bag 212 was determined, the controller 128 interfaced with the lifting mechanism or gear motors 220 to raise the top two platforms 216 to allow access to the distribution tray 214 containing the selected prescription bag 212. The controller 128 then interfaced with the drive motors 314, 330, 338 to maneuver the shuttle assembly 208 into place to select the prescription bag 212. Further, the controller interfaced with the hook motor 364 to maneuver the hooks 410 through respective apertures 412 in the bag 212 to pick the prescription bag 212. Alternatively, more than one shuttle assembly 208 may be used in the unit 100 to expedite retrieving more than one prescription bag 212.

To dispense the selected prescription bag 212, the shuttle assembly 208 is advanced toward the front of the housing 102 along the Z-axis 116, lowered along the Y-axis 112 to a position above the distribution tray 214, then moved along the X-axis 120 to position the prescription bag 212 directly above the deployed dispense bin 310, the operation of which is described in more detail below. The hook motor 364 is then activated to maneuver the hooks 410 to drop the prescription bag 212 into the dispense bin 310.

Figure 11:
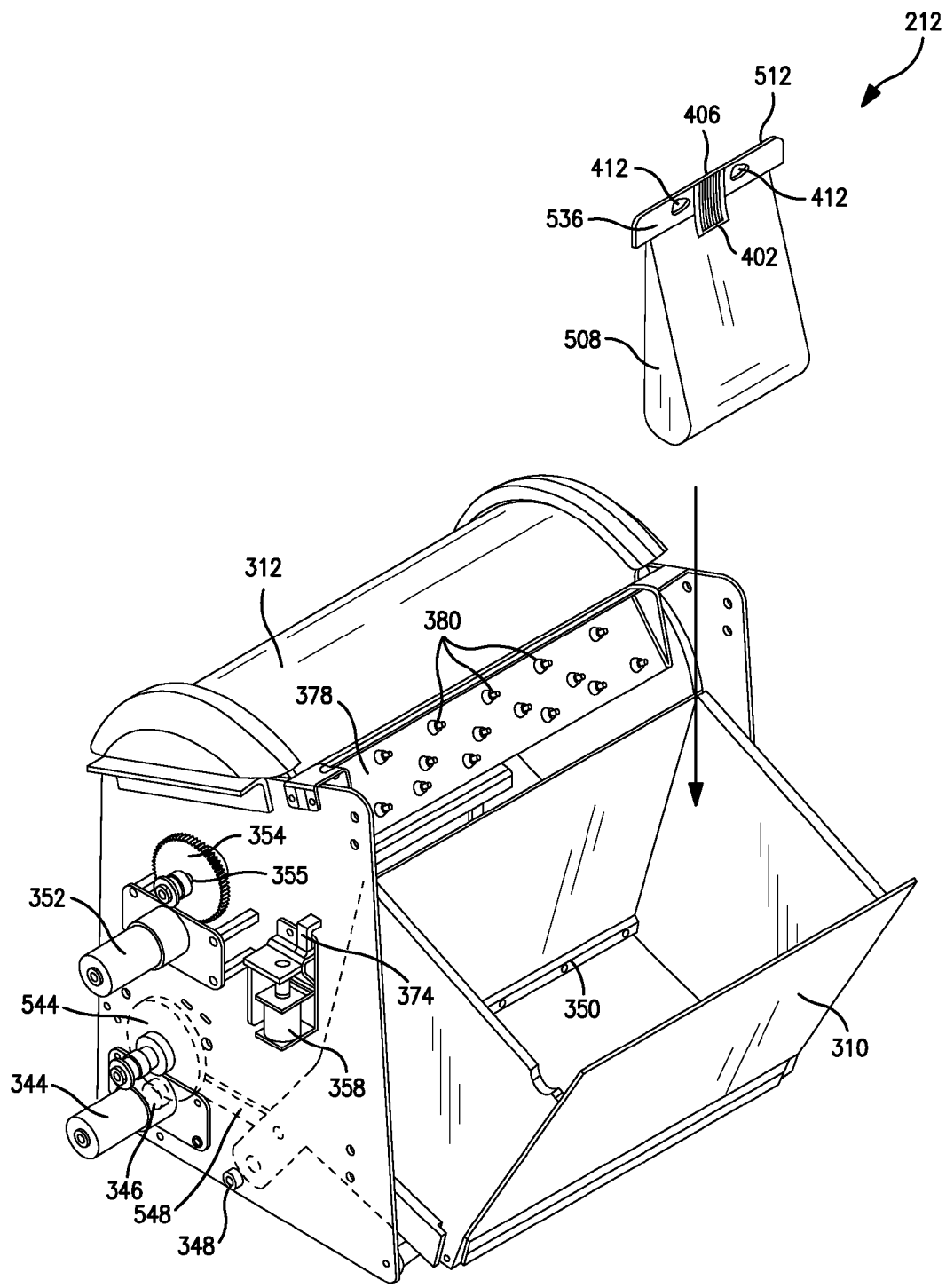
FIG. 11 is a rear perspective view of a dispense bin of the dispensing unit of FIG. 1, illustrating the dispense bin being deployed to receive a finished prescription.

The dispense bin 310 is illustrated in more detail in FIGS. 11-16. With reference to FIG. 11, the dispense bin 310 is movable between a deployed position, in which the prescription bag 212 may be dropped into the dispense bin 310, and a non-deployed position (see FIG. 13), in which the prescription bag 212 is accessible to the customer for removal. More particularly, as shown in FIG. 11, the dispense bin 310 is pivotable between its deployed and non-deployed positions by a drive train. A dispense bin drive motor 344 may include a pinion 346 coupled thereto to drivably engage a driven gear 544. A link 548 may be rotatably coupled at one end to the driven gear a distance from the rotational axis of the driven gear 544. The link 548 may also be rotatably coupled at an opposite end to the dispense bin 310 a distance from a pivot point 348 of the dispense bin 310. As such, the driven gear 544, link 548, and the dispense bin 310 effectively function as a crank-rocker mechanism in that rotation of the driven gear 544 causes the dispense bin 310 to pivot about its pivot point 348 between its deployed and non-deployed positions.

Alternatively, other drive trains may be utilized, including fixing the driven gear to the pivot point 348 of the dispense bin 310, such that the pinion 346 engages the driven gear and causes the dispense bin 310 to pivot without utilizing the link 548. Alternatively, a multiple-gear gear train may be utilized between the pinion 346 and the driven gear on the dispense bin 310. Further, other known drive structures may be utilized to pivot the dispense bin 310 between its deployed and non-deployed positions. A slip-clutch 349 may also be utilized in the drive train of the dispense bin 310 to allow selective slippage between the motor 344 and the dispense bin 310.

The dispense bin drive motor 344 may interface with the controller 128, which may selectively activate the dispense bin drive motor 344 when prompted by the computer 124. With reference to FIG. 11, a product sensor 350 may be positioned in the dispense bin 310 to detect the presence or absence of a prescription bag 212. The product sensor 350 may interface with the computer 124 and the controller 128 to indicate the presence or absence of a prescription bag 212 in the dispense bin 310. In the illustrated configuration, the product sensor 350 is a light sensor. An illumination bar 378 containing a plurality of illumination devices 380 (e.g., light emitting diodes, incandescent lights, and so forth) may be positioned above the dispense bin 310 when the dispense bin 310 is in its non-deployed position. The computer 124 may prompt the controller 128 to activate the illumination devices 380 when a prescription bag 212 is dispensed into the dispense bin 310 for the customers convenience in retrieving the prescription bag 212 from the dispense bin 310. In addition, if the product sensor 350 detects that the prescription bag 212 has not been removed by the customer after a period of time, the controller 128 may cause the illumination devices 380 to flash to alert the customer to remove the prescription bag 212 from the dispense bin 310.

Figure 12:
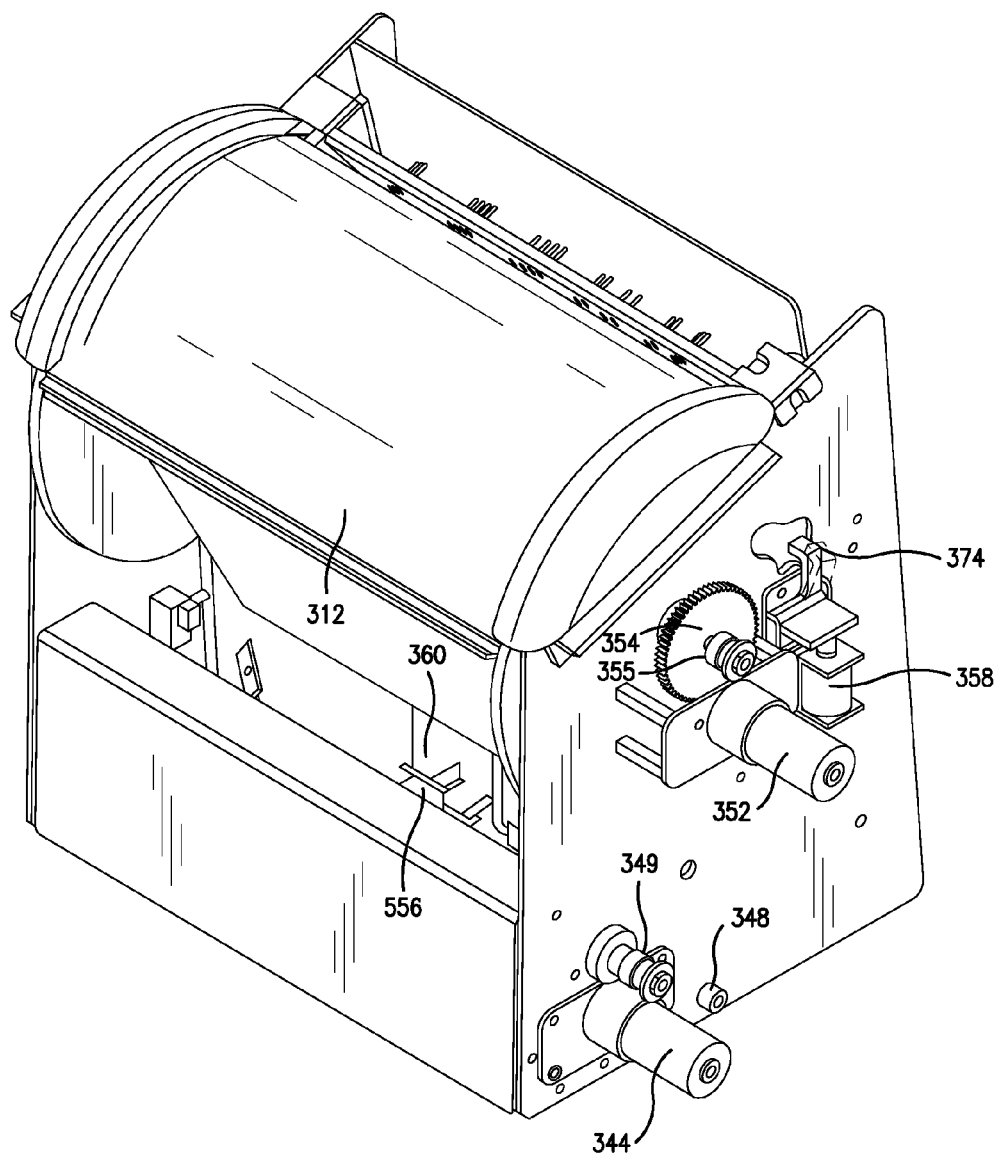
FIG. 12 is a front perspective view of the dispense bin of FIG. 11, illustrating a dispense bin lid in a closed position.
Figure 13:
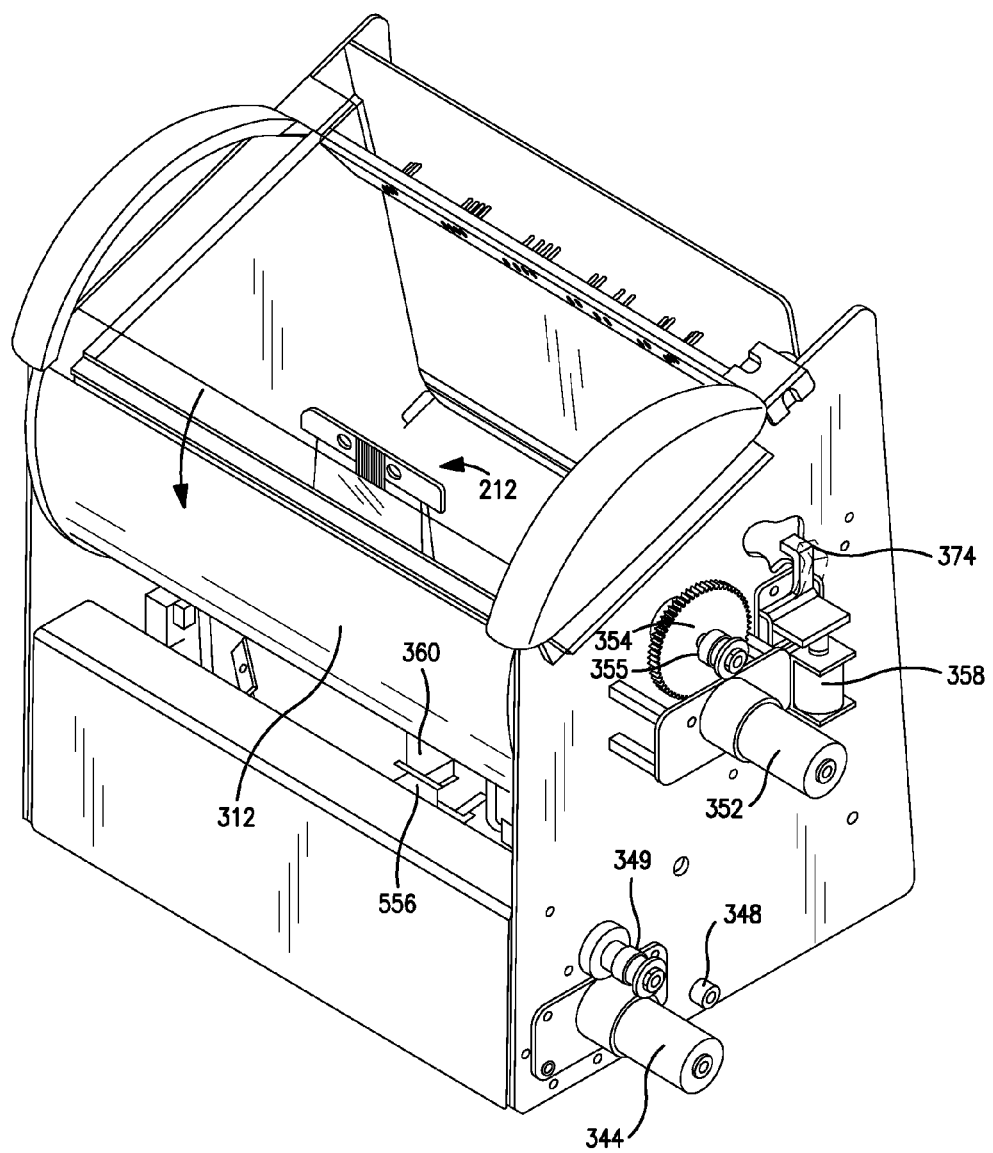
FIG. 13 is a front perspective view of the dispense bin of FIG. 11, illustrating the dispense bin lid in an open position so the finished prescription may be removed from the dispense bin.

With reference to FIGS. 12 and 13, the dispense bin lid 312 is movable between a closed position (see FIG. 12), in which the prescription bag 212 is inaccessible to the customer, and an open position (see FIG. 13), in which the prescription bag 212 is accessible to the customer for removal. More particularly, as shown in FIG. 12, the dispense bin lid 312 is pivotable between its closed and open positions by a drive train. A dispense bin lid drive motor 352 may include a pinion 353 (see FIG. 14) coupled thereto to drivably engage a driven gear 354 fixed to the dispense bin lid 312 at the pivot point of the dispense bin lid 312. As such, rotation of the pinion 353 may cause the dispense bin lid 312 to pivot between its closed and open positions. Alternatively, a multiple-gear gear train may be utilized between the pinion 353 and the driven gear 354 on the dispense bin lid 312. The dispense bin lid drive motor 352 may interface with the controller 128, which may selectively activate the dispense bin lid drive motor 352 when prompted by the computer 124. Alternatively, other known drive structures may be utilized to pivot the dispense bin lid 312 between its closed and open positions. A slip-clutch 355 may also be utilized in the drive train of the dispense bin lid 312 to allow selective slippage between the motor 352 and the dispense bin lid 312.

With reference to FIG. 12, the dispense bin lid 312 may be locked in its closed position by a solenoid 358 actuating a lock mechanism 374. The lock mechanism 374 is biased to engage an aperture 572 in the dispense bin lid 312. A switch 376 (see FIG. 15) may be used in combination with the computer 124 to detect whether the lock mechanism 374 is engaged with the dispense bin lid 312 to lock the dispense bin lid 312, or disengaged from the dispense bin lid 312 to unlock the dispense bin lid 312.

With reference to FIG. 13, the dispense bin lid 312 is shown in the open position to allow the customer to remove the prescription bag 212 from the dispense bin 310. If, however, the prescription bag 212 is not removed from the dispense bin 310 after a predetermined period, the dispense bin lid 312 may be closed to prevent unintended disbursement of the prescription bag 212 to the wrong customer. The product sensor 350 may be utilized to detect whether or not the prescription bag 212 is removed from the dispense bin 310, and the product sensor 350 may interface with the controller 128 and the computer 124 to activate the dispense bin lid drive motor 352 to close the dispense bin lid 312.

Figure 14:
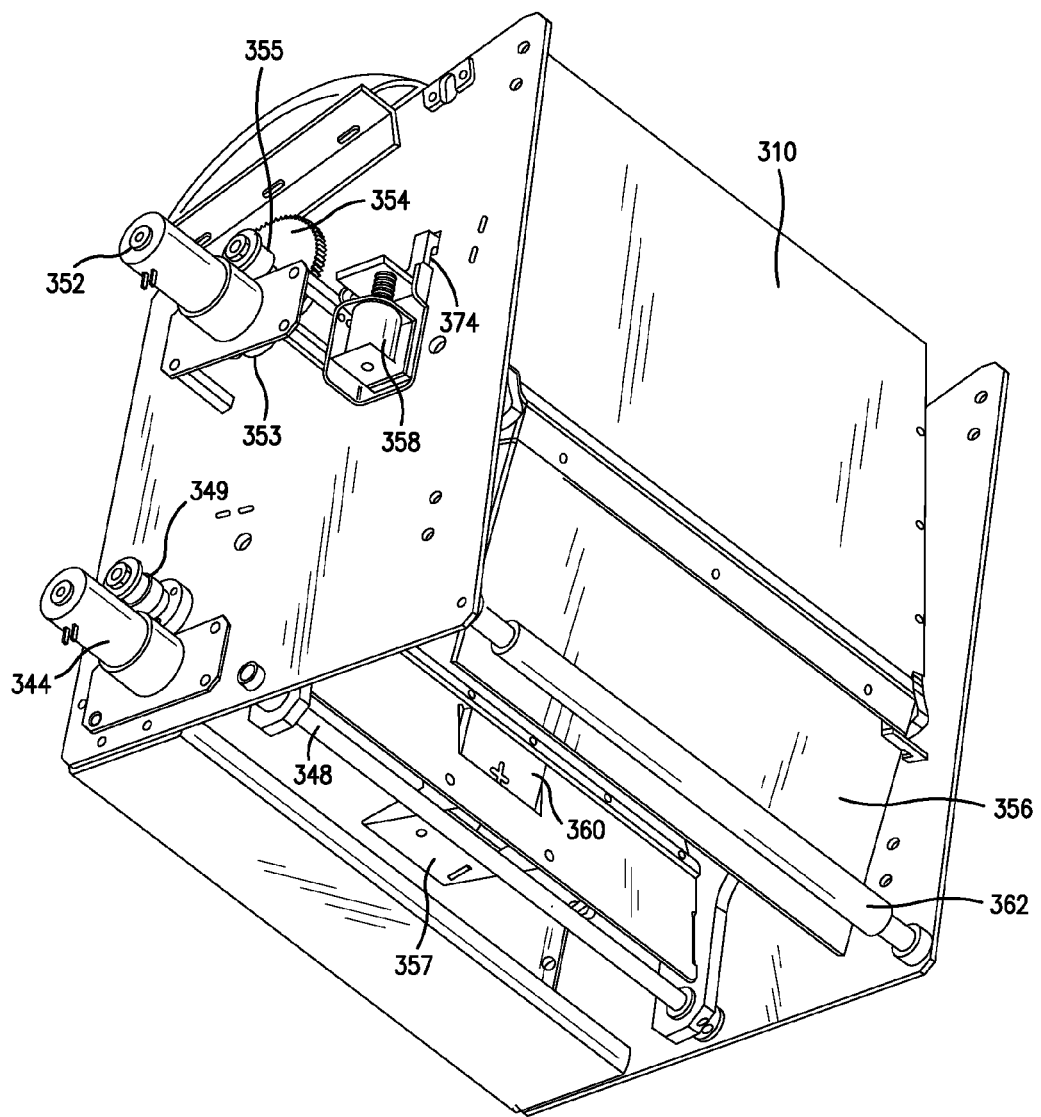
FIG. 14 is a rear perspective view of the dispense bin of FIG. 11, illustrating a trap door being deployed to drop the finished prescription from the dispense bin.

With reference to FIG. 14, the dispense bin 310 may also incorporate a trap door 356 to allow the prescription bag 212 left in the dispense bin 310 to be dropped from the dispense bin 310 into a return bin 552. The prescription bags 212 dropped into the return bin 552 may then be re-checked by the pharmacist or technician and returned to a distribution tray 214 in the unit 100. In the illustrated construction, the return bin 552 is supported below the dispense bin 310 in the access door 313. The pharmacist or technician may periodically check the return bin 552 by opening the access door 313 and removing the return bin 552. The prescription bags 212 in the return bin 552 may then be reloaded into the unit 100 as described in more detail below. In some other embodiments, the unit 100 can be configured to notify the pharmacy staff via software, email, page, text message, recorded voice message, and the like when necessary. In this way, the pharmacy staff checks the return bin 552 when necessary.

The trap door 356 is actuated by a solenoid 556 (see FIGS. 12 and 13) and a spring-biased latch mechanism 360. The solenoid is mounted on a bracket 357 (see FIG. 14) coupled to the dispense bin 310. The solenoid may interface with the controller 128, which may selectively activate the solenoid when prompted by the computer 124. FIG. 14 illustrates the trap door 356 in a deployed position, in which the prescription bag 212 is allowed to drop from the dispense bin 310 and into the return bin 552. To deploy the trap door 356, the controller 128 activates the solenoid, which, in turn, retracts the spring-biased latch mechanism. The mechanism 360 is sufficiently retracted by the solenoid to allow the trap door 356 to pivot downwardly to its deployed position.

Figure 15:
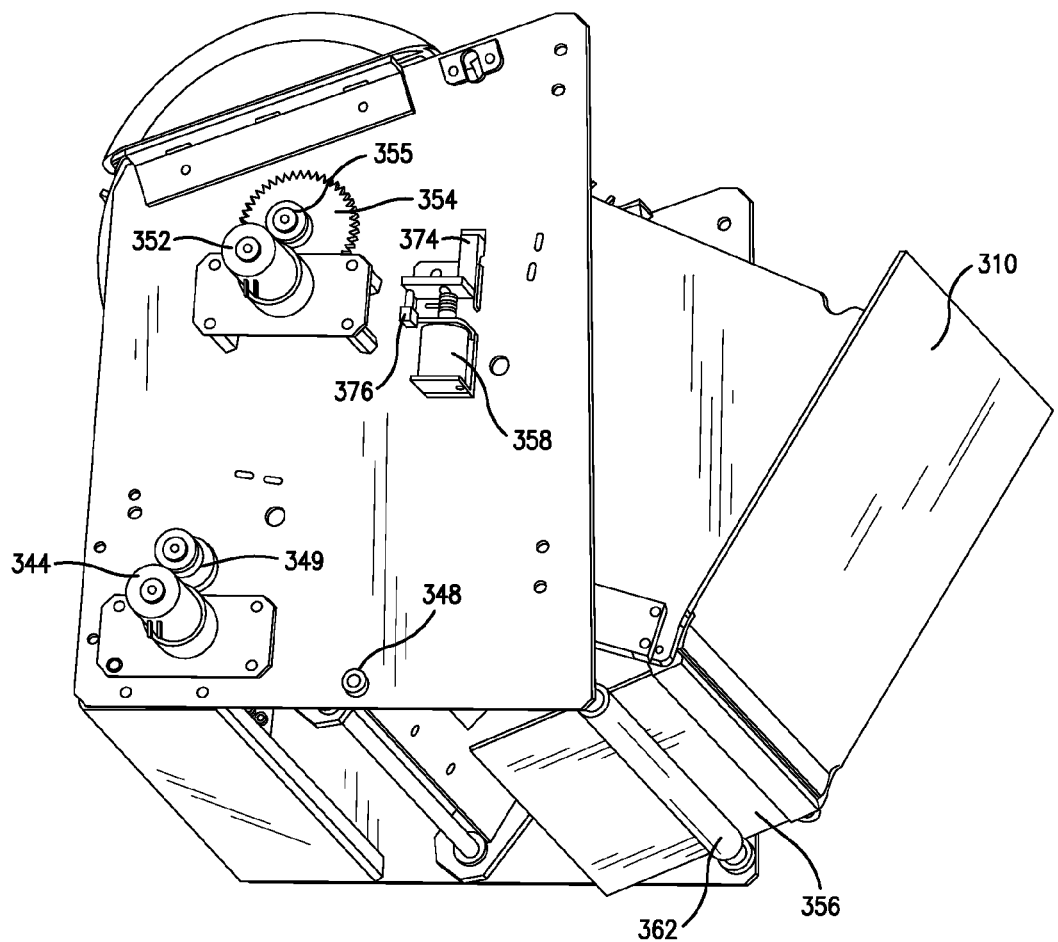
FIG. 15 is a rear perspective view of the dispense bin of FIG. 11, illustrating the trap door being moved to a closed or non-deployed position.
Figure 16:
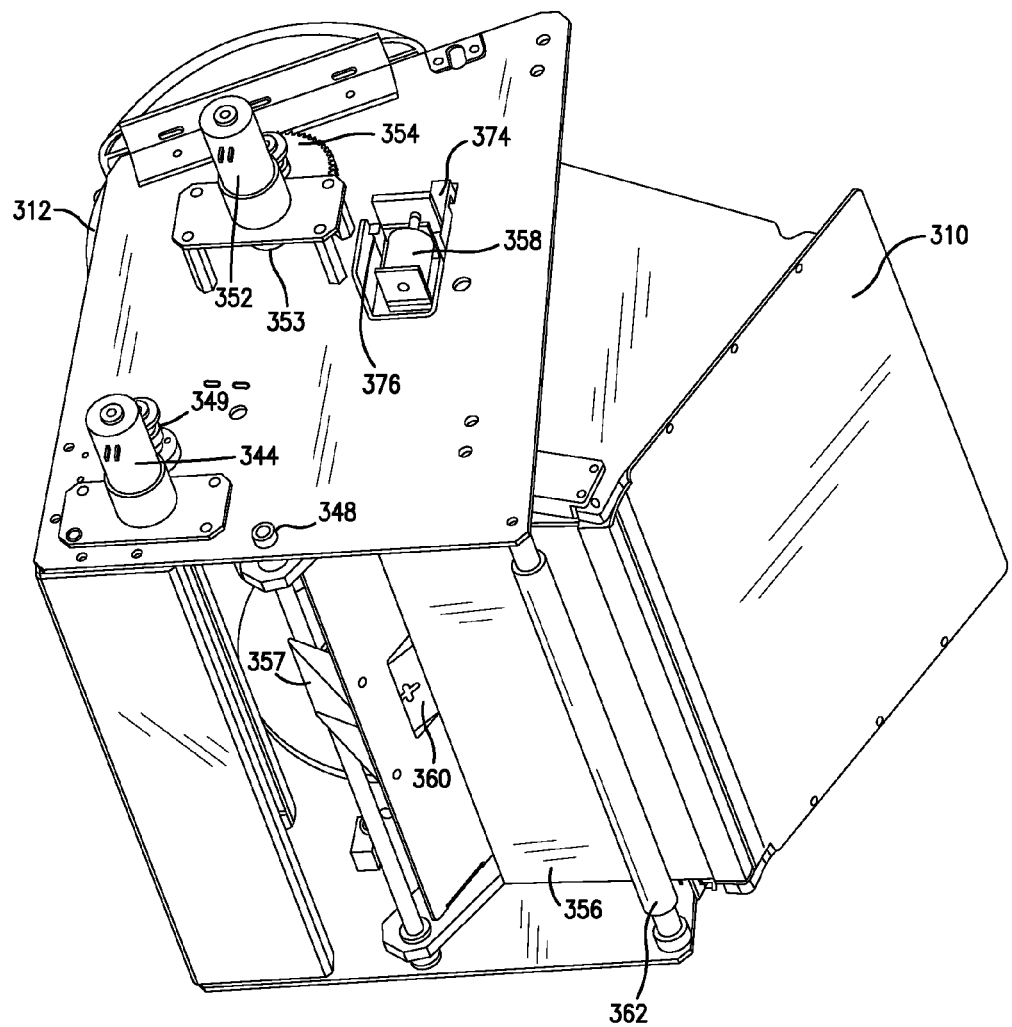
FIG. 16 is a rear perspective view of the dispense bin of FIG. 11, illustrating continued movement of the trap door toward its closed or non-deployed position.

With reference to FIGS. 15 and 16, after the prescription bag 212 is dropped from the dispense bin 310, the trap door 356 is moved to its closed or non-deployed position. To accomplish this, the dispense bin drive motor 344 is activated to pivot the dispense bin 310 to its deployed position. While the dispense bin 310 deploys, the trap door 356 contacts a stationary bar 362 spaced from the dispense bin 310. Continued pivoting of the dispense bin 310 causes the trap door 356 to pivot relative to the dispense bin 310. As shown in FIG. 16, before the dispense bin 310 reaches its deployed position, the trap door 356 engages the latch mechanism 360 and causes the latch mechanism 360 to retract against its spring bias until the trap door 356 clears the latch mechanism 360, at which time the latch mechanism 360 springs outwardly to secure the trap door 356 in its closed or non-deployed position.

More than one dispense bin 310 or pickup location may be incorporated into the unit 100 if it is desired to service more than one customer at a given time. Further, additional shuttle assemblies 208 may be incorporated into the unit 100 to service the additional customers or to pick multiple prescription bags 212 at one time. The unit 100 may also be configured as a double-wide or a triple-wide unit (not shown), such that two or three of the illustrated storage units 100 may be incorporated into a single housing. In such a double-wide or triple-wide unit, one or more transfer mechanisms (e.g., conveyor belts, etc.) may be utilized to transfer a prescription bag 212 between the individual storage units 100 in the double-wide or triple-wide units. For example, a shuttle assembly 208 of a first unit 100 may deposit a prescription bag 212 on the conveyor belt, which may transport the bag 212 to a second unit 100 in the double-wide or triple-wide unit. The shuttle assembly 208 of the second unit 100 may then retrieve the bag 212 from the conveyor belt. In some other embodiments, however, instead of the shuttle assembly 208 of the second unit 100 picking up the bag 212 from the conveyor belt, the second unit 100 will deposit the bag 212 from the conveyor belt into an appropriate dispense bin.

Figure 28:
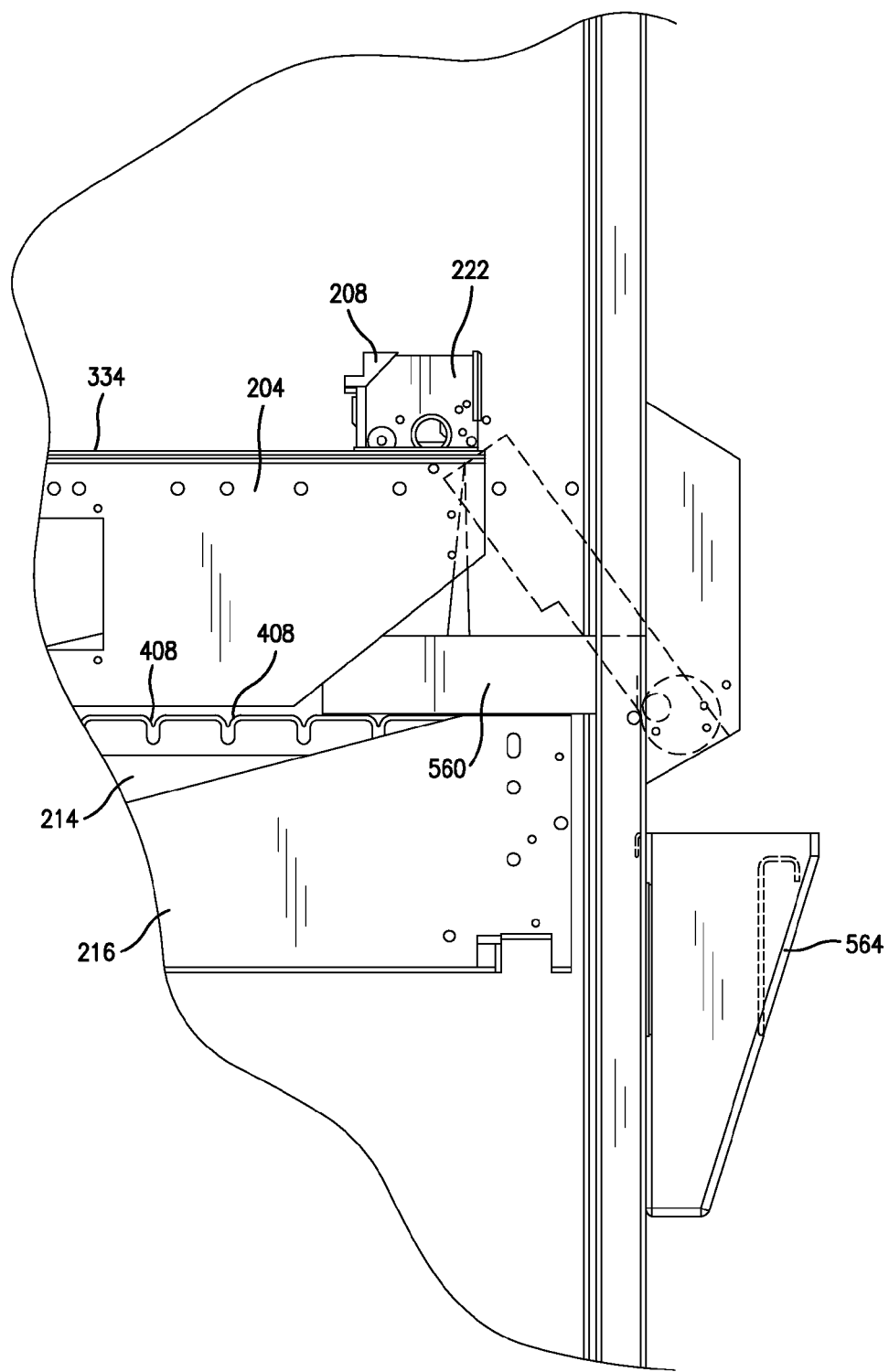
FIG. 28 is a partial cutaway view of the dispensing unit of FIG. 1, illustrating rear dispense of a finished prescription.

With reference to FIG. 28, the shuttle assembly 208 may also deliver the prescription bag 212 to the rear of the housing 102 for the bag 212 to be dispensed from the rear of the housing 102. This may be desirable when the pharmacist or technician wants to access one particular prescription bag 212 in the housing 102, rather than manually accessing a particular tray 214 in the housing. A chute 560 may be located in the housing 102 and pivotable with respect to the housing 102 about a substantially horizontal axis. The chute 560 may be pivotable between a substantially horizontal position, in which the chute 5650 may receive the prescription bag 212 from the shuttle assembly 208, and a substantially vertical position, in which the bag 212 may slide down the chute 560 for deposit in a bin 564. The bin 564 may be removably coupled to the housing 102, such that the pharmacist or technician may detach the bin 564 from the housing 102 to transport the dispensed bags 212.

FIG. 17 illustrates a close-up view of the shuttle assembly 208 reading, identifying, and selecting a particular prescription bag 212 from a particular distribution tray 214. The shuttle assembly 208 utilizes its barcode reader 210 to read the barcode 406 on the label 402 that is located on the prescription bag 212. Alternatively, various forms of electronic identification tags containing information relevant to the customer and/or the prescription may be applied to the prescription bag 212. Accordingly, a means to read these tags may be used in place of the barcode reader 210.

The prescription bag 212 may include labels 402 on each side of the bag 212, such that the barcode reader 210 may read the barcode 406 to identify the bag 212 from either side of the bag 212 by reference or query of the database. The distribution trays 214 include self-aligning V-notches 408 so that the label 402 of each bag is accurately positioned in the distribution tray 214 to facilitate reading of the barcodes 406 by the barcode reader 210.

As shown in FIGS. 6 and 7, the shuttle assembly 208 includes a mechanism (e.g., hooks 410) for engaging corresponding openings or apertures 412 in the prescription bag 212 to remove the prescription bag 212 from the tray 214. With reference to FIG. 6, the hooks 410 are fixed to a single shaft (not shown) passing through the shuttle assembly 208. A hook drive motor 364 includes a pinion 366 coupled thereto to drivably engage a driven gear 368 fixed to the common shaft of the hooks 410. As such, rotation of the pinion 366 causes the hooks 410 to pivot about their common shaft between an "up" or raised position, and a "down" or lowered position. The hook drive motor 364 may interface with the controller 128, which may selectively activate the hook drive motor 364 when prompted by the computer 124. Alternatively, a multiple-gear gear train may be utilized between the pinion 366 and the driven gear 368 on the common shaft of the hooks 410. Further, other known drive structures may be utilized to pivot the hooks 410 between their up and down positions.

One or more switches 370 may be utilized to detect the position of the hooks 410. As shown in FIGS. 6 and 7, one switch 370 may be utilized to detect the up position of the hooks 410, while a second switch 370 may be utilized to detect the down position of the hooks 410. The switches 370 may interface with the controller 128 and the computer 124 to determine when to deactivate the hook drive motor 364.

The hooks 410 may be maneuvered to disengage the apertures 412 in the prescription bag 212 when the prescription bag 212 is to be dropped into the dispense bin 310. Alternatively, the shuttle assembly 208 may utilize different means for selecting the prescription bags 212, such as, for example, suction, magnets, grabbers, holders, and so forth. As such, the prescription bags 212 may incorporate corresponding structure or features, depending upon the different means for selecting the prescription bags 212, to allow accurate and precise picking of the prescription bags 212. For example, grabbers are particularly suited to pick products having a consistent shape and size (e.g., DVD's). Further, such products may not require bags or other containers for vending, and may be directly grasped by the grabbers.

FIG. 2 illustrates the rear of housing 102, which is accessed when the unit 100 is to be reloaded with additional prescription bags 212. Alternatively, the access door 313 may be opened to allow the housing 102 to be accessed from the front for reloading.

The housing 102 may include one or more rear doors 602, which may be locked by electronic solenoids (not shown). The electronic solenoids may be controlled by the computer 124 and the controller 128 to lock and unlock the rear doors 602. The pharmacist or technician may utilize another computer (e.g., the computer or computer network in the pharmacy) to interface with the computer 124 to remotely actuate the electronic solenoids to lock or unlock the rear doors 602. Alternatively, the pharmacist or technician may utilize a keypad (not shown) positioned on the housing 102 to interface with the computer 124 to lock or unlock the rear doors 602. The computer 124 may also be used to interface with the computer or computer network in the pharmacy to maintain an inventory of the prescription bags 212 in the unit 100. The computer 124 may further be used to interface with the computer or computer network in the pharmacy to access information specific to the customer, the customer's prescription, and/or the prescription bag 212.

The rear of the housing 102 may further include means to communicate with the technician or system operator to display whether the system is prepared to be accessed and reloaded. For example, lights 606 may be provided to communicate with the technician or operator, such as a red light may indicate that the machine is in operation and for the operator to wait to open the rear doors 602 or to pull out distribution trays 214 (see FIGS. 17 and 19). Further, a green light may signal to the technician or operator that the rear doors 602 may be opened and that distribution trays 214 may be removed from the unit 100 to be reloaded or inventoried.

When the unit 100 is idle, all of the platforms 216 may be moved to their lowest positions in the housing 102 so that bags 212 may not be removed from the distribution trays 214 without a distribution tray 214 being pulled out of the housing 102. In addition, the platforms 216 may be moved to their lowest positions in the housing 102 when the access door 313 or the rear doors 602 are opened. One or more tray sensors 576 (see FIG. 17) on the platforms 216 may signal the computer 124 and/or the controller 128 when a particular tray 214 is removed from a particular platform 216. If one or more trays 214 are removed from any of the platforms 216, those trays 214 that were removed are identified by the one or more tray sensors 576 so that only those removed trays 214 may be re-inventoried to determine or verify the contents of the trays 214. The inventory process as performed by the shuttle assembly 208 is discussed in greater detail below.

Figure 19:
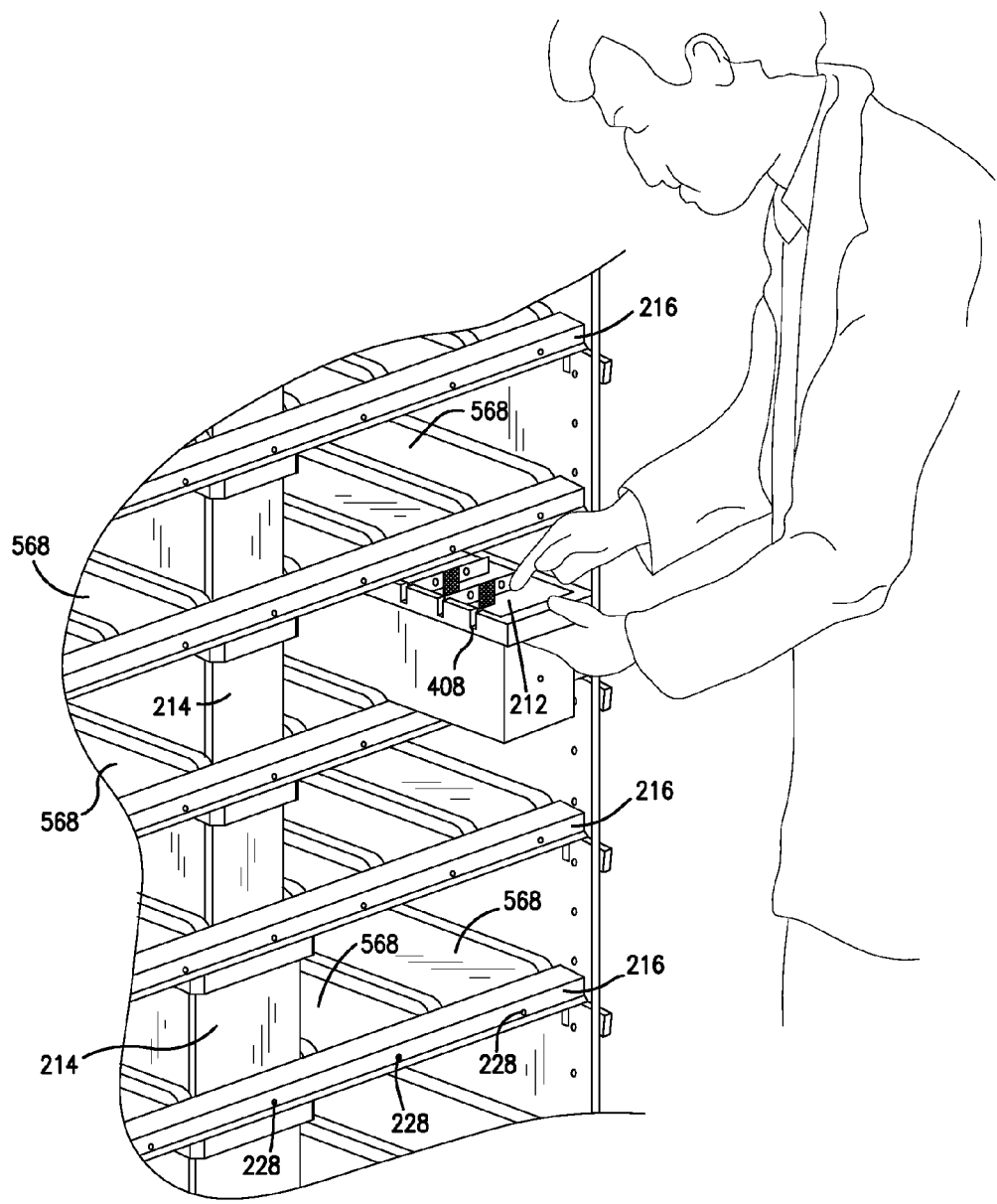
FIG. 19 is a rear perspective view of the dispensing unit of FIG. 1, illustrating the technician loading distribution trays into the dispensing unit.

As shown in FIG. 19, different sizes of trays 214 may be utilized in the unit 100. More particularly, the trays 214 may be configured in a standard size to receive prescription bags 212 of standard size, and a wide size to receive prescription bags 212 larger than the standard-sized bags 212. The platforms 216 may also be specifically configured to receive any of a number of different size trays 214, including the standard size and wide size trays 214. More particularly, the platforms 216 may include a plurality of guides 568, with each guide 568 being configured to receive one tray 214. The guides 568 may be permanently fixed (e.g., by welding, etc.) to the platforms 216 or releasably coupled (e.g., by fastening, using quick-release connectors, etc.) to the platforms 216. The platforms 216 and/or the guides 568 may be changed-out or re-configured on the installation site of the unit 100 to receive any of a number of different size trays 214.

Figure 18:
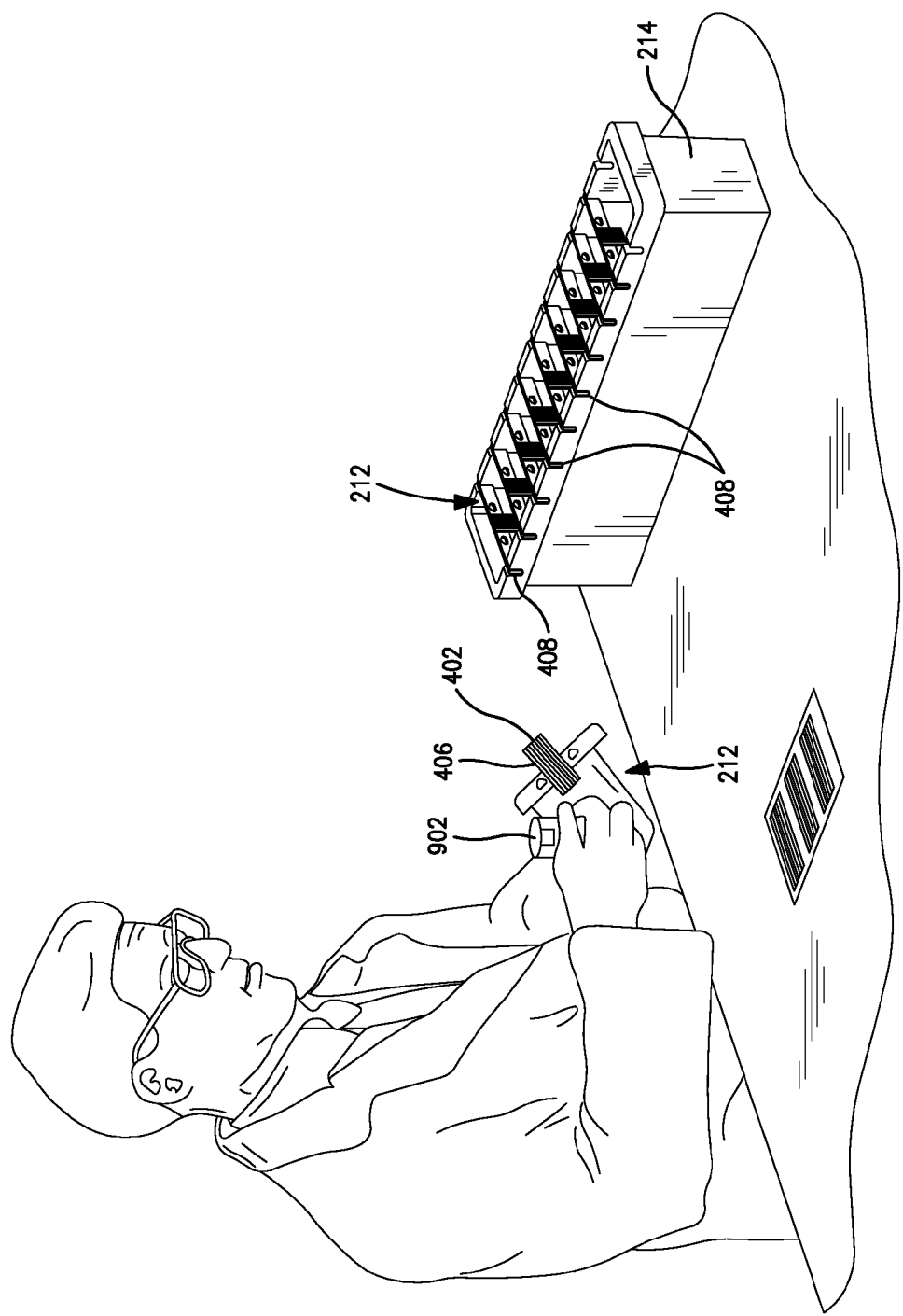
FIG. 18 is a perspective view of a technician/pharmacist loading the distribution trays with finished prescriptions.

FIG. 18 illustrates a pharmacist or technician filling prescriptions by placing a prescribed item 902 into the prescription bag 212. After placing the prescribed item 902 into the bag 212, the pharmacist or technician may close the bag 212 by removing the backing 528 and folding over the label 402 as described above. The pharmacist or technician may then use a barcode scanner (not shown) to scan the barcode 406 on the label 402 to match the prescribed item 902 and the prescription bag 212 to a customer in a database on the pharmacy's computer network.

The bag 212 may then be placed in any random location in the distribution tray 214 so that the bag 212 is captured between the pair of opposing notches 408. The pharmacist or technician may load the trays 214 with the prescription bags 212 at a remote location from the unit 100, such as a countertop in the pharmacy. The pharmacist or technician may access the rear of the housing 102 via the rear doors 602 and place the filled distribution tray 214 into an open guide 568. The pharmacist or technician may repeat this process as many times as necessary to place new prescription bags 212 into the unit 100 or to fill empty slots in the distribution trays 214.

The unit 100 may also include an auxiliary door (not shown) in one or both of the access door 313 and the rear doors 602 of sufficient size to allow a single tray 214 to be inserted or removed from the housing 102 without opening the access door 313 or the rear doors 602. Such an auxiliary door may allow reloading or restocking the unit 100 without taking the unit 100 off-line.

In addition, the unit 100 may utilize a hopper (not shown) to facilitate loading, re-loading, or restocking the unit 100 with new prescription bags 212. For example, the pharmacist or technician may deposit the bags 212 in the hopper, and the shuttle assembly 208, alone or in combination with other components, may pick the bags 212 and load the bags 212 into a random location in the unit 100.

Figure 24:
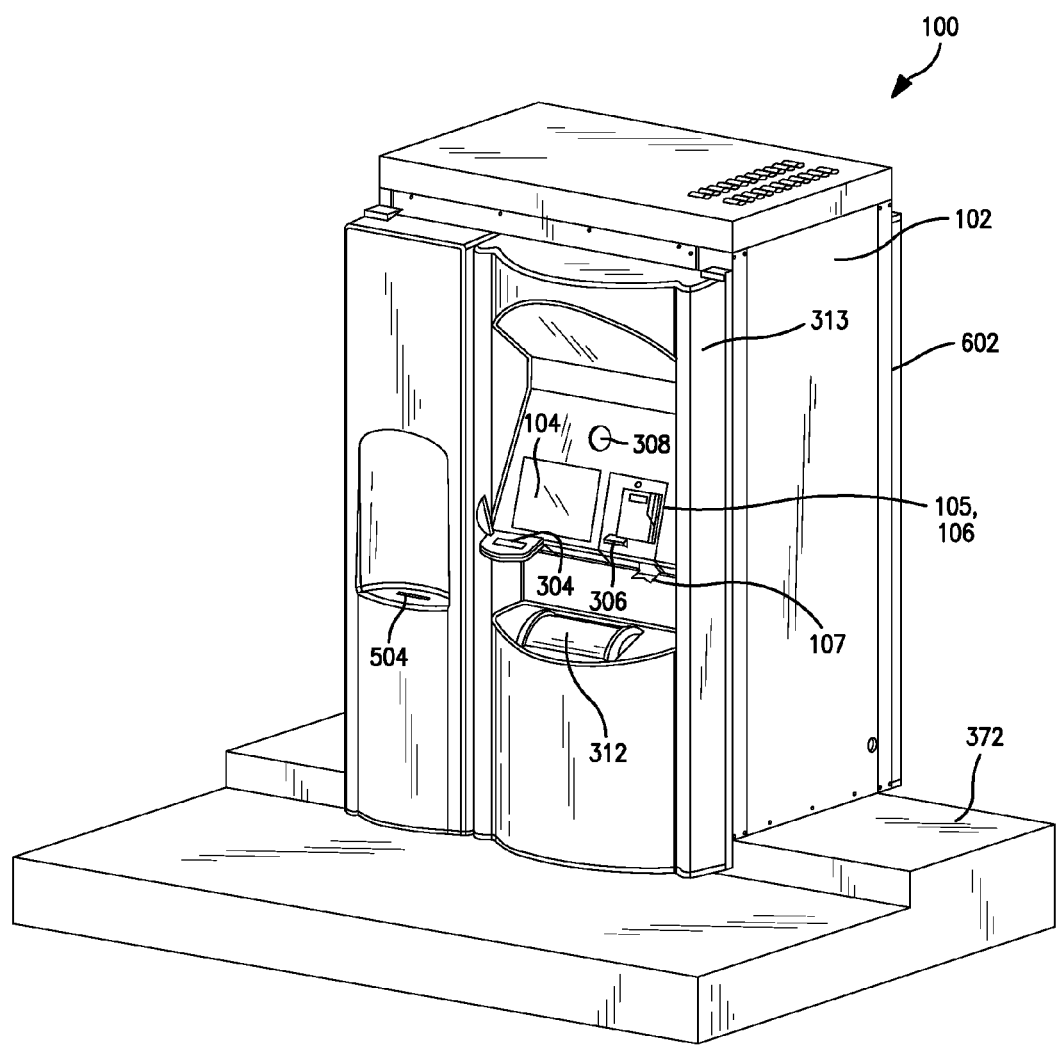
FIG. 24 is a front perspective view of the random access and random load dispensing unit of the present invention, illustrating a housing of the unit being vertically offset from an access door of the unit including customer interface components.

The unit 100 may be utilized at a location inside of a store, such as adjacent to a pharmacy counter. With reference to FIG. 24, the unit 100 may also be adjustable to account for pharmacies that are located on raised platforms 372. More particularly, the housing 102 of the unit 100 may be located on the same level as the pharmacist or technician who is standing on the raised platform 372, while the access door 313 including the customer interface components (i.e., the touch screen 104, magnetic stripe card reader 105 and/or credit card reader 106, barcode scanner 107, signature pad 304, receipt dispense opening 306, camera 308, and dispense bin 310) may be located at the same level as the customer, who is standing at a level or an elevation below the raised platform 372. This facilitates access into the housing 102 by the pharmacist or technician, while also facilitating access to the above-identified customer interface components by the customer. If a unit 100 were configured for use on a raised platform like that discussed above, the computer 124 may be configured appropriately to maneuver the shuttle assembly 208 in such a path to accommodate for the height difference between the dispense bin 310 and the housing 102.

The unit 100 may allow the customers to select, purchase, and receive their prescription drugs, or other consumer items effectively without human interaction in the store. More particularly, customers may purchase their prescription drugs without direct contact with the pharmacist or technician responsible for filing the customer's prescription. In such a capacity, the unit 100 effectively functions as an automated storage facility for storing prescription bags 212 in a location accessible to the customer, even during times when the store or pharmacy is closed. In addition, the unit 100 may be utilized outside of a store location, such as in an automobile drive-through system so that the customer may purchase their prescription bags 212 or other goods while remaining in their automobile.

Figure 25:
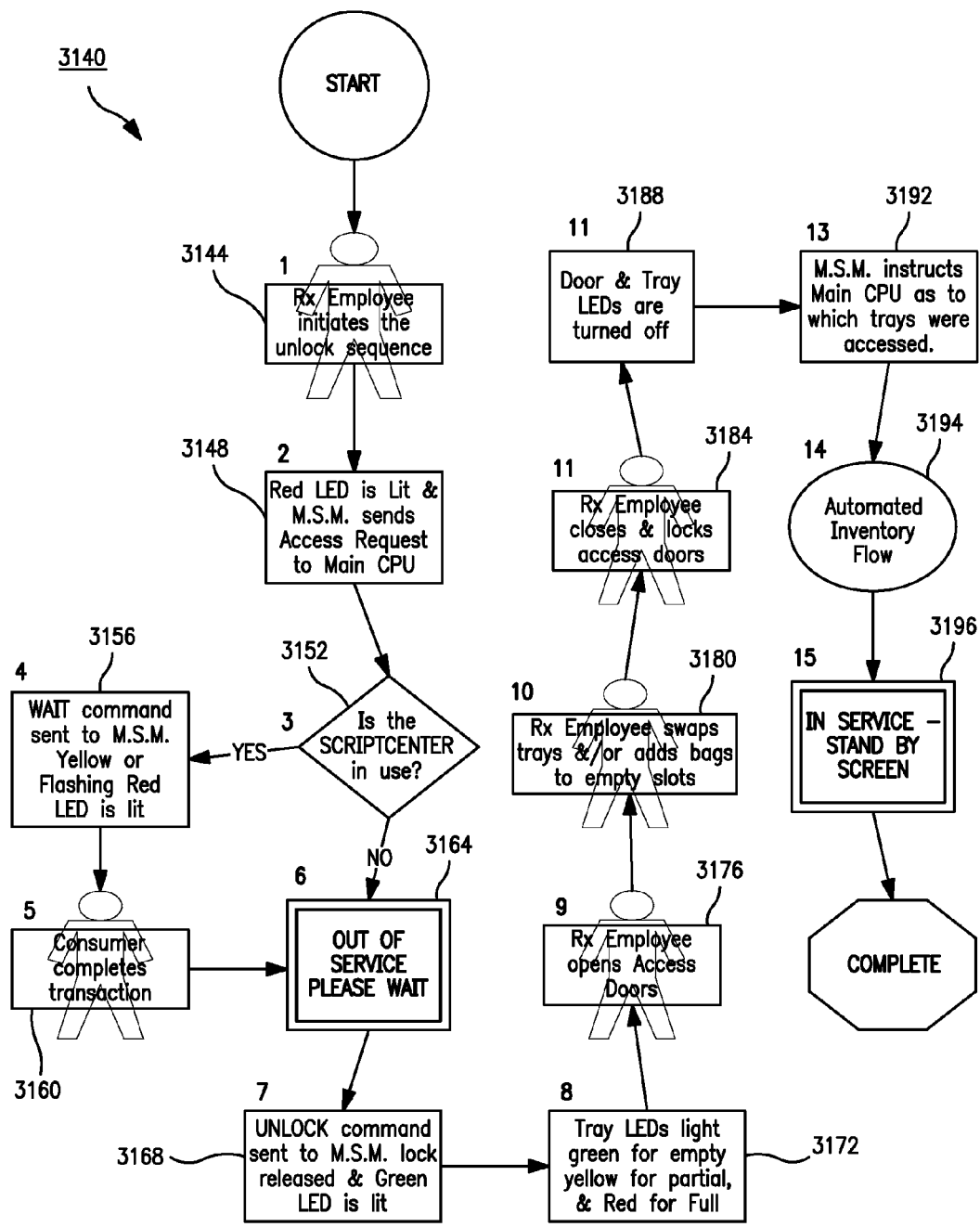
FIG. 25 is a flowchart schematically illustrating the loading process of the dispensing unit of FIG. 1.

With reference to FIG. 25, a process for loading the unit 100 is schematically illustrated. The loading process allows a pharmacist or a technician to replace empty trays 214 with filled trays 214 and/or fill empty slots in partially-empty trays 214 with new prescription bags 212 containing finished prescriptions.

In creating a finished prescription, as is customary, the pharmacist first receives a prescription for a customer from an authorized medical professional, selects an appropriate prescription drug to fill the customer's prescription, and then fills the container 902 with the selected prescription drug to fill the prescription. The pharmacist may then insert the container 902 into the prescription bag 212 and either transfer a label 402 including a barcode 406 from the prescription documentation to the bag 212 to identify the contents of the container 902 and/or the bag 212, or use a barcode reader to scan a pre-printed barcode on the bag 212 and then scan the barcode 406 associated with that prescription to correlate a particular bag 212 to a particular prescription in the database program of the computer 124. The pharmacist or technician may then insert the prescription bags 212 into one or more trays 214 for deposit into the unit 100, or the prescription bags 212 may be deposited into empty slots in partially-empty trays 214 during the loading process.

To load the unit 100, the pharmacist or technician may first initiate a sequence for unlocking the rear doors 602. During the sequence to unlock the rear doors 602, the controller 128 may interface with the computer 124 to request permission to unlock the rear doors 602. If the unit 100 is not in use by a customer, the touch screen 104 may display a message indicating the unit 100 is out of service, and the controller 128 receives a signal from the computer 124 to unlock the rear doors 602. After the rear doors 602 are unlocked, the pharmacist or technician may visually identify empty trays 214 and replace any empty trays 214 with filled trays 214 containing new prescription bags 212. The trays 214 may be removed and/or replaced in random locations in the unit 100. In other words, the trays 214 are not associated with permanent locations in the unit 100. The pharmacist or technician may also identify which trays are partially empty so that new prescription bags 212 may be inserted in the empty slots in the partially empty trays 214. The pharmacist or technician may identify which trays 214 are empty or partially empty by referencing indicator lights 228 (see FIG. 19) located adjacent or beneath the trays 214. The indicator lights 228 (e.g., bi-color LED's) may be varied between different colors and/or intensities (i.e., flashing) by the computer 124 and/or controller 128 to indicate various tray states or fill levels (e.g., a full tray 214, an empty tray 214, or a partially-empty tray 214).

After the new prescription bags 212 have been deposited into the unit 100, the pharmacist or technician closes and locks the rear doors 602. The controller 128 may then interface with the computer 124 to relay which trays 214 were accessed by the pharmacist or technician in order to update the database program in the computer 124 to ascertain an accurate inventory of the prescription bags 212 in the unit 100. The updated inventory of prescription bags 212 in the unit 100 is performed by the shuttle assembly 208 passing over the new prescription bags 212 and reading their barcodes 406 with the barcode reader 210. To complete the loading process, the computer 124 may prompt the touch screen 104 to display a message indicating the unit 100 is back in service.

The unit 100 may also automatically consolidate partially-filled trays 214 without any input from the pharmacist or technician. For example, multiple partially-filled trays 214 may be identified while the shuttle assembly 208 re-inventories the bags 212 in the unit 100. The computer 124 and/or controller 128 may then re-assign the bags 212 in one of the partially-filled trays 214 to fill empty slots in other partially-filled trays 214. The controller 128 may then direct the shuttle assembly 208 to reposition the bags 212 accordingly. Prescription bags 212 containing expired filled prescriptions or expired products may be repositioned to a specific tray 214 for the pharmacist or technician to remove from the unit 100, detailed hereinafter.

In some embodiments, when the pharmacy staff needs to load a bag into the unit 100, the pharmacy staff slides out trays of the unit 100 and deposits the bag into an empty slots in the unit 100. FIG. 25 illustrates an exemplary loading process 3140. At block 3144, the pharmacy staff initiates an unlock sequence. A red light-emitting diode ("LED") of the unit 100 is lit, and a motion system micro-controller ("MSM") of the unit 100 sends a request access the unit 100 at block 3148. If the unit 100 is being used as determined at block 3152, the loading process 3140 sends a wait command to the MSM, and an LED is lit or flashes at block 3156. When the transaction is complete at block 3160, or when the unit 100 is not being used, the touch screen 104 display an "out of service" message at block 3164.

The loading process 3140 then sends an unlock request to the MSM, a lock on the unit 100 is released, and a green LED is lit at block 3168. Each tray then lights a particular tray LED associated with the tray at block 3172. For example, a green LED is lit for the tray if the tray is empty. A yellow LED is lit if some slots of the tray are occupied. A red LED is lit if all of the slots are occupied. Once a yellow LED or a green LED is located, the pharmacy staff opens a corresponding access door of the selected tray at block 3176, deposits bags to the empty slots of the tray at block 3180, and locks the access door when done depositing at block 3184, respectively. Thereafter, the tray LED's are turned off at block 3188. The MSM then instructs the main processor which tray was selected at block 3192. An automated inventory process, described hereinafter, is initiated at block 3194. The touch screen 104 subsequently returns to a standby screen at block 3196. The loading process 3140 then terminates.

Figure 26:
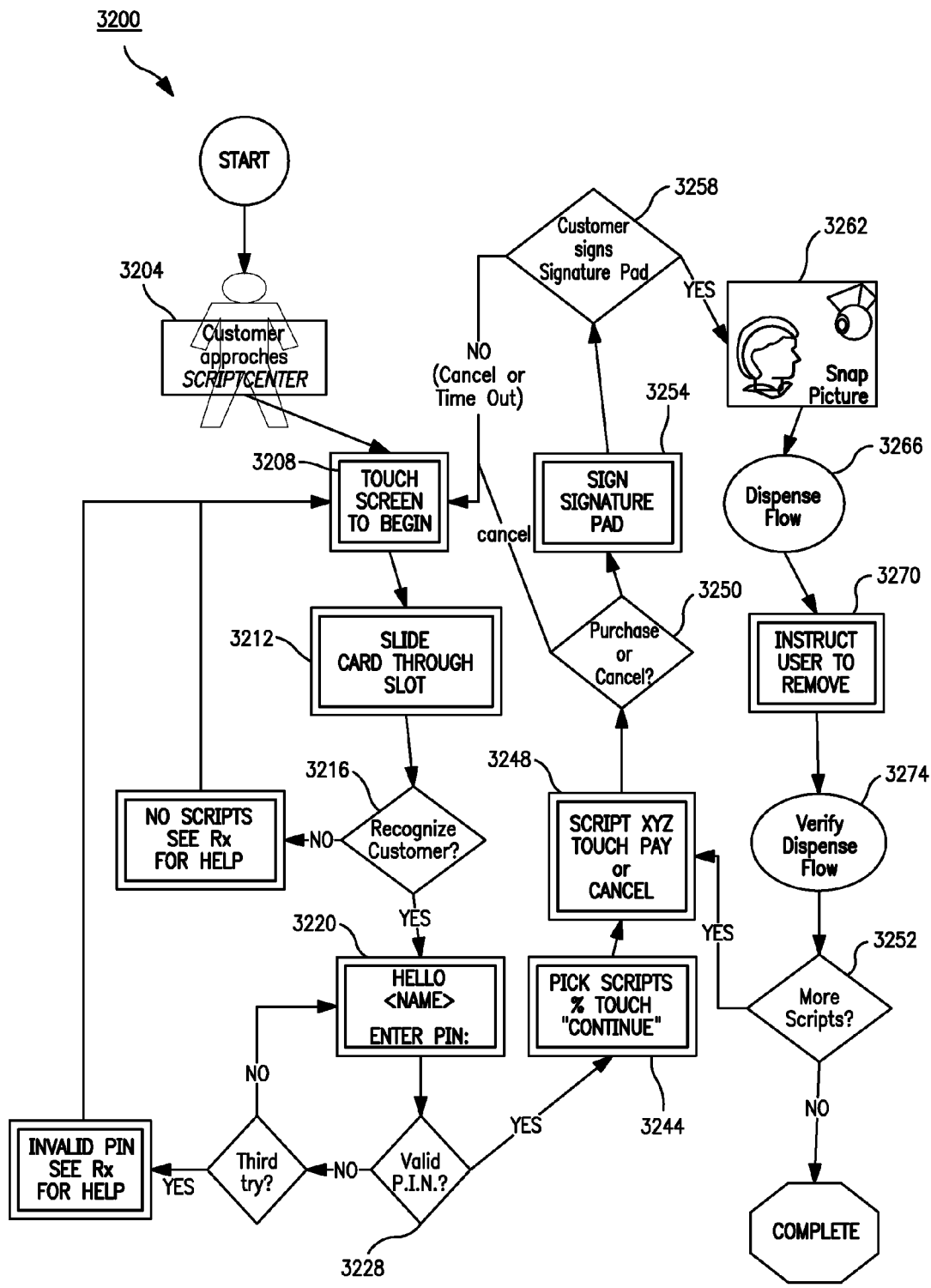
FIG. 26 is a flowchart schematically illustrating the dispensing process of the dispensing unit of FIG. 1.

With reference to FIG. 26, a process for dispensing the prescription bags 212 is schematically illustrated. The dispensing process may be initiated by a customer touching the touch screen 104, which may display a greeting message to the customer. Then, the customer may be instructed to identify themselves by, for example, sliding their credit card through an identification card reader (e.g., magnetic strip card reader 105 or credit card reader 106). The customer may also have their pharmacy discount card or prescription drug card scanned by the barcode scanner 107 for supplemental or primary identification purposes. In some embodiments, if the customer forgets the password, the unit 100 can display on the touch screen 104 a password hint question and prompt for an answer. The password hint question and the answer to the password hint question are generally pre-selected by the customer during the registration process.

The database program in the computer 124 may then compare the customer's identity with the list of registered customers in the database. If no information for the particular customer and/or inaccurate login information (such as the password) is provided, the computer 124 may prompt the touch screen 104 to display a message referring the customer to the pharmacist or the technician for assistance.

If the customer enters a password or PIN that is verified by the computer 124, the computer 124 may then query the database program to check the number of prescription bags 212 corresponding to the customer that are stored in the unit 100. The computer 124 may then display on the touch screen 104 a message listing all of the prescription bags 212 corresponding to the customer that are stored in the unit 100, and behind the counter if any. The customer may choose to purchase any/all prescription bags 212 by selecting/touching the button associated with the desired prescription bag(s) 212 on the touch screen 104. At this point, additional information can be captured. For example, if the patient is a Medicare patient, the software will collect information regarding the relationship of the customer using the machine to the patient for whom the prescription was written. Additionally, the patient may be asked to verify that they have requested their prescriptions be stored in non-child resistant (or easy open) packages. Alternatively, if the customer logged in to the unit 100 utilizing the touch screen 104 rather than the credit card reader 106, the customer will be prompted through a payment selection process after selecting their prescription bags 212. Such a payment selection process can include being prompted to enter a credit card into the credit card reader 106 or entering cash into the cash acceptor.

If the customer chooses to continue with the transaction, the computer 124 may prompt the touch screen 104 to display a message instructing the customer to sign their name on a signature pad (see FIG. 1 #304) to finalize their purchase of the first prescription bag 212. This signature is also captured for all purchases where a third party insurer was used to pay for all or part of the prescription, to acknowledge the Medicare relationship, and also to acknowledge the receipt of non-child resistant packaging. The customer's signature is recorded electronically by the computer 124. If the customer chooses not to sign the signature pad, the computer 124 may prompt the touch screen 104 to return to the greeting message at the beginning of the dispensing process. However, if the customer signs the signature pad, the computer 124 may prompt a security camera to photograph the customer to produce a photographic record of the transaction. The computer 124 then links the photographic record or the signature to the transaction, thereby producing a means for reproducing the photograph with the information in a report format. In this way, the report can be accessed through a network or the Ethernet 2926 by other systems.

After taking the photograph, the computer 124 may interface with the controller 128 to provide instructions relating the location of the customer's first selected prescription bag 212. Further, the shuttle assembly 208 and the platforms 216 may be maneuvered as described above and in the flowchart illustrated in FIG. 27. After the first prescription bag 212 is dispensed into the dispense drawer 224, the computer 124 may prompt the touch screen 104 to display a message instructing the customer to remove the first prescription bag 212 from the dispense drawer 224. The computer 124 may then interface with the controller 128 and/or other sensors or components in the unit 100 to verify the dispensing of the prescription bag 212 and/or the recovery of the prescription bag 212 from the dispense drawer 224.

After dispensing the first prescription bag 212, and if the customer has additional prescription bags 212 stored in the unit 100, the computer 124 may prompt the touch screen 106 to return to the message listing all of the customer's prescription bags 212 stored in the unit 100. The customer may purchase a second prescription bag 212 by repeating the above procedure. If the customer does not have additional prescription bags 212 stored in the unit 100, the transaction may be completed.

More particularly, as shown in FIG. 26, the flow chart illustrates an exemplary dispensing process 3200, and starts with a consumer approaching the unit 100 at block 3204. The consumer can touch the touch screen 104 to begin the dispensing process 3200 at block 3208. The consumer is then prompted to slide a registration or identification card or a credit card through any of the readers such as the credit card reader 106 at block 3212 to identify him or her. If the unit 100 recognizes the consumer at block 3216, the dispensing process 3200 continues to prompt for a password at block 3220; otherwise, the consumer can be directed to seek help with the pharmacy staff at block 3224. If the password is valid (as determined at block 3228), the dispensing process 3200 continues at block 3244. However, if the password is considered invalid (determined at block 3228), the unit 100 will repeat block 3220 to prompt for another password for a number of times. In the embodiment shown in FIG. 26, the unit will continuously prompt for a valid password for three times, determined at block 3236. If after the third attempt, and if the password is still invalid, an invalid password message is displayed at block 3240 and the dispensing process 3200 restarts at block 3208.

If the password is considered valid at block 3228, the touch screen 104 will display a list of the prescriptions ordered at block 3244. At this point, the unit 100 can also record the number of prescriptions. Once the consumer has selected the prescriptions, and selected to continue with the dispensing process 3200, the touch screen 104 will prompt the consumer for purchase or cancellation at block 3248. If the consumer selects cancellation (determined at block 3250), the dispensing process 3200 returns to block 3208. If the consumer selects purchase at block 3250, the consumer is then prompted to sign the signature pad 304 at block 3254. If the consumer signs the signature pad 304 determined at block 3258, the dispensing process 3200 continues at block 3262 which snaps a picture of the consumer, or takes some biometrics information of the consumer. If the consumer has not signed the signature pad 304 within a predetermined amount of time, the dispensing process 3200 restarts at block 3208.

Once a consumer record such as the picture or the biometrics information has been captured at block 3262, the unit 100 will pick up the selected prescription mechanically at block 3266, detailed hereinafter. The touch screen 104 will also instruct the consumer to remove the prescription(s) from the unit 100 at block 3270. The dispensing process 3200 will then verify the removal of the prescription at block 3274, detailed hereinafter. When there is more prescriptions to be dispensed at block 3252, the dispensing process 3200 repeats at block 2848; otherwise, the dispensing process 3200 terminates at block 3278. In some other embodiments, the block 3252 can be eliminated.

Figure 27:
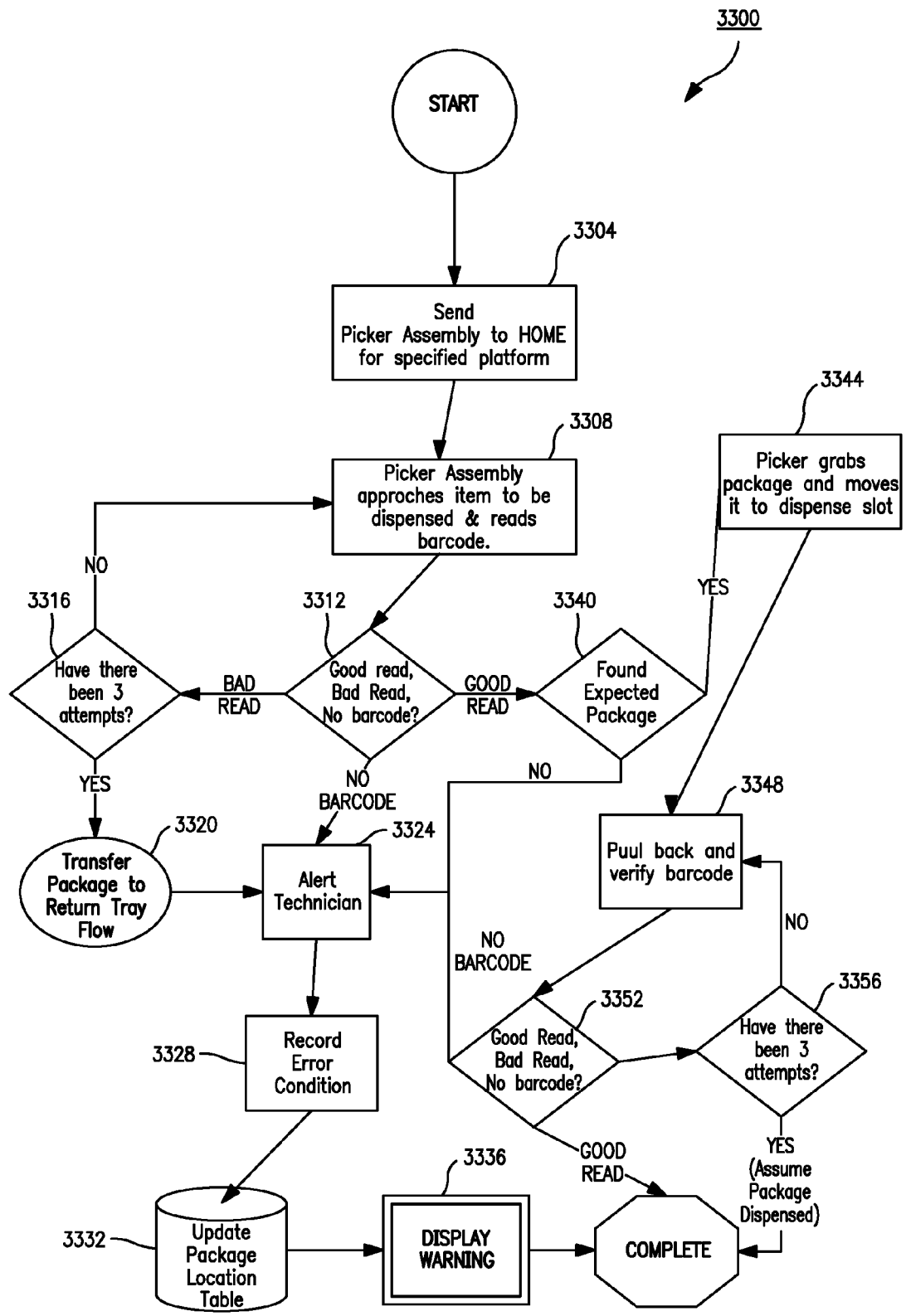
FIG. 27 is a flowchart schematically illustrating the operations performed by the dispensing unit of FIG. 1 in dispensing a finished prescription.

FIG. 27 shows an exemplary mechanical dispensing process 3300 in the unit 100 after the consumer has signed the signature pad 304. Initially, the unit 100 ensures that a picker assembly is at a home location at block 3304. Once the consumer signs the signature pad 304, a prescription identification number associated with the prescription is read, a plurality of coordinates with respect to the prescription identification number is determined. The picker assembly is then moved to the coordinates and scans in the barcode of the prescription coordinates at block 3308. If it is determined that the barcode is a bad barcode read at block 3312, the mechanical dispensing process 3300 allows a number of repeated barcode reads starting at block 3308. In the embodiment shown, the picker assembly can read the barcode a total of three times. If after three attempts (determined at block 3316), the prescription is transferred to a return tray at block 3320, and a technician is alerted at block 3324. The bad read is then recorded at block 3328, and an associated prescription database is updated at block 3332. Thereafter at block 3336, a warning message is displayed at the touch screen 104.

If it is determined that the barcode is a good barcode read at block 3312, the mechanical dispensing process 3300 continues to check if the corresponding bag or package is found at block 3340. If no corresponding bag is found, block 3324 is repeated. Otherwise, if a corresponding bag or package is found, the picker assembly grabs the found package and moves the package to a dispensing slot at block 3344. The barcode of the found package is scanned to verify against a prescription record at block 3348. If it is determined that there is a bad barcode read at block 3352, the mechanical dispensing process 3300 allows a number of repeated barcode reads starting at block 3348. In the embodiment shown, the barcode can be read a total of three times. If after three attempts (determined at block 3356), the prescription is assumed not to have been dispensed. If no barcode can be read, block 3324 is repeated. Otherwise, if it is determined that the barcode is a good barcode read at block 3352, the mechanical dispensing process 3300 terminates.

In some cases, a consumer may have prescriptions in both the unit 100 and behind the counter. The consumer can receive all the prescriptions without having to access the unit 100. Particularly, the consumer can go directly to the counter and requests that all the prescriptions are picked up at the counter. The pharmacy staff can then select a particular prescription electronically via the interface engine 2918, and open the unit 100 to remove the prescriptions. The pharmacy staff can also select the particular prescription electronically, and remove the prescription at a special dispensing slot, such as a back of the unit 100. In this way, the consumer can receive the prescriptions from the pharmacy staff directly. The unit 100 can also include a locker system such that large items or refrigerated items can also be dispensed through the unit 100, or by the pharmacy staff.

In some embodiments, the customer can be prompted to register in a registration process in order to use the services provided by the unit 100. During the registration process, customer can select to use the unit 100, or select not to use the unit 100. A flag that identifies a customer desiring to use the unit 100 is set or reset during the registration process. Particularly, each customer has an identity, and a flag is generally associated with the identity. When the customer desires not to use the services provided by the unit 100, the flag is either manually or electronically set such that the customer can be identified, for example, during a workflow process of filling a prescription. In such cases, the set flag will prompt some associated pharmacy staff that the prescription is destined for the unit 100. The registration process can either be a manual process where a consumer fills out a paper form and returns the filled paper form to the pharmacy to manually entered, or an electronic process where the consumer uses the touch screen 104 on the unit 100 to complete the form. In a case where the consumer uses the touch screen 104 on the unit 100 to complete the form, the unit 100 can set the flag. The registration process can also be a web-based process. The consumer can fill out the registration form on-line in a manner known in the art. Information that the registration process can require includes, but not limited to, date of birth, last name, street address, zip code, phone number, an answer to a selected question allowing the unit 100 to provide the consumer a hint question to remind the consumer of the password, and the like.

In some embodiments, the unit 100 also allows the consumer to assign a person other than the consumer to pick up, for example, the prescription. The consumer can be prompted to restrict access to a certain selected prescription for the person. For example, the consumer can restrict the person to pick up only a selected one of all the prescriptions that the consumer has ordered. Particularly, the consumer can destine a specific prescription by supplying a combination of a specific pharmacy number and some specific identifying information, or a specific password to the selected prescription, or to the rest of the prescription. In this way, when the person picks up the prescription for the consumer, the person can only have access to the one prescription assigned by the consumer, and the person will be unable to access or see the rest of the prescription. In some embodiments, the consumer can also assign the selected prescription to a particular consumer. In this way, the consumer grants access the selected prescription to the particular consumer, while the consumer can deny access to the rest of the prescription. Furthermore, granting access by assigning a selected prescription can also allow, for example, a parent to pick the selected prescription for his child as well as for himself.

In some embodiments, each of the pharmacy staff is authenticated before opening the unit 100. Generally, an audit trail of the pharmacy staff working with the unit 100 is logged. For example, each of the prescriptions that the pharmacy staff fills can be logged. For another example, each of the prescriptions to which the pharmacy staff has access can also be logged.

In some embodiments, when a prescription is a special item such as a new order, a refrigerated item, a large item, a bulky item, and the like, the prescription can be stored behind the counter. In such cases, even if a consumer has registered to use the unit 100, the consumer will be presented with a list of all the prescriptions available including the special item to the consumer on the touch screen 104. Particularly, the touch screen 104 can display the list of all the prescriptions available to the consumer, and can identify an item on the list that requires special attention with a note. For example, the note can direct the consumer where the consumer can pick up the item on the list. For example, the note can also direct the consumer to the pharmacy counter for any prescription not found in the unit 100.

In embodiments where pharmacist consultation is required, the unit 100 can be configured to only allow loading of refill prescriptions. In such cases, if a new prescription order is queued for filling and depositing into the unit 100, the new prescription order can be quarantined such that the consumer cannot access the new prescription order until after a consultation. In some other cases, if a new prescription order is queued for filling and depositing into the unit 100, a quarantine flag is set such that the new prescription order can be accessed after the pharmacy staff has reset the quarantine flag.

In some embodiments, the unit 100 can provide a phone number that the consumer can call to interact with the pharmacy staff on duty. The phone number can be provided in a combination of the touch screen 104, a receipt, and a prescription description included. The unit 100 can also be configured to include communication devices such as an intercom, a receiver therein such that the consumer can communicate with the pharmacy staff that can be located remotely from the unit 100.

Some states have limitations on the types of prescription that can be accessed through the unit 100. For example, some states have limitations on narcotics being accessible through the unit 100. In such cases, the unit 100 can be configured to have a prescription flag that can be set for some selected prescriptions. The unit 100 can be configured to reject any prescription whose associated prescription flag has been set, even if the flagged prescription is inadvertently loaded. In some cases, the unit 100 can be configured to set the prescription flag at manufacturing according to a destination state of the unit 100.

Furthermore, a prescription that continues beyond a year has to be rewritten by a physician in many states. After the prescription has been rewritten, the newly filled prescription is typically assigned a different prescription identification number. Because the rewritten prescription has a different prescription identification number, the rewritten prescription can sometimes be inadvertently considered as a new prescription that requires consultation. In such cases, the unit 100 can be configured to identify such a rewritten prescription, and to allow the rewritten prescription having a new prescription identification number to be dispensed to a consumer as if it were a refill without consultation. In some cases, after the prescription identification number has been assigned, the consumer may only have access to the original prescription number. However, the consumer typically will have to enter the new prescription identification number once the new prescription identification number has been assigned. In such cases, the unit 100 can be configured to allow the consumer to use either the original prescription number or the newly assigned prescription identification number such that the prescription can be dispensed. In some embodiments, the unit 100 can be configured to display both the original prescription number and the newly assigned prescription identification number along with the prescription name in the touch screen 104.

In many pharmacies, some over-the-counter ("OTC") items are kept behind the counter for security purposes. These OTC items are generally non-prescription items such as, without limitation, expensive merchandise, and "easily stolen" or "walk away" items. In such cases, the unit 100 can also be configured to store these items such that these items are available to consumers with or without a registered account. Furthermore, the unit 100 can provide an ability to pay for and then receive these non-prescription items.

Figure 29:
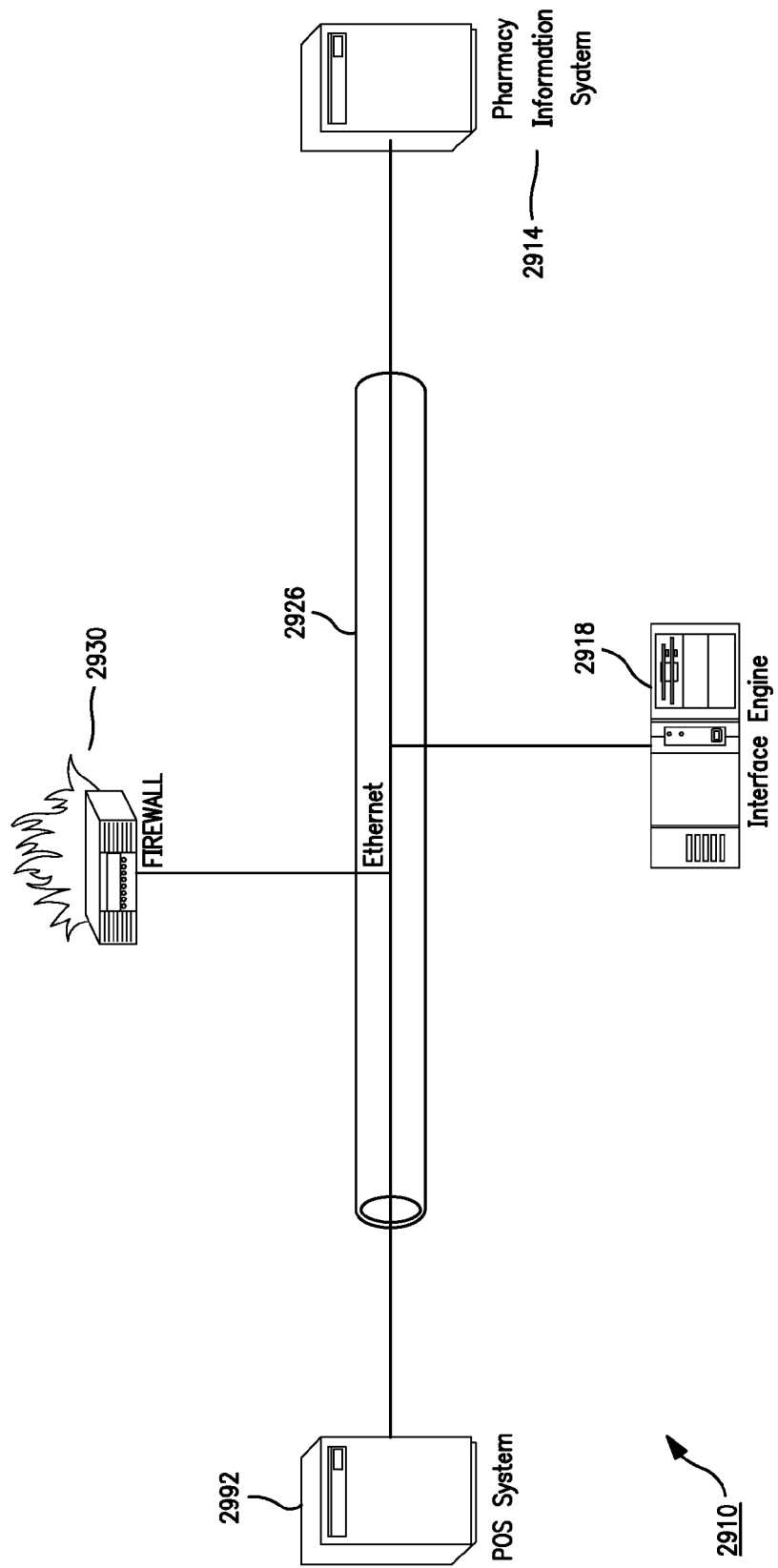
FIG. 29 shows an information networking system.

In some embodiments, purchases done on the unit 100 can be recorded in a point-of-sale ("POS") system or financial accounting system associated with a store or a pharmacy. To record the purchases, an interface of the unit 100 is coupled to the POS of the store. FIG. 29 shows an information system 2910 that illustrates an exemplary computer and network system within a typical pharmacy location or a pharmacy store. The information system 2910 includes a pharmacy information system 2914 that is coupled to an interface engine 2918 and a POS system 2922 of the pharmacy or the store via an Ethernet connection 2926. In some embodiments, the interface engine 2918 is a software-based interface engine. In such cases, software used on the interface engine 2918 and the POS system 2922 can be created by a particular vendor or the store running a particular operating system such as Windows XP. The interface engine 2918 can interface the pharmacy information system 2914 to receive all pharmacy prescription and order data, and to transmit purchase information to the POS System 2922. The information system 2910 also includes a router or firewall equipment 2930 that shields the information system 2910 from other networks, and allows the information system 2910 to communicate with the other networks in a manner know in the art. In this way, the store or the pharmacy can have secure access to the Internet through the router or firewall equipment 2930 for remote diagnostics, support, maintenance, and the like. In some embodiments, the unit 100 uses virtual private network ("VPN") technology to guarantee a secure point-to-point tunnel between the unit 100 and a central data processing center. Although an Ethernet is shown coupling items of the information system 2910, other networking systems can also be used. Operations of the information system 2910 will be discussed hereinafter.

In some embodiments, consumers need to know when their prescriptions are ready through the Internet. The information system 2910 can also provide secure web-based access to a consumer's information, including a status of any refills and whether those refills are available for pick up. Using the web-based access, the consumer can also pre-pay for their prescriptions. In this way, the consumers can simply pick up the prescription at the unit 100 without having to go through the payment process. In some embodiments, the pre-payment process can also be set up during the registration process that an associated credit card or bank account will be charged after the prescription is deemed ready to be picked up. Furthermore, a consumer can also designate another person to pick up the prescription via the web-based access.

In addition to the Ethernet 2926, other types of networking techniques such controller area network ("CAN") bus internal to the system 2910 and the unit 100 can also be used. The unit 100 can also include other networked devices such as distributed, and networked micro-controllers to control the robotics and the picker assembly, for example. Other electronics of the unit 100 include, without limitation, a pulsewidth modulated motor drive, motors with encoders, a feedback control of internal mechanisms such as speed and acceleration, a unique homing scheme in the unit 100 to minimize the use sensor bars or other elaborate position sensing, an intelligent distributed control with built in error recovery, a plurality of indicator lights and numeric readouts to notify pharmacy staff of machine status, on-board self diagnostics and error code readout, self diagnostics with intelligence to correct errors, efficient cabling, modular electronic design for rapid field service, magnetic door sensors, eStop and fail safe design, ability to email from internal electronics to internet email address, ability to reprogram firmware remotely, use of velocity, acceleration, and position sensing for intelligent feedback control, indicator lights on front of machine to improve communications to an end user, motor load sense and protection intelligence, and bag/product sensor and barcode scanner.

In some embodiments, the system 2910 and the unit 100 can also include a plurality of front-end capabilities. For example, if consumers need a secure place to submit paper prescriptions when the pharmacy is closed, a secure paper prescription drop off is built into the unit 100 allowing consumers to drop off the paper prescriptions and pharmacy staff to access them. For another example, if consumers need a means to get a prescription processed by an alternate fill location when the pharmacy is closed, the unit 100 contains a built-in scanner such that a consumer can feed in a paper prescription. The scanner can scan and securely capture the prescription. The unit 100 then answers specific information necessary to fill the prescription. The information is then sent electronically to a designated remote fill location for processing and then delivery back to the pharmacy for the consumers to pick up.

Figure 30:
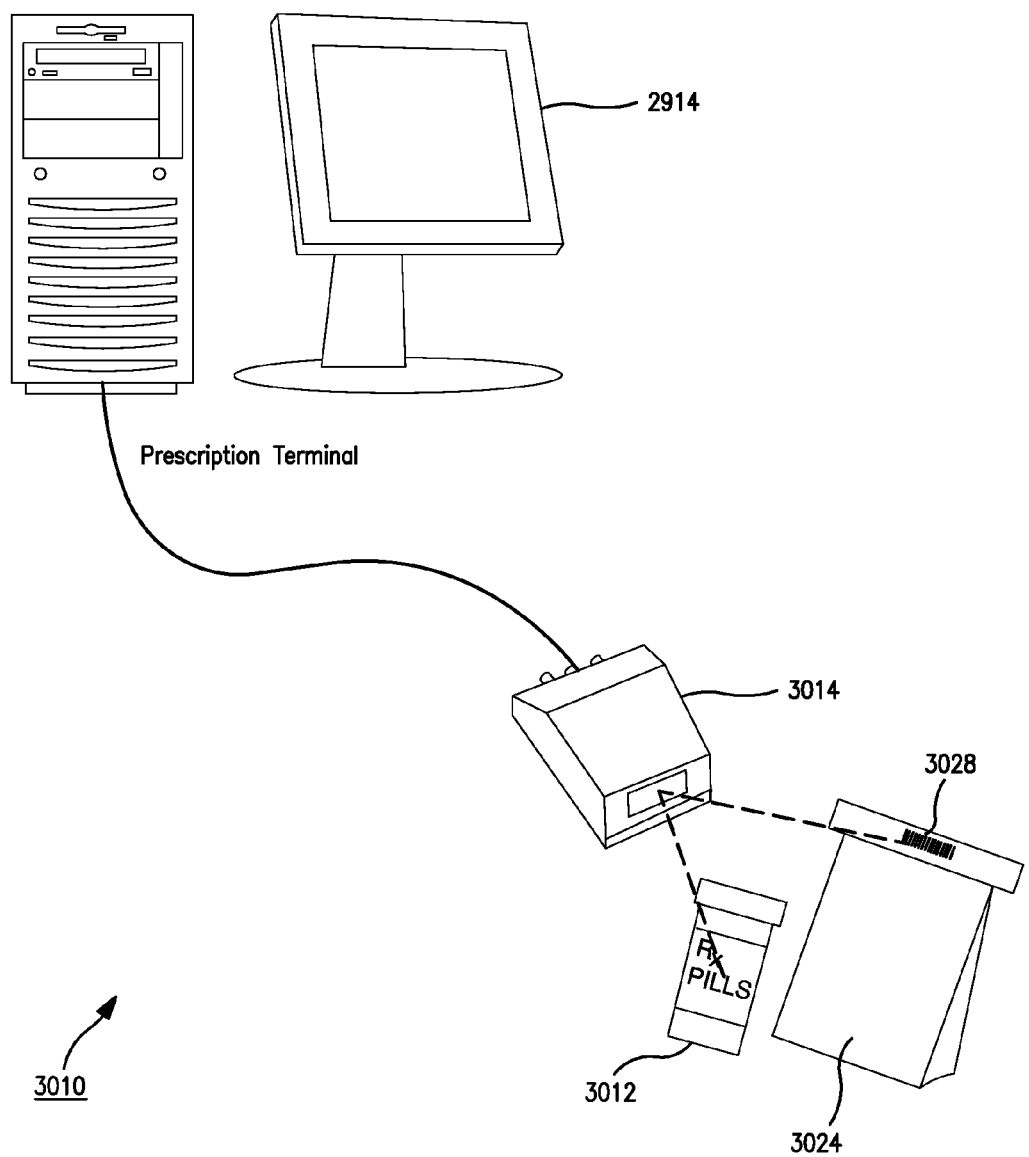
FIG. 30 shows a prescription preparation data flow.

After a prescription has been written, the prescription is then filled, labeled, and verified before being loaded in the unit 100 for dispensing. FIG. 30 shows a prescription preparation data flow 3010 that illustrates an exemplary prescription 3012 being filled, labeled, and verified by pharmacy staff in a plurality of locations within the pharmacy. After the pharmacy staff has received a prescription, the prescription can be entered into the pharmacy information system 2914. Associated records are subsequently sent to the interface engine 2918 for consumers who have registered with the information system 2910 to use self serve capability of the unit 100. In some embodiments, the records can also include, without limitation, patient name, patient address, patient phone, name of doctor and other third party information. In some other embodiments, the records can include a unique patient identification that can be shared between different units, patient fax numbers, patient email address, patient home phone, patient business phone, patient mobile phone, patient pager number, HIPAA flag as described earlier, and patient birthday. In some embodiments, the records can also include prescription data elements such as, without limitation, prescription number, refill number, fill date, maximum refills, quantity ordered, store number, insurance information, Medicaid information, co-pay information, co-pay amount, non-child resistant packaging information, and last prescription information if any. Like any prescriptions, the records can also include medication elements such as, without limitation, drug name, drug code, tax information, brand name, generic name, retail price, fill cost, drug cost, physician information, and physician contact information. The pharmacy staff also uses the pharmacy information system 2914 and a scanner 3014 to manually verify the filled prescription 3012 against the prescription record by scanning a barcode 3018 on a dispenser bag 3024. If an error or an exception occurs during transmission, a message is displayed on the pharmacy information system 2914.

In some embodiments, the unit 100 through the touch screen 104 displays to the consumer all prescriptions that are processed in the pharmacy including items that are purchased outside of the unit 100. The interface engine 2918 can be configured to provide feedback information when the prescription has been purchased outside of the unit 100. In this way, the unit 100 can remove the prescription from the list displayed to the consumer thereby avoiding confusion. Similarly, prescriptions that are voided or otherwise deleted are also communicated via the interface engine 2918 such that the unit 100 can also remove those items from the list displayed to the consumer. Furthermore, if a consumer has not picked up his or her prescription in a predetermined amount of time, the prescription will be returned to the return tray 552, detailed hereinafter. In such cases, the interface engine 2918 can also provide a notification that the prescription has been returned, for example.

In some embodiments, the pharmacy information system 2914 can update prescription information without requiring the prescription be voided and refilled or rewritten. As a result, third party information such as insurer, the retail price, or the co-pay can also change. In such cases, the unit 100 generally queries the pharmacy information system 2914 via the interface engine 2918 for the most recent information regarding the prescription just prior to displaying the information to the consumer. In this way, the most current information is available to the consumer. Still furthermore, when a client uses a pharmacy information system 2914 from a vendor, it is often difficult and timely to get an interface written. In such cases, the existing interface engine 2918 can be adapted to interface with other systems such as bulk pill counters/dispensers, voice automated refill ("IVR"), instead of developing a new interface. In some cases, an IVR interface does not always provide sufficient data because the IVR interface is generally reactive. As a result, only information on a prescription is available when requested and some important fields like non-child resistant cap, and the co-pay or the retail price are unavailable. The interface engine 2918 can be augmented with another interface of the vendor. In such cases, information going to the label printer can be captured and thus can be used to augment data missing from the IVR interface.

In some embodiments, the pharmacy staff needs to identify between prescriptions that go into the unit 100 and those that should be kept somewhere else. In such cases, during the process of filling a prescription or a loading process 3140, a notice can be displayed in the form of a dialogue box, a color coded screen form, and the like to inform the pharmacy staff that if the prescription is to be placed in the unit 100. Particularly, a set registration flag is used to trigger such a notice to be displayed.

In some embodiments, the pharmacy staff needs to marry or to match a prescription to a dispenser bag. In such cases, after a prescription has been filled and before it can go into the unit 100, the prescription is matched with the dispenser bag. The process of matching starts with scanning a barcode of the prescription and a barcode on the dispenser bag, as discussed. In this way, the barcode of the description bag is matched with the barcode of the prescription, which links to a database record with the details of the prescription.

Figure 31:
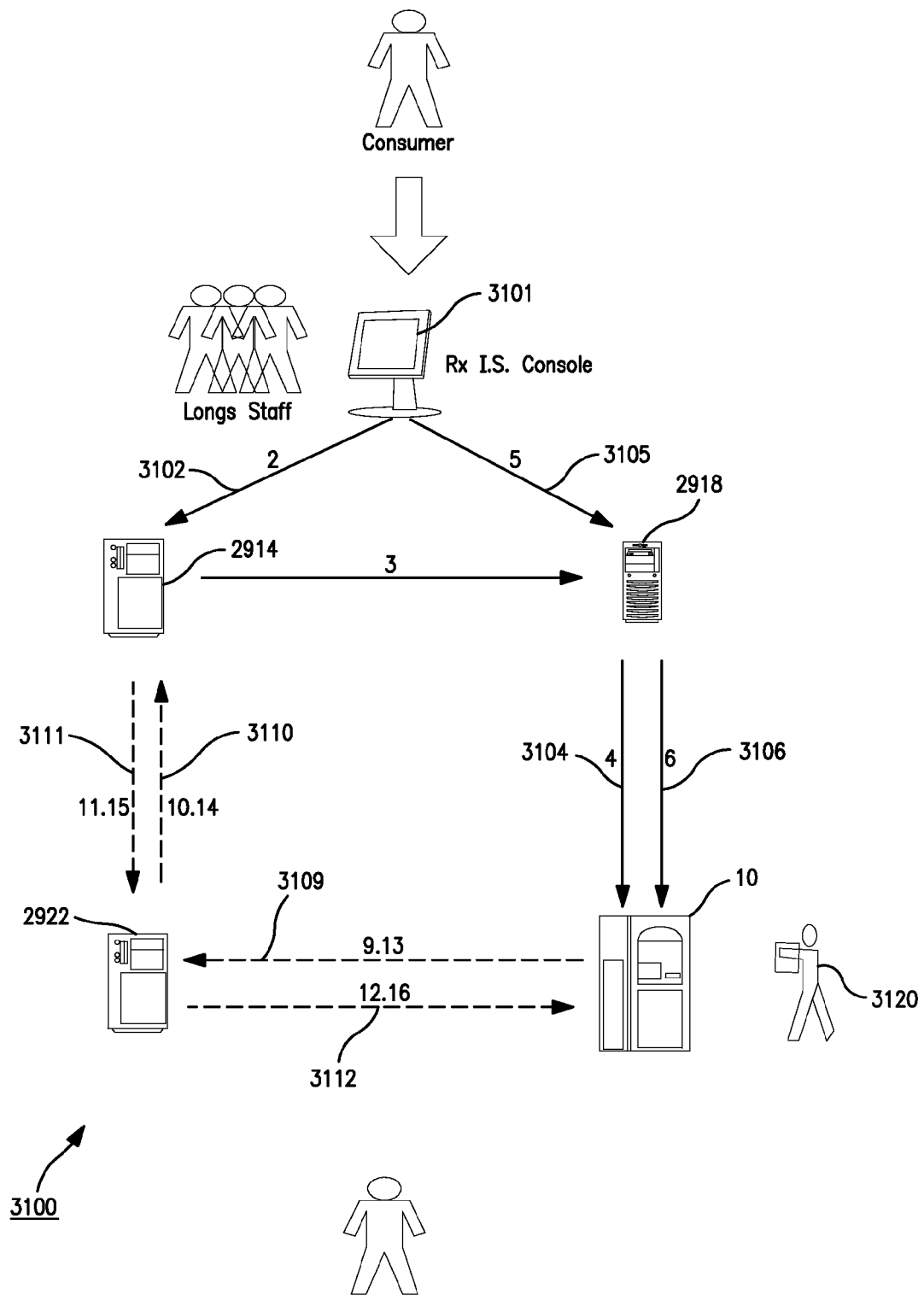
FIG. 31 shows an exemplary data flow when a consumer requests for a refill prescription to be put in the dispensing unit of FIG. 1.

FIG. 31 shows an exemplary data flow 3100 when a consumer requests for a refill prescription to be put in the unit 100. Particularly, when the pharmacy staff enters the written refill prescription and patient information at a dispensing screen 3101 where the entered information is stored in the pharmacy information system 2914 at step 3102. The pharmacy information system 2914 checks to see the consumer is a registered customer. If the consumer is a registered customer, the pharmacy information system 2914 then sends the prescription record to the interface engine 2918 at step 3103. The interface engine 2918 then sends the prescription record to the unit 100 at step 3104, while the pharmacy staff fills the prescription and puts the prescription 3012 into the dispenser bag 3024 and scans the barcode 3018 at step 3105. The interface engine 2918 then sends the scanned barcode to the unit 100 at step 3106 while a pharmacy technician 3120 places the bagged prescription in the unit 100. In some embodiments, the pharmacy information system 2914 will display a popup window to allow the pharmacy staff to scan a bag number associating the prescription with the bag 3024. However, when the prescription is returned to stock, the pharmacy information system 2914 will send a transaction to interface engine 2918 to mark the prescription as a return, and the unit 100 will flag the prescription as cancelled and put the bag 3024 in a return bin. When the prescription is voided, pharmacy information system 2914 will send a transaction to interface engine 2918 to mark the prescription as a void, and the unit 100 will flag the fill as cancelled and put the bag 3024 in the return bin.

Referring back to FIG. 31, when the consumer comes to pick up the bagged prescription, the unit 100 sends a prescription number associated with the prescription to the POS system 2922 at step 3109. The POS system 2922 then requests information such the prescription price from the POS system 2922 to the pharmacy information system 2914 at step 3110. In turn, the pharmacy information system 2914 sends the requested information such as the prescription price back to the POS system 2922 at step 3111. The POS system 2922 subsequently send the prescription price back to the unit 100 at step 3112. The unit 100, after receiving the prescription price from the POS system 2922, sends out a prescription transaction back to the POS system 2922. The POS system 2922 also sends the prescription transaction to the pharmacy information system 2914 which in turn sends a confirmation back to the unit 100 through the POS system 2922.

During the transaction, if the consumer selects to pay for the prescription with a credit card, the consumer can be prompted on the touch screen 104 to slide a credit card through the credit card reader 106. The transactions will then be reported from the unit 100 to the POS system 2922 and other financial institutions through the interface engine 2918. In some embodiments, the unit 100 can be configured to accept debit cards whose pin numbers can be entered on the keypad, and gift cards which can be read by the magnetic stripe reader 105. In embodiments where the consumer wishes to pay for the prescription with a radio-frequency ("RF") based credit or debit token such a speed pass, the unit 100 can be configured to include an RF speed pass reader can be interfaced to the POS system 2922. If the consumer logins to the unit 100 with a credit card, the unit 100 can automatically use the credit card information as default payment information, or displays some options to the consumer with the touch screen 104, without requiring the consumer to stripe the credit card again. However, if the consumer selects to pay for the prescription with cash, the POS system 2922 accepts the cash with a cash acceptor, and prints a receipt for the transaction for the cash.

Figure 32:
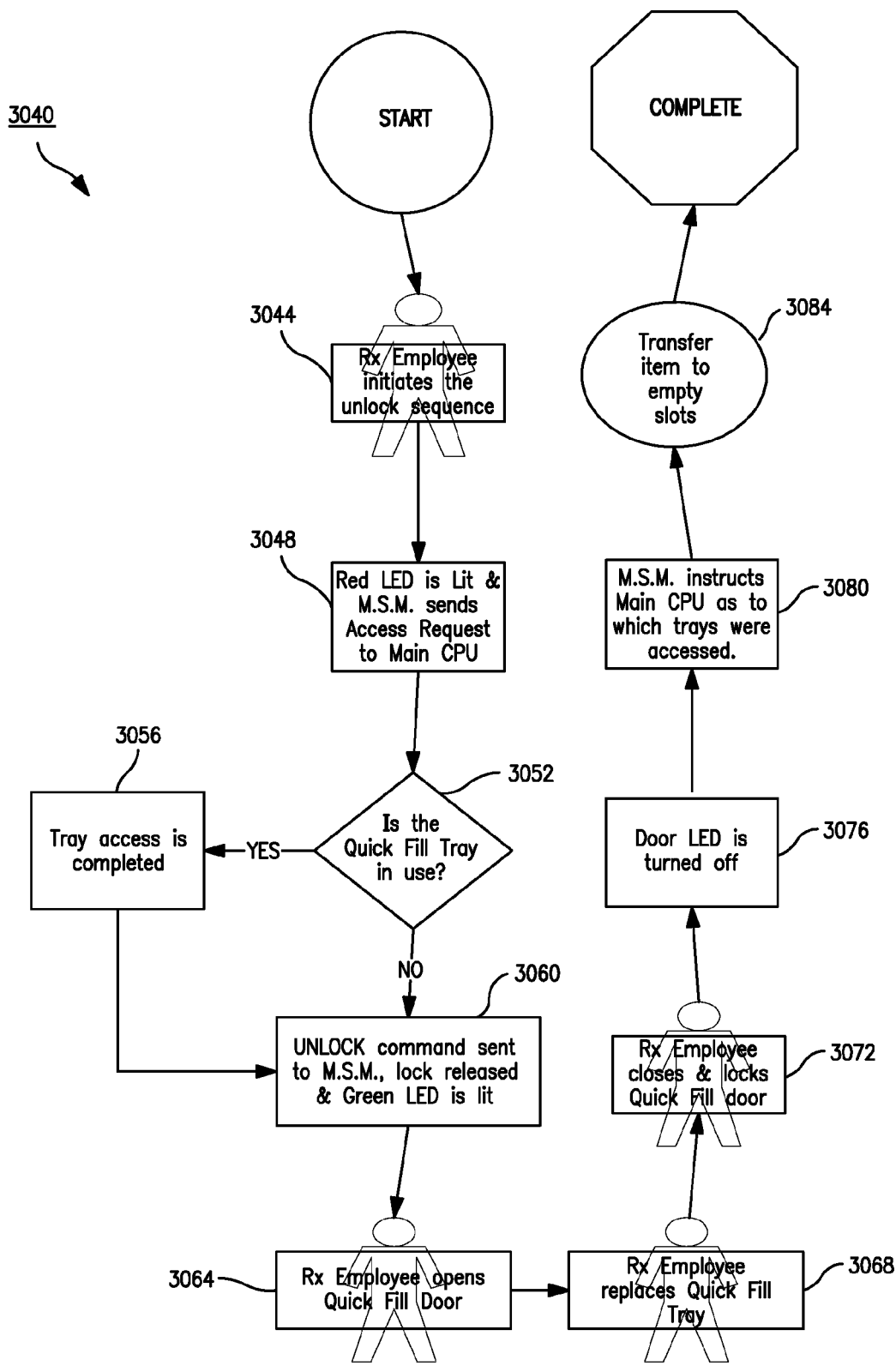
FIG. 32 shows a flow chart illustrating an exemplary quick loading or filling process.

There are times when some prescriptions need to be loaded quickly, the unit 100 also includes a quick load process. In the quick load process provides the pharmacy staff with an access to a single quick fill tray within the unit 100 without having to open a back door of the unit 100. Periodically during the day, inventory can also be added to the unit 100 by simply swapping trays. For example, an old quick fill tray can be swapped with a new quick fill tray filled with items. Once loaded in the unit 100, the unit 100 can automatically move the newly deposited items in the quick fill tray to empty slots. FIG. 32 shows a flow chart illustrating an exemplary quick loading process 3020. The quick loading process 3040 starts when the pharmacy staff initiates an unlock sequence on the unit 100 at block 3044. Like the loading process 3140, a red LED is lit, and the MSM sends a request to access the unit 100 at block 3048. The quick loading process 3040 determines if a quick fill tray is in use at block 3052. If the quick fill tray is being used, the pharmacy staff has to wait for the tray access to be completed at block 3056. Once the quick fill tray is available, the quick loading process 3040 sends an unlock request to the MSM, the quick fill tray lock is released, and an associated green LED is lit at block 3060. Once the pharmacy staff opens the quick fill tray door at block 3064, the pharmacy staff can replace the quick fill tray at block 3068, locks the quick fill tray at block 3072, respectively. The quick fill tray LED is turned off at block 3076, and the MSM instructs the main processor that the quick fill trays were accessed at block 3080. Thereafter, items in the quick fill tray are transferred to empty slots in other trays in the unit 100 at block 3084.

Figure 33:
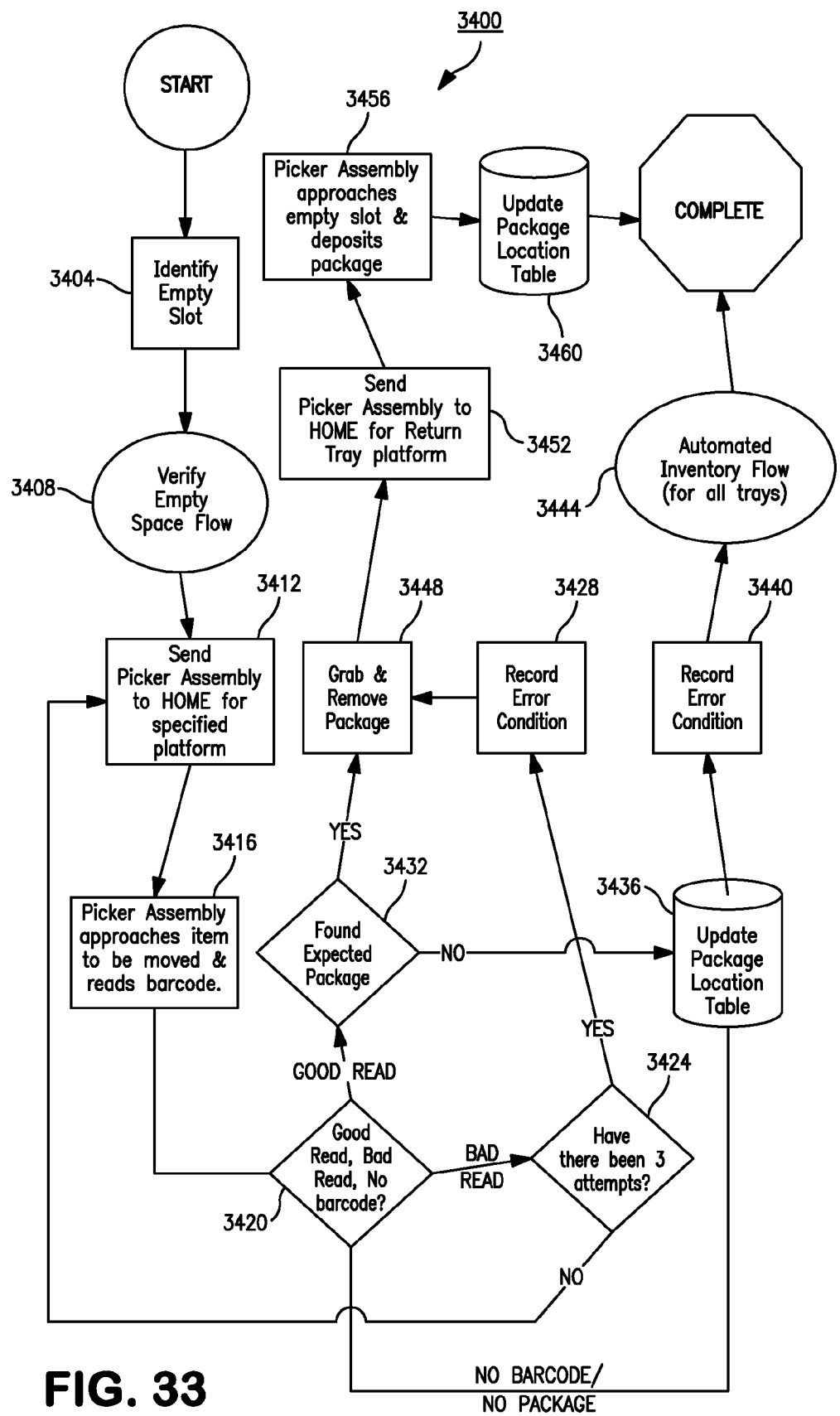
FIG. 33 shows an exemplary transfer process for returning prescription to a return tray.

FIG. 33 shows an exemplary transfer process 3400 for returning prescription to a return tray or an empty slot within a tray designated as a return tray. Particularly, the unit 100 identifies if there is an empty slot available at block 3404. Thereafter, the coordinates of an empty slot are returned from block 3408, detailed hereinafter. The transfer process 3400 then sends the picker assembly to home at block 3412 to reset the coordinates. At block 3416, the picker assembly is moved to the prescription coordinates at which the item is to be transferred. The barcode of the coordinates is also read at block 3416. If it is determined that the barcode is a bad barcode read at block 3420, the transfer process 3400 allows a number of repeated barcode reads starting at block 3412. In the embodiment shown, the picker assembly can read the barcode a total of three times. If after three attempts (determined at block 3424), the error condition is recorded at block 3428. If it is determined that the barcode is a good barcode read at block 3420, the transfer process 3400 continues to check if an expected package is found at block 3432. If the expected package is not found, a package location table of the unit 100 is updated at block 3436, the error condition is also recorded at block 3440, and an automated inventory process for all trays is initiated at block 3444, detailed hereinafter.

If the expected package is found, the picker assembly then grabs and removes the package from the coordinates at block 3448. The picker assembly is then moved back to home coordinates of the designated return tray at block 3452, and subsequently moved to the empty slot coordinates at block 3456, respectively. The package location table of the unit 100 is updated at block 3460.

In some embodiments, part of the unit 100 requires that items or packages therein to be able to move around with the picker assembly. However, items or packages can become jammed or other issues can arise. The unit 100 can be configured to detect such problems. Particularly, the unit 100 checks the barcode on a package at its location before and after moving it. The unit 100 also has a robotic assembly that sweeps the top of the trays where packages have been moved in order to seat or reseat anything that is slightly askew. The sweep can also forcibly cause some jamming in the trays. After trying to correct or force an error, the unit 100 then re-scans all barcodes of the moved items to verify that items are accurately slotted. In this way, the unit 100 will not be back in service for consumer use before the jammed items are removed thereby preventing consumer use and alerting pharmacy and support personnel of the problem.

Figure 34:
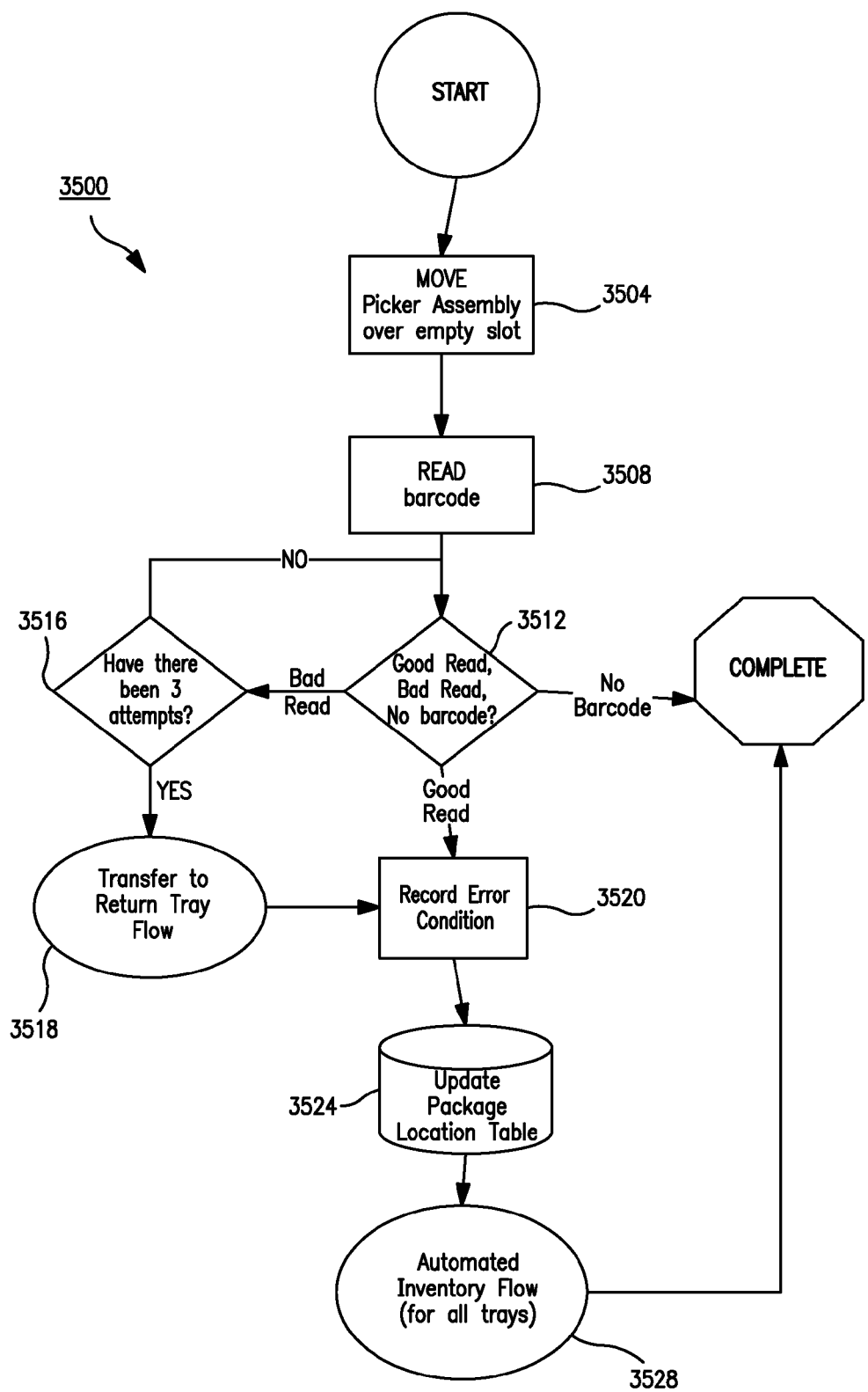
FIG. 34 shows a flow chart illustrating an exemplary empty slot verification process.

During the transfer process, an empty slot is to be located and verified to be empty. FIG. 34 shows a flow chart illustrating an exemplary empty slot verification process 3500. The picker assembly is moved over to a slot that is indicated empty in the package location table at block 3504. The barcode of the slot is then scanned at block 3508. Again, if it is determined that the barcode is a bad barcode read at block 3512, the empty slot verification process 3500 allows a number of repeated barcode reads starting at block 3512. In the embodiment shown, the barcode is read a total of three times. If after three attempts (determined at block 3516), the empty slot verification process 3500 returns an error to the transfer process 3400 at block 3518, and the error condition is recorded at block 3520. If it is determined that the barcode is a good barcode read at block 3512, the error condition is recorded at block 3520 again. After the error condition has been recorded, the package location table of the unit 100 is updated at block 3524, and the automated inventory flow process is initiated at block 3528. If no barcode is read, the empty slot verification process 3500 terminates.

Figure 35:
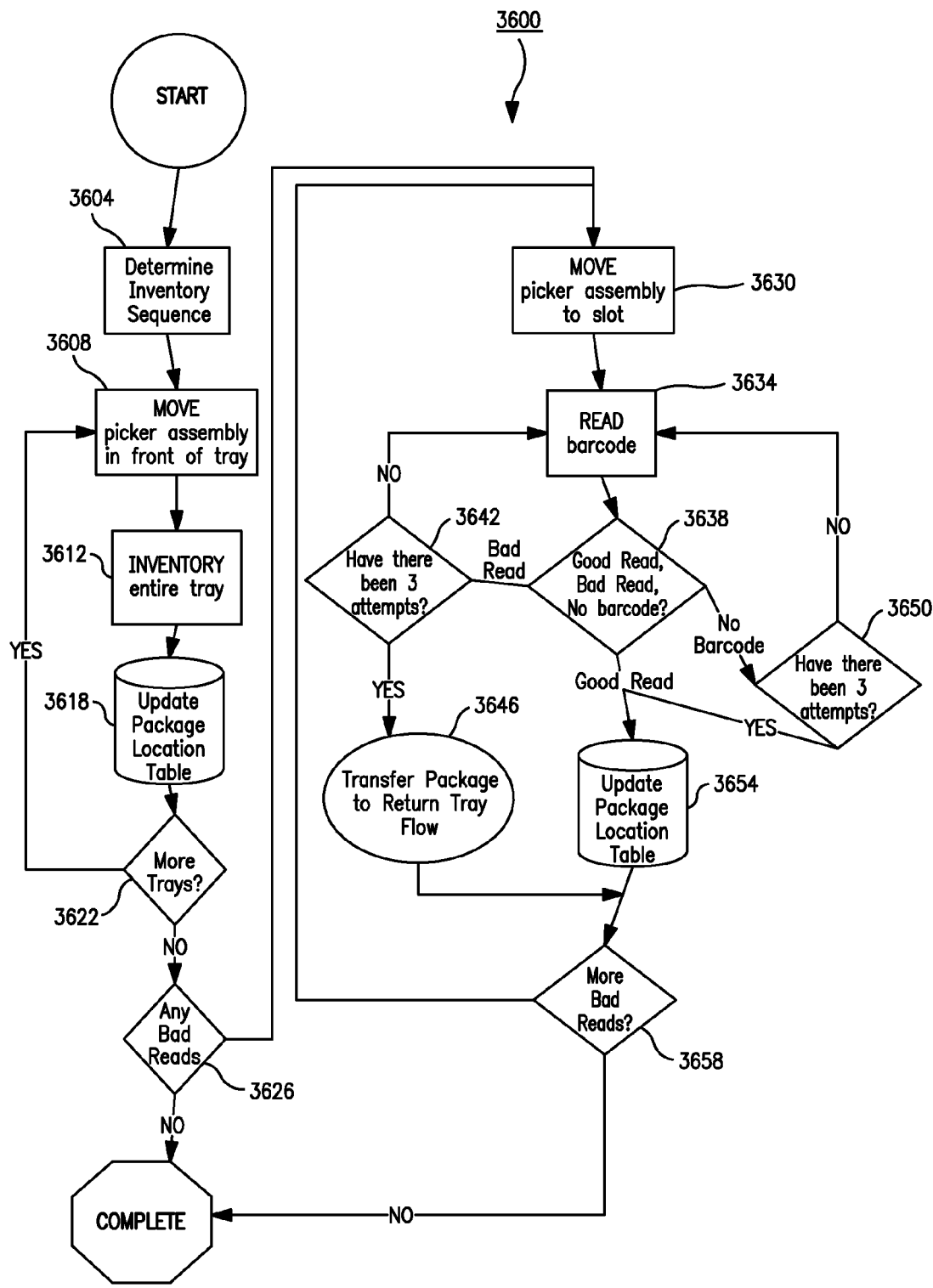
FIG. 35 shows a flow chart illustrating an exemplary automated inventory flow process.

As part of a loading process and the transfer process 3400, each of the trays that were accessed can be re-inventoried. FIG. 35 shows a flow chart illustrating an exemplary automated inventory flow process 3600. The automated inventory flow process 3600 starts by determining an inventory sequence at block 3604. The picker assembly is then moved to a front of the tray according to the inventory sequence at block 3608. Since each tray contains a plurality of slots, all slots are inventoried at block 3612, and the package location table of the unit 100 is updated at block 3618. If there are more than one tray in the unit 100 as determined at block 3622, and block 3608 is repeated. If there is no more trays to be inventoried, the automated inventory flow process 3600 continues to check if there are any bad reads. If there are no bad read determined at block 3626, the automated inventory flow process 3600 terminates.

If there are any bad read, the automated inventory flow process 3600 moves the picker assembly to the slot that has a bad barcode read at block 3630, and the barcode is read at block 3634. Again, if it is determined that the barcode is a bad barcode read at block 3638, the automated inventory flow process 3600 allows a number of repeated barcode reads starting at block 3634. In the embodiment shown, the barcode can be read a total of three times. If after three attempts (determined at block 3642), the automated inventory flow process 3600 returns an error to the transfer process 3400 at block 3646. If there is no barcode read from the slot determined at block 3650, the automated inventory flow process 3600 allows a number of repeated barcode reads starting at block 3634. If it is determined that the barcode is a good barcode read at block 3512, the package location table of the unit 100 is updated at block 3654. If there are more bad barcode reads determined at block 3658, the automated inventory flow process 3600 repeats at block 3630.

The re-inventoried unit 100 can also generate a report that can be accessed by other systems in the network. For example, an inventory report that, for example, automatically collates all the items in the unit 100 can be provided to users by the unit 100, or systems such as the pharmacy information system 2914. In some embodiments, the pharmacy information system 2914 can also generate a third party log that reproduces a report that can include sorted and filtered data for specific dates and insurers, for example.

Furthermore, the unit 100 can also notify a consumer when a prescription is ready to be dispensed. For example, the unit 100 can generate automated phone call to numbers provided by the consumer during registration, text messages to cell phone, email messages to email addresses, and the like. Based on the information available via the interface engine 2918, the unit 100 can also notify a consumer when prescription stored in a will-call section has been filled, and is available to be picked up using means described earlier.

Figure 36:
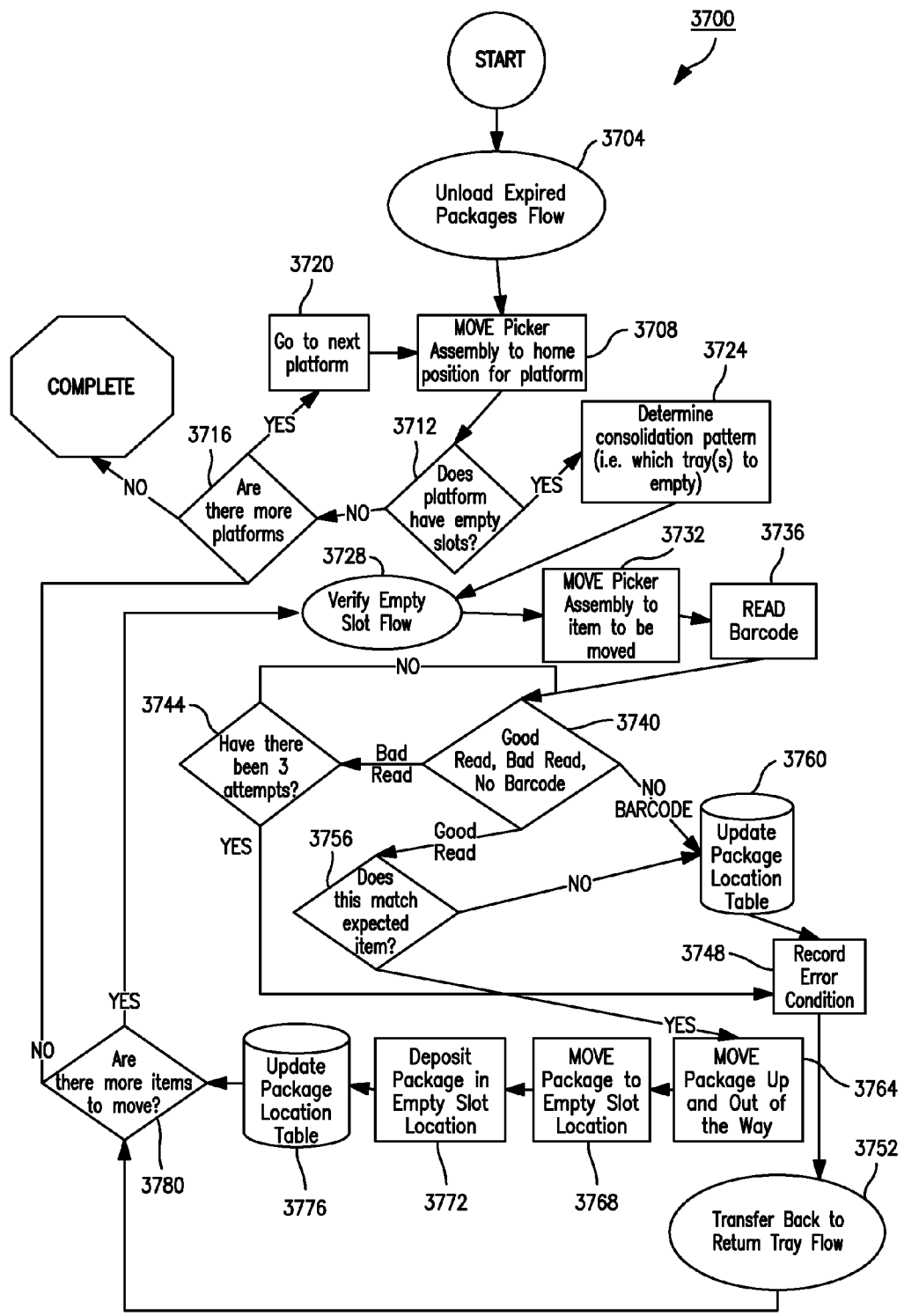
FIG. 36 shows a flow chart illustrating an exemplary consolidation process.

Consolidation of the trays allows the unit 100 to move around the bags to create contiguous empty slots with a primary intent of creating entirely empty trays. FIG. 36 shows a flow chart illustrating an exemplary consolidation process 3700. The consolidation process 3700 starts with unloading all expired packages at block 3704, detailed hereinafter. The consolidation process 3700 then move the picker assembly to the home position or coordinates at block 3708, and checks to determine if there are any empty slots in the trays or platforms at block 3712. If there are no more trays to check as determined at block 3716, the consolidation process 3700 terminates. If there are more trays to check as determined at block 3716, the consolidation process 3700 moves the picker assembly to a next tray starting at block 3720.

If there are empty slots in the trays or platforms determined at block 3712, the consolidation process 3700 determines a consolidation pattern at block 3724. For example, the consolidation pattern can consider which tray to empty first in some embodiments. Thereafter, the consolidation process 3700 checks for empty slots at block 3728, and starts to move the picker assembly to slots that are occupied at block 3732. Once the picker assembly is moved into position, the barcodes of the occupied slots are read at block 3736. If it is determined that the barcode is a bad barcode read at block 3740, the consolidation process 3700 allows a number of repeated barcode reads starting at block 3740. In the embodiment shown, the barcode is read a total of three times. If after three attempts (determined at block 3744), the consolidation process 3700 records the error condition at block 3748, and transfers the bags to the return tray at block 3752, as described earlier. If it is determined that the barcode is a good barcode read at block 3740, the consolidation process 3700 checks to determine if the bag in the occupied slot matches the expected item listed in the package location table at block 3756. If there is no match between the expected item and the barcode scanned, or if there is no barcode at all, the package location table is updated at block 3760. However, if the expected item matches the bag in the occupied slot, the consolidation process 3700 removes the bag from the occupied slot at block 3764, moves the bag in the empty slot at block 3768, and deposits the bag into the empty slot at block 3772, respectively. Thereafter, the package location table is updated at block 3776, and the consolidation process 3700 checks to determine if there are more items to move at block 3780. If there are more items to more, block 3728 is repeated; otherwise, block 3716 is repeated if there are more platforms to check.

Figure 37:
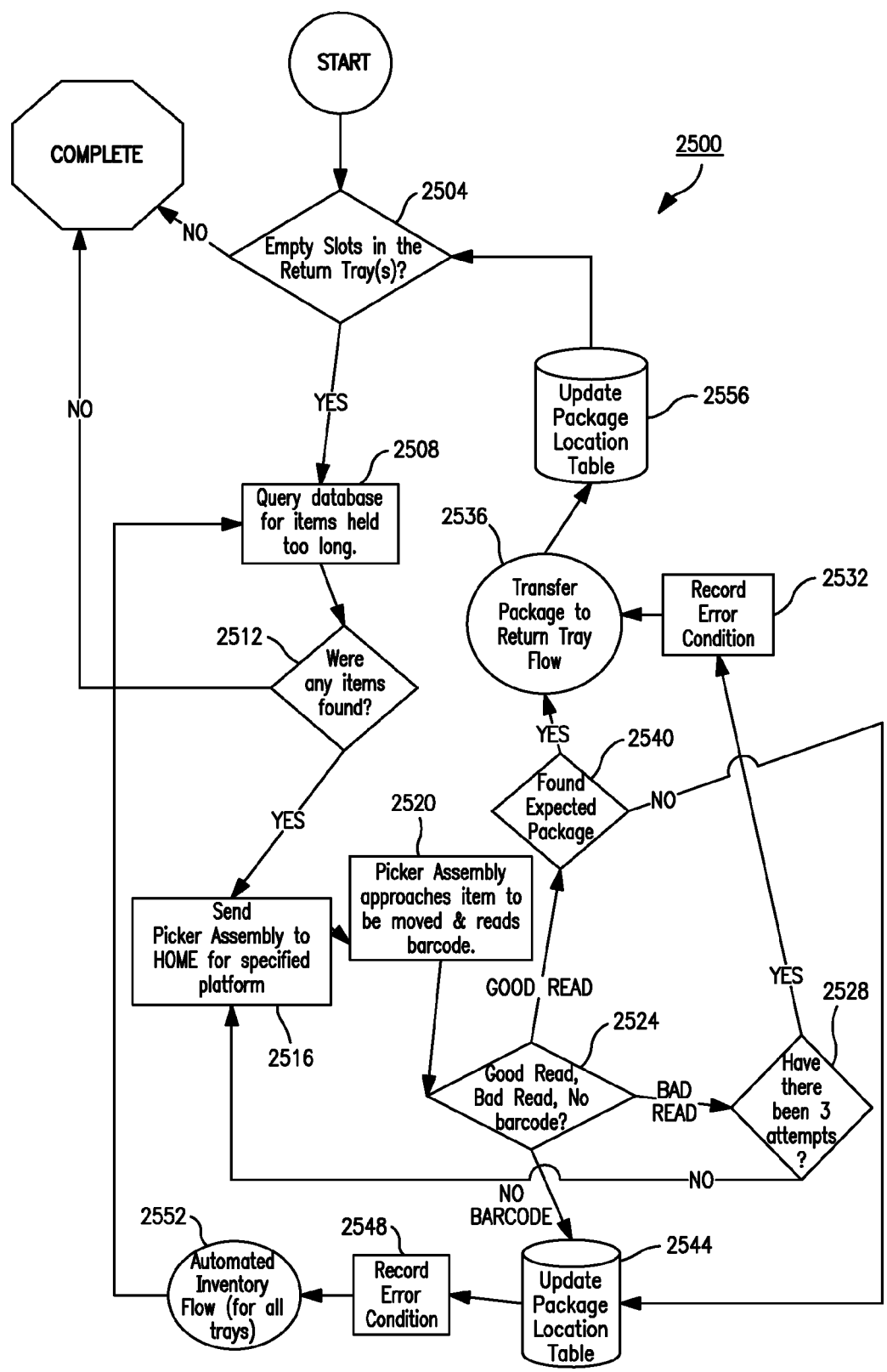
FIG. 37 shows an exemplary unloading process.

The unit 100 can also unload expired packages. In some embodiments, the unit 100 provides an option to record and determine how long a package is allowed to remain in the unit 100 if the consumer has yet to pick up the package. During housekeeping, packages that have exceeded a predetermined amount of time are removed in the return bin 552. FIG. 37 shows an exemplary unloading process 2500 that starts with determining if there are empty slots in the return bin 552 at block 2504. If all slots of the return bin 552 are occupied, the unloading process 2500 terminates. Otherwise, if some slots of the return bin 552 are available, the unloading process 2500 continues to query a computer database for items that are expired at block 2508. In some embodiments, the unloading process 2500 uses a predetermined amount of time to determine if an item is expired. If the unloading process 2500 determines, at block 2512, that there is no expired item, the unloading process 2500 terminates.

If the unloading process 2500 determines that there is expired item, the unloading process 2500 sends the picker assembly to the home position at block 2516. Thereafter, the picker assembly locates the coordinates of the expired item from the database, approaches the expired item, and read the barcode of the expired item at block 2520. If it is determined that the barcode read is bad at block 2524, the unloading process 2500 allows a number of repeated barcode reads starting at block 2520. In the embodiment shown, the barcode is read a total of three times. If after three attempts (determined at block 2528), the unloading process 2500 records the error condition at block 2532, and transfers the bags to the return tray at block 2536, as described earlier. If it is determined that the barcode is a good barcode read at block 2524, the unloading process 2500 checks to determine if the bag in the occupied slot matches the expected item listed in the package location table at block 2540. If there is no barcode at all, the package location table is updated at block 2544, and the error condition is recorded at block 2548, respectively. Thereafter, an automated inventory is initiated at block 2552, and the unloading process 2500 repeats at block 2508. When the found package matches the expected package at block 2540, the unloading process 2500 transfers the package to the return tray 552 at block 2536. The package location table is updated at block 2556, and the unloading process 2500 returns to block 2504.

Figure 38:
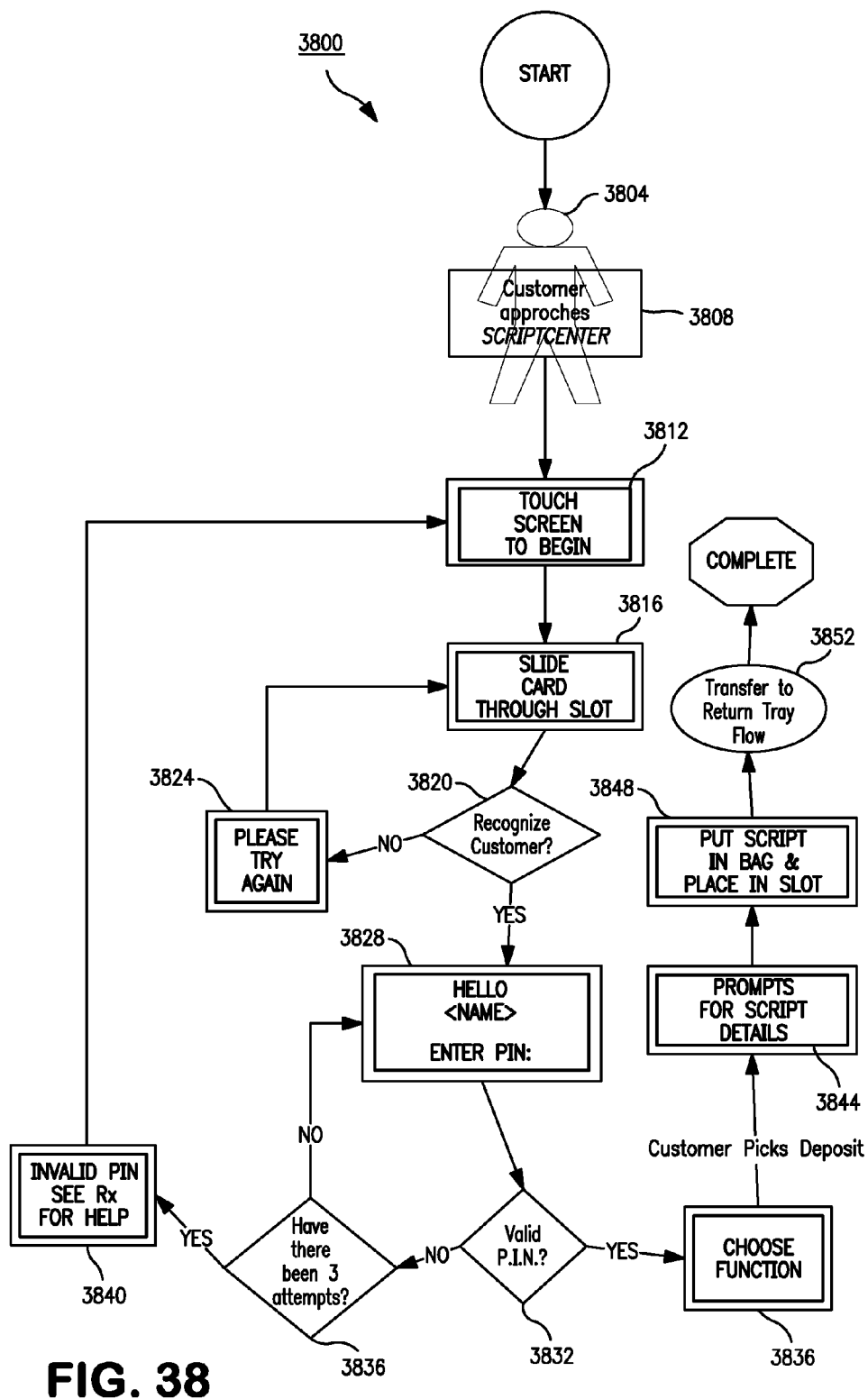
FIG. 38 shows a flow chart illustrating an exemplary prescription deposit process.

In some embodiments, the unit 100 can be configured to allow depositing prescription. FIG. 38 shows a flow chart illustrating an exemplary prescription deposit process 3800 that starts with a consumer 3804 approaching the unit 100 at block 3808. The consumer 3804 can touch the touch screen 104 to begin the prescription deposit process 3800 at block 3812. The consumer 3084 can slide an identification card or a credit card through the card reader 106, or other means discussed earlier, at block 3816 to identify the consumer. The unit 100 then determines if the consumer is a registered consumer, or simply attempts to recognize the consumer at block 3820. If the unit 100 cannot identify the consumer 3804, the prescription deposit process 3800 repeats at block 3824 to identify the consumer.

If the unit 100 identifies the consumer 3804, the prescription deposit process 3800 goes into a login mode at discussed before at block 3828 to prompt for a password or other information. If the password is valid (as determined at block 3832), the prescription deposit process 3800 continues at block 3836. However, if the password is considered invalid (determined at block 3832), the unit 100 will repeat block 3828 to prompt for another password for a number of times. In the embodiment shown, the unit 100 will continuously prompt for a valid password for three times, determined at block 3836. If after the third attempt, and if the password is still invalid, an invalid password message is displayed at block 3840, a message directing the consumer 3804 to see the pharmacy staff is also display at block 3840, and the prescription deposit process 3800 restarts at block 3812.

At block 3836, the consumer 3804 is prompted to enter a specific function desired. After the consumer 3804 has selected to deposit a prescription, the touch screen 104 then prompts for details of the prescription at block 3844. The consumer 3804 is then directed to put the prescription in a bag and deposit the bag in a deposit slot at block 3848. The deposited bag is moved into the return tray 552 at block 3852.

Figure 39:
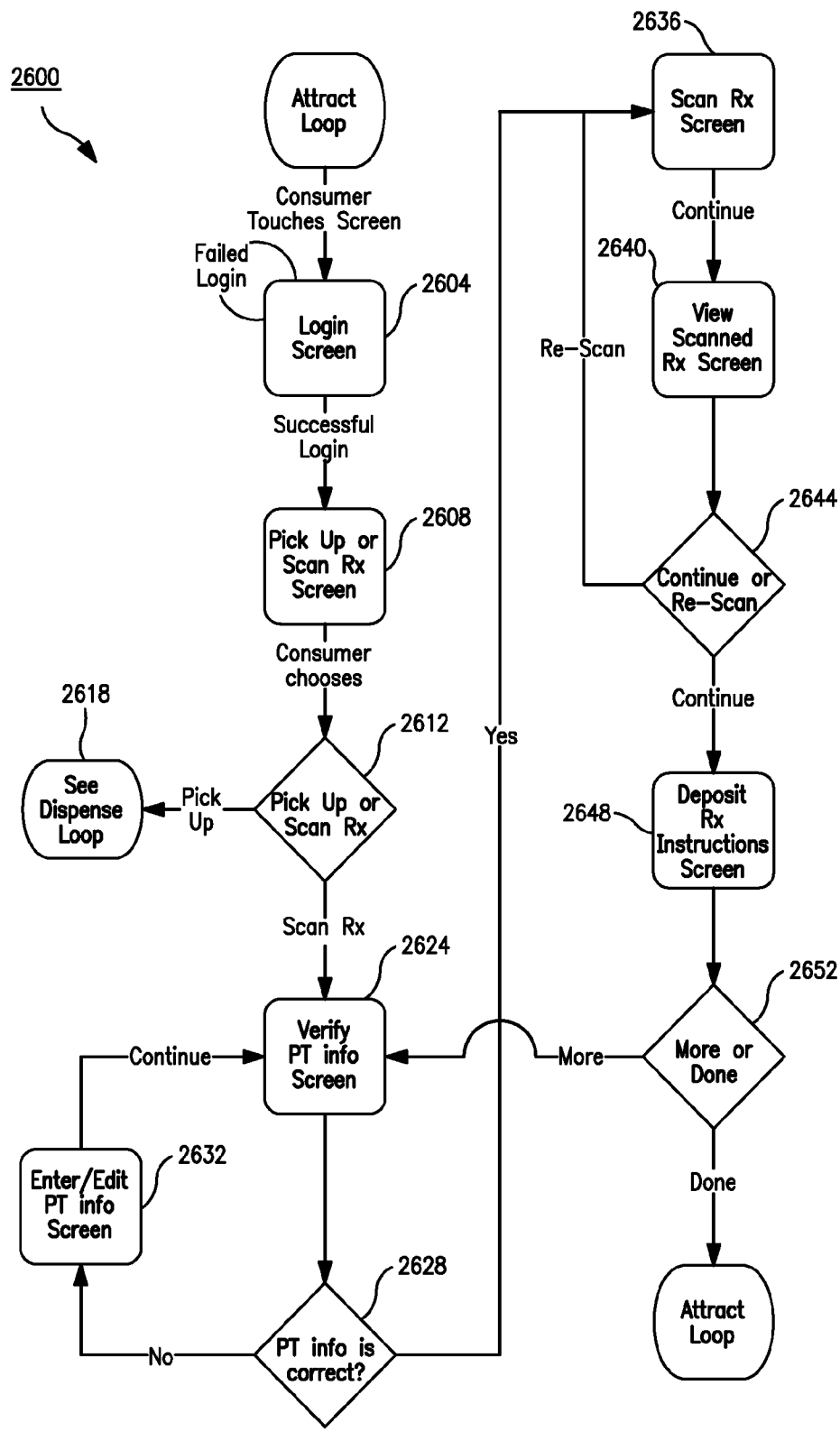
FIG. 39 shows an alternate flow chart illustrating an exemplary deposit process.

FIG. 39 shows an alternative deposit process 2600 that starts with a consumer touching the touch screen 104 and accessing a login screen at block 2604. After a successful login by the consumer in a manner similar to the description above, the touch screen 104 lists a plurality of options including prescription pick up or prescription drop off at block 2608. If the consumer selects prescription pick up at block 2612, the alternative deposit process 2600 is transferred to the dispense process 3200 of FIG. 26. Otherwise, if the consumer selects prescription drop off for scanning purposes, the alternative deposit process 2600 continues at block 2624 that verify information relating to the consumer. If the consumer information is incorrect as determined at block 2628, the consumer will be prompted to edit the information at block 2632. Otherwise, if the consumer information is considered correct, the alternative deposit process 2600 continues at block 2636 that scans in the prescription that the consumer drops in a deposit slot as described earlier. The scanned prescription is displayed at block 2640, and block 2636 is repeated until the prescription is correctly scanned in, determined at block 2644. Thereafter, the alternative deposit process 2600 prompts for additional prescriptions at block 2648. If there is more prescription as determined at block 2652, the alternative deposit process 2600 repeats at block 2624. If there is no more prescription, the alternative deposit process 2600 terminates.

Figure 40:
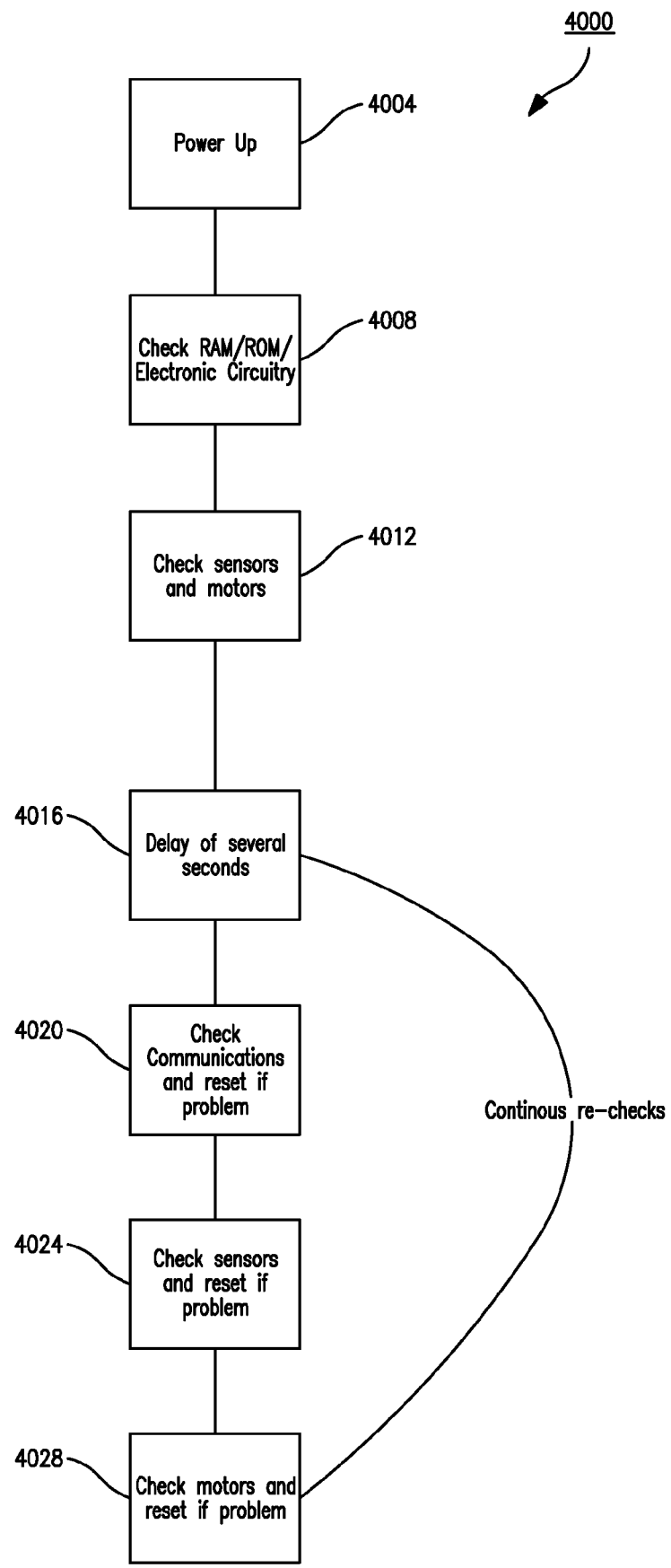
FIG. 40 shows an exemplary power up process.

FIG. 40 shows a power-up self-check process 4000 used by the unit 100. After the unit 100 is powered up at block 4004, the unit 100 checks its memory including RAM and ROM, and its circuitry at block 4008. Thereafter, the unit 100 checks its sensors and motors at block 4012. The unit 100 is then kept at idle for several seconds at block 4016. After the idle delay, the unit 100 checks its communication and resets if any problem is detected at block 4020. If the communication does not have any problems, the unit 100 checks a set of sensors, and resets the sensors if any problem is detected at block 4024. Subsequently, the unit 100 checks the motors and resets any motor problem is detected at block 4028.

Figure 41:
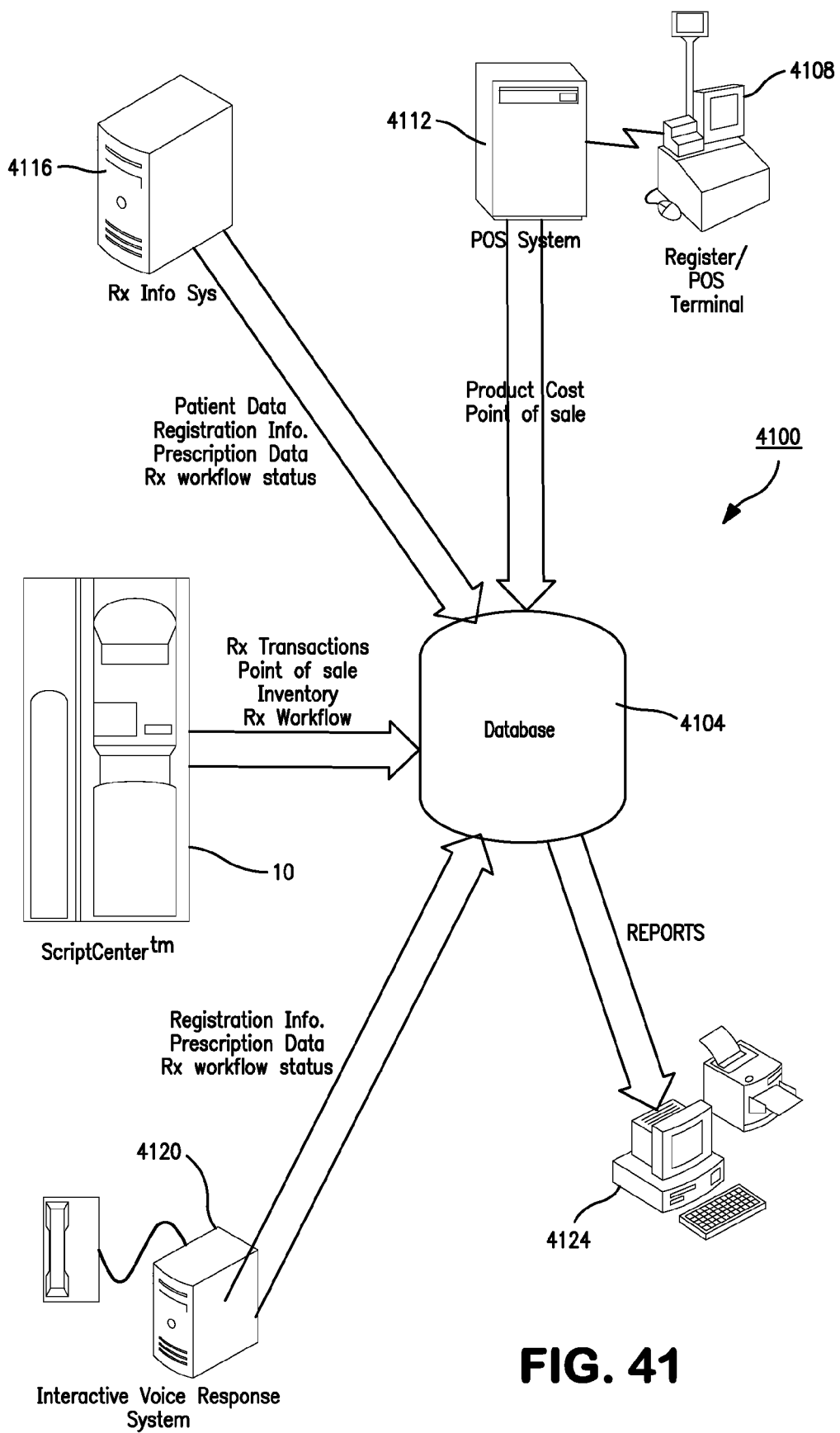
FIG. 41 shows an exemplary data source.

FIG. 41 shows a block diagram illustrating exemplary data source 4100 in the system 2910. For example, the data source 4100 includes a database 4104 that stores information such as consumer information, and prescription information associated with each consumer. A register or a POS terminal 4108 communicates with the POS system 4112 (item 2922 of FIG. 29), and the POS system 4112 communicates information such as product cost and POS information with the database 4104. The pharmacy information system 4116 (item 2914 of FIG. 29) communicates information such as patient data, registration, prescription data, and prescription workflow status with the database 4104. The unit 10 also communicates with the database 4104 exchanging information such as prescription transactions, POS, inventory, and prescription workflow. An IVR system 4120 sends information such as registration, prescription, and workflow status to the database 4104. The database also generates reports that can be accessed securely through a control center 4124.

Although the invention has been described in detail with reference to certain preferred embodiments, variations and modifications exist within the scope and spirit of the invention as described and defined in the following claims.

We claim:

1. A communication network for use in delivering pharmacy-filled prescriptions associated with specific consumers that are stored in a random storage and delivery device comprising:

a random storage and delivery device comprising a housing for securely enclosing at least one hundred prescription storage locations, each prescription storage location designed to store a unique, pharmacy-filled prescription that has been associated with a specific consumer before being placed within the device, a consumer interface, a delivery apparatus that can deliver any pharmacy-filled prescription stored at any prescription storage location, and a dispensing computer that communicates with the consumer interface and the delivery apparatus;

a sensor, located within the housing, for sensing a sensable identifier associated with each consumer-specific prescription; wherein each consumer-specific prescription is randomly stored at a non-predesignated storage location, and said dispensing computer receives information about the identity and location of said stored consumer-specific prescription from said sensor which senses said sensable identifier after said consumer-specific prescription is placed at the non-predesignated prescription storage location, to allow the storage and delivery device to associate said consumer-specific prescription to the non-predesignated storage location after said consumer-specific prescription is stored;

a pharmacy information system for storing electronic records associated with stored consumer-specific prescriptions, which are created by the pharmacy and comprise a unique consumer identifier and a prescription number associated with the consumer; and an interface engine that communicates with the pharmacy information system and the dispensing computer, and through which a unique electronic record corresponding to each consumer-specific prescription stored in the storage and delivery device is transferred from the pharmacy information system to the dispensing computer;

wherein the consumer interface receives identification information from a consumer, the dispensing computer determines the location of a consumer-specific prescription stored within the storage and delivery device for that consumer, and which corresponds to the electronic record for that consumer-specific prescription, and the dispensing computer controls the delivery apparatus to deliver the consumer-specific prescription to the consumer.

2. The communication network of claim 1, wherein the electronic record further comprises information selected from a group consisting of: a drug name, a drug code, a brand name, and a generic name.

3. The communication network of claim 2, wherein the electronic record comprises information selected from a group consisting of: a retail price, a co-pay amount, a consumer insurance information, and a Medicaid information.

4. The communication network of claim 3, wherein the record further comprises an information selected from a group consisting of: a physician name, and a physician contact information.

5. The communication network of claim 1, further comprising a retail store point of sale system that communicates with a retail store's financial accounting system that communicates with the interface engine.

6. The communication network of claim 5, wherein the point of sale system communicates with the pharmacy information system.

7. The communication network of claim 5, wherein the point of sale system communicates with a financial accounting system.

8. The communication network of claim 7, wherein the point of sale system communicates with the pharmacy information system via the interface engine.

9. The communication network of claim 8, wherein the dispensing computer sends a prescription number to the point of sale system via the interface engine, and the point of sale system transmits a purchase price to the dispensing computer via the interface engine.

10. The communication network of claim 8, wherein the dispensing computer sends a prescription number to the pharmacy information system via the interface engine, and the pharmacy information system transmits a purchase price to the dispensing computer via the interface engine.

11. The communication network of claim 9, wherein the dispensing device stores a plurality of unique, pharmacy-filled prescriptions for one consumer, each prescription medication being associated with a different electronic record.

12. The communication network of claim 1, further comprising a controller to control the delivery apparatus, wherein the controller communicates with the dispensing computer or the pharmacy information system.

13. The communication network of claim 12, wherein the delivery apparatus further comprises robotics, and the controller controls the robotics.

14. The communication network of claim 1, wherein the storage and delivery device comprises at least five hundred unique storage locations.

15. The communication network of claim 5, further comprising a storage location database, wherein the database associates every storage location storing a prescription with a specific consumer.

16. The communication network of claim 15, wherein the storage location database further comprises a list of consumers who have registered to use the dispensing device.

17. The communication network of claim 16, wherein the consumer interface further comprises a touch screen and an identification reader, and the dispensing computer communicates with the touch screen and the identification reader.

18. The communication network of claim 17, wherein after identification of the consumer, the dispensing computer receives a user identification from the consumer interface and communicates with the database to compare the consumer's identity with the registered consumers stored in the database.

19. The communication network of claim 18, wherein the dispensing computer queries the storage location database to identify all consumer-specific prescriptions stored within the dispensing device for an identified consumer.

20. The communication network of claim 19, wherein after identification of the consumer, the dispensing computer queries the database to ascertain the storage location of a stored, consumer-specific prescription medication for the identified consumer.

21. The communication network of claim 20, wherein the interface is configured to allow a consumer to select at least one consumer-specific prescription, and the dispensing computer determines the random location in which the selected consumer-specific prescription is stored.

22. The communication network of claim 21, wherein the dispensing computer queries the pharmacy information system to send the most updated electronic record associated with the selected consumer-specific prescription just prior to displaying information about the selected consumer-specific prescription to the consumer.

23. The communication network of claim 15, wherein the storage location database is located within the dispensing computer.

24. The communication network of claim 1, wherein the location of the dispensing computer is selected from the group consisting of: a location within the dispensing apparatus and a location remote from the dispensing apparatus.

25. The communication network of claim 1, wherein the pharmacy information system and the dispensing computer are located on a single node of the network.

26. The communication network of claim 5, wherein the pharmacy information system and pharmacy point of sale system are located on a single node of the network.

27. The communication network of claim 23, wherein the database is located within a device on the network.

28. The communication network of claim 5, wherein the interface engine is located within the dispensing computer.

29. The communication network of claim 28, wherein dispensing computer and the interface engine are located within the storage and delivery device.

30. The communication network of claim 5, wherein the interface engine is located on a device on the network selected from group consisting of: the point of sale system, the pharmacy information system and the dispensing computer.

31. The communication network of claim 5 further comprising a router and a firewall.

32. The communication network of claim 31, wherein the network is configured to allow external access across a virtual private network.

33. The communication network of claim 5, wherein the network comprises a network selected from a group consisting of: an Ethernet network, a virtual private network, a point to point network, a point of sale network, and a controller area network.

34. The communication network of claim 33, wherein the communication network transmits information to the consumer selected from a group consisting of: a prescription price, and a co-pay amount.

35. The communication network of claim 1, further comprising a means for communicating with a consumer located remotely from the dispensing device.

36. The communication network of claim 5, wherein over the counter items are stored within the storage and delivery device, and available for purchase by the consumer.

37. The communication network of claim 5, wherein the sensor comprises an electronic reader, and the dispensing computer communicates with the electronic reader.

38. The communication network of claim 1, wherein the sensable identifier is a barcode, and the sensor is a barcode reader.

39. The communication network of claim 1, wherein the dispensing computer and the pharmacy information system are within the same housing.

40. The communication network of claim 9, wherein storage and delivery device is located such that at least one surface of the housing is in a secured area only accessible to pharmacy personnel and at least one surface of the housing of the storage and delivery device is accessible to consumers.

41. A communication network for use in a purchase transaction for a pharmacy-filled prescription stored in a random storage, random delivery device, where said prescriptions are associated with specific consumers before being placed within the device, comprising:
a networkable storage and delivery device comprising a housing:
(i) for securely enclosing at least one hundred prescription storage locations, wherein the storage locations are unique in that every stored consumer-specific prescription may be different from every other one;
(ii) a user interface; and
(iii) a delivery apparatus that can deliver any pharmacy-filled prescription stored at any storage location;
a sensor, located within the housing, for sensing a sensable identifier associated with each consumer-specific prescription; wherein each consumer-specific prescription is randomly stored at a non-predesignated storage location, and said dispensing computer receives information about the identity and location of said stored consumer-specific prescription from said sensor which senses said sensable identifier after said consumer-specific prescription is placed at the non-predesignated prescription storage location, to allow the storage and delivery device to associate said consumer-specific prescription to the non-predesignated storage location after said consumer-specific prescription is stored;
a pharmacy information system located remotely from the storage and delivery device, which contains a plurality of electronic records created by a pharmacy and associated with a consumer-specific prescription, wherein an electronic record comprises a consumer information element, a prescription information element, and a medication information element;

a dispenser computer communicating with the user interface and the delivery apparatus;

a retail store point of sale system that communicates with a retail store's financial accounting system; and an interface communicating with the pharmacy information system, retail store point of sale system, and the dispenser computer, which enables the transfer of electronic records from the pharmacy information system to the dispenser computer, each electronic record corresponding to a consumer-specific prescription stored at a unique storage location in the storage and delivery device;

wherein the dispenser computer, after a user interacts with the user interface, accesses information taken from a transferred record associated with that user or a third party having a predefined relationship with that user to communicate purchase transaction information to the consumer, and after receiving payment, directs the delivery apparatus to deliver to the user a consumer-specific prescription associated with the transferred record after receiving payment;

and wherein the retail store's financial accounting system receives purchase information.

42. The communication network of claim 41, wherein the prescription information element is a prescription number.

43. The communication network of claim 42, wherein the dispenser computer transmits the prescription number to the interface.

44. The communication network of claim 43, wherein the interface transmits the prescription number to the point of sale system.

45. The communication network of claim 41, wherein the dispenser computer receives the purchase price or co-payment amount of the prescription medication from the interface.

46. The communication network of claim 41, wherein the storage and delivery device further comprises a means for receiving payment.

47. The communication network of claim 46, wherein the means for receiving payment is a credit card reader a cash acceptor, or a debit card reader.

48. The communication network of claim 41, wherein the transferred record contains information about a consumer-specific prescription that was filled for and associated with the user interacting with the dispensing device.

49. The communication network of claim 41, wherein the transferred record is directed to a consumer-specific prescription that was filled for a third person for whom the user is authorized to receive the prescription.

50. The communication network of claim 41, wherein the user interface further comprises a touchscreen.

51. The communication network of claim 50, wherein the touchscreen can display a listing of all consumer-specific prescriptions that are available for pick-up by the user, including all consumer-specific prescriptions filled for the user and all prescriptions filled for persons who have authorized the consumer to pickup their consumer-specific prescriptions.

52. The communication network of claim 51, wherein the user requests delivery of all consumer-specific prescriptions stored in the device that the user is approved to receive, and the delivery apparatus delivers all such consumer-specific prescriptions.

53. A communication network for use in a purchase transaction for a pharmacy-filled prescription stored in a random storage, random delivery device, where prescriptions are associated with specific consumers before being placed within the device, comprising:

a storage and delivery device comprising a housing for securely enclosing prescription storage locations, a user interface means, and a delivery means, wherein each prescription storage location is capable of storing a different prescription;

a sensor, located within the housing, for sensing a sensable identifier associated with each consumer-specific prescription; wherein each consumer-specific prescription is randomly stored at a non-predesignated storage location, and said dispensing computer receives information about the identity and location of said stored consumer-specific prescription from said sensor which senses said sensable identifier after said consumer-specific prescription is placed at the non-predesignated prescription storage location, to allow the storage and delivery device to associate said consumer-specific prescription to the non-predesignated storage location after said consumer-specific prescription is stored;

a dispensing computer means for communicating with and controlling the delivery means;

a pharmacy information system means, located remotely from the delivery device, for storing a plurality of electronic records, wherein a record is created by a pharmacy and comprises a consumer name, a drug name, and a co-pay amount and is associated with a prescription placed within the device;

a point of sale means for recording transactions made at the device; and an interface means for communicating with the dispensing computer means, pharmacy information system means, and the point of sale means, and which enables the transfer of an electronic record from the pharmacy information system means to the dispensing computer means, wherein the dispensing computer means controls the delivery means and uses information obtained from the transferred record to locate and to deliver to the consumer a consumer-specific stored prescription that the consumer is authorized to receive; and wherein the dispensing computer means communicates with the interface means to provide the point of sale means information to account for a purchase transaction.

54. The communication network of claim 1, wherein the identification information further comprises a PIN.

55. The communication network of claim 4, wherein the record further comprises a information selected from a group consisting of a non-child resistant packaging information, a consumer address, a consumer birth date, a consumer phone number, a consumer home phone number, a consumer fax number, a consumer mobile phone number, a consumer pager number, and a consumer email address.

56. The communication network of claim 5, wherein the electronic record further comprises information selected from a group consisting of: a drug name, a drug code, a brand name, and a generic name.

57. The communication network of claim 56, wherein the electronic record comprises information selected from a group consisting of: a retail price, a co-pay information, a co-pay amount, a consumer insurance information, and a Medicaid information.

58. The communication network of claim 56, wherein the electronic record further comprises a information selected from a group consisting of: a physician name, and a physician contact information.

59. The communication network of claim 58, wherein the electronic record further comprises a information selected from a group consisting of a non-child resistant packaging information, a consumer address, a consumer birth date, a consumer phone number, a consumer home phone number, a consumer fax number, a consumer mobile phone number, a consumer pager number, and a consumer email address.

60. The communication network of claim 5, wherein the dispensing computer determines that a plurality of consumer-specific prescriptions stored within the dispensing device have been associated with the consumer who has identified himself or herself, and the dispensing computer transmits to the consumer interface the names of the prescriptions on the touchscreen.

61. The communication network of claim 35, wherein the dispensing computer communicates with a remotely located consumer through a communication selected from a group consisting of: an email, a phone call, a page, a text message, and a fax.

62. The communication network of claim 1, wherein the pharmacy information system is updated to indicate that the consumer-specific prescription has been delivered to the consumer.

63. The communication network of claim 5, wherein the interface engine transmits purchase information to the point of sale system.

64. The communication network of claim 41, wherein the consumer information element is the user's name.

65. The communication network of claim 42, wherein the consumer information element further comprises information selected from a group consisting of: a consumer name, a physician name, and a physician contact information.

66. The communication network of claim 65, wherein the information element further comprises a refill number, a co-pay information, and a co-pay amount.

67. The communication network of claim 66, wherein the medication information element comprises information selected from a group consisting of: a drug name, a brand name, retail price, and a generic name.

68. The communication network of claim 41, wherein the consumer information element further comprises a consumer name, and one or more information selected from a group consisting of: a consumer birth date, a consumer phone number, physician name, a consumer home phone number, a consumer fax number, a consumer mobile phone number, a consumer pager number, and a consumer's email address.

69. The communication network of claim 68, wherein the prescription information element comprises information selected from a group consisting of: a refill number, a fill date, a consumer's insurance information, a consumer's Medicaid information, a co pay information, and a co pay amount.

70. The communication network of claim 69, wherein the medication information element comprises one or more information selected from a group consisting of: a prescription number, a drug name, a drug code, a tax information, a brand name, a generic name, a retail price, a fill cost, a drug cost, a physician information, and a physician contact information.

71. The communication network of claim 70, wherein the prescription information element further comprises information selected from a group consisting of: a prescription number, a refill number, a fill date, a maximum refills, a quantity ordered, a store number, a drug cost, a consumer's insurance information, a consumer's Medicaid information, a co pay information, and a co pay.

72. The communication network of claim 41, wherein the device is capable of storing over the counter items.

73. The communication network of claim 72, wherein an over the counter item is purchased substantially contemporaneously with a consumer-specific prescription.

74. The communication network of claim 41 further comprising at least 500 storage locations.

75. The communication network of claim 1, wherein substantially all the stored consumer-specific prescriptions are refills.

76. A communication network for use in a purchase transaction in a retail pharmacy using a random storage, random delivery device that stores pharmacy-filled prescriptions, each associated with a particular consumer before being stored, comprising an automated random storage; random delivery device comprising a housing, a dispenser computer, a delivery apparatus, and at least one hundred prescription storage locations, each prescription storage location capable of storing a unique pharmacy-filled prescription, and being accessed by the delivery apparatus upon demand;

a sensor, located within the housing, for sensing a sensable identifier associated with each consumer-specific prescription; wherein each consumer-specific prescription is randomly stored at a non-predesignated storage location, and said dispensing computer receives information about the identity and location of said stored consumer-specific prescription from said sensor which senses said sensable identifier after said consumer-specific prescription is placed at the non-predesignated prescription storage location, to allow the storage and delivery device to associate said consumer-specific prescription to the non-predesignated storage location after said consumer-specific prescription is stored;

a consumer interface, a pharmacy computer system located remotely from the storage and delivery device, which contains electronic records created by the pharmacy and associated with consumer-specific prescriptions, wherein each record associated with a stored consumer-specific prescription is first created before a consumer-specific prescription is placed at a storage location and comprises a consumer name, a prescription number, and a drug name;

an electronic identification associated with a consumer-specific prescription, which electronically links the consumer-specific prescription and the information record;

a pharmacy point of sale system;

an interface communicating with the pharmacy computer system, the pharmacy point of sale system, and the dispensing computer, the interface enabling the transfer of electronic records from the pharmacy computer system to the dispensing computer, each electronic record corresponding to consumer-specific prescriptions stored at a unique storage location in the storage and delivery device;

wherein the user interface accepts identification from the consumer, the dispensing computer provides transaction information to the consumer, the user interface accepts payment from the consumer, the dispensing computer controls the delivery apparatus to deliver to the consumer a consumer-specific prescription that corresponds to the electronic record for that consumer-specific prescription medication, and the interface transmits purchase information to the store point of sale system.

77. The communication network of claim 5, wherein the electronic record further comprises information selected from a group consisting of: a drug name, a drug code, a brand name, and a generic name.

78. The communication network of claim 38, wherein the barcode reader moves to a location proximate to the barcode in order to sense said barcode.

79. The communication network of claim 41, wherein the sensable identifier is a barcode, and the sensor is a barcode reader.

80. The communication network of claim 79, wherein the barcode reader moves to a location proximate to the barcode in order to sense said barcode.

81. The communication network of claim 53, wherein the sensable identifier is a barcode, and the sensor is a barcode reader.

82. The communication network of claim 81, wherein the barcode reader moves to a location proximate to the barcode in order to sense said barcode.

83. The communication network of claim 76 wherein the sensable identifier is a barcode, and the sensor is a barcode reader.

84. The communication network of claim 83, wherein the barcode reader moves to a location proximate to the barcode in order to sense said barcode.

* * * * *